US011052145B2

(12) United States Patent
Møller et al.

(10) Patent No.: US 11,052,145 B2
(45) Date of Patent: Jul. 6, 2021

(54) **PROTEINS AND NUCLEIC ACIDS USEFUL IN VACCINES TARGETING *STAPHYLOCOCCUS AUREUS***

(71) Applicant: Evaxion Biotech ApS, København K (DK)

(72) Inventors: Niels Iversen Møller, København K (DK); Andreas Holm Mattsson, København K (DK)

(73) Assignee: Evaxion Biotech A/S, Hørsholm (DK)

(*) Notice: Subject to any disclaimer, the term of this patent is extended or adjusted under 35 U.S.C. 154(b) by 0 days.

(21) Appl. No.: 16/887,611

(22) Filed: May 29, 2020

(65) Prior Publication Data

US 2020/0306356 A1 Oct. 1, 2020

Related U.S. Application Data

(60) Continuation of application No. 16/023,741, filed on Jun. 29, 2018, now Pat. No. 10,675,340, which is a division of application No. 15/387,814, filed on Dec. 22, 2016, now Pat. No. 10,034,928, which is a continuation of application No. 14/802,602, filed on Jul. 17, 2015, now Pat. No. 9,534,022, which is a division of application No. 14/110,475, filed as application No. PCT/EP2012/056069 on Apr. 3, 2012, now Pat. No. 9,085,631.

(60) Provisional application No. 61/473,376, filed on Apr. 8, 2011.

(30) Foreign Application Priority Data

Apr. 8, 2011 (DK) ................................ 2011 70167

(51) Int. Cl.

| | |
|---|---|
| ***A61K 39/085*** | (2006.01) |
| ***C07K 14/31*** | (2006.01) |
| ***C12Q 1/68*** | (2018.01) |
| ***C07K 16/12*** | (2006.01) |
| ***C12Q 1/689*** | (2018.01) |
| *A61K 39/00* | (2006.01) |

(52) U.S. Cl.

CPC ............ *A61K 39/085* (2013.01); *C07K 14/31* (2013.01); *C07K 16/1271* (2013.01); *C12Q 1/689* (2013.01); *A61K 2039/505* (2013.01); *A61K 2039/545* (2013.01); *A61K 2039/55* (2013.01); *A61K 2039/55505* (2013.01); *A61K 2039/6081* (2013.01); *C07K 2317/34* (2013.01); *C12Q 2600/158* (2013.01)

(58) Field of Classification Search

CPC .. A61K 38/00; A61K 2300/00; A61K 31/716; A61K 31/155; A61K 31/44; A61K 38/16; A61K 38/482; A61K 6/087; A61K 2039/5156; A61K 2039/523; A61K 2039/5256; A61K 38/1709; A61K 38/4826; A61K 38/486; A61K 38/4873

See application file for complete search history.

(56) References Cited

U.S. PATENT DOCUMENTS

| | | | |
|---|---|---|---|
| 4,683,195 | A | 7/1987 | Mullis et al. |
| 4,683,202 | A | 7/1987 | Mullis |
| 4,684,611 | A | 8/1987 | Schilperoort et al. |
| 4,800,159 | A | 1/1989 | Mullis et al. |
| 4,879,236 | A | 11/1989 | Smith et al. |
| 4,952,500 | A | 8/1990 | Finnerty et al. |
| 5,302,523 | A | 4/1994 | Coffee et al. |
| 5,322,783 | A | 6/1994 | Tomes et al. |
| 5,384,253 | A | 1/1995 | Krzyzek et al. |
| 5,464,765 | A | 11/1995 | Coffee et al. |
| 5,538,877 | A | 7/1996 | Lundquist et al. |
| 5,538,880 | A | 7/1996 | Lundquist et al. |
| 5,550,318 | A | 8/1996 | Adams et al. |
| 5,563,055 | A | 10/1996 | Townsend et al. |
| 5,580,859 | A | 12/1996 | Felgner et al. |
| 5,589,466 | A | 12/1996 | Felgner et al. |
| 5,591,616 | A | 1/1997 | Hiei et al. |
| 5,610,042 | A | 3/1997 | Chang et al. |
| 5,656,610 | A | 8/1997 | Shuler et al. |
| 5,702,932 | A | 12/1997 | Hoy et al. |
| 5,736,524 | A | 4/1998 | Content et al. |
| 5,780,448 | A | 7/1998 | Davis |
| 5,789,215 | A | 8/1998 | Berns et al. |
| 5,843,650 | A | 12/1998 | Segev |
| 5,846,709 | A | 12/1998 | Segev |
| 5,846,783 | A | 12/1998 | Wu et al. |
| 5,849,497 | A | 12/1998 | Steinman |
| 5,849,546 | A | 12/1998 | Sousa et al. |
| 5,849,547 | A | 12/1998 | Cleuziat et al. |
| 5,858,652 | A | 1/1999 | Laffler et al. |

(Continued)

FOREIGN PATENT DOCUMENTS

| | | |
|---|---|---|
| FR | 2944807 | 10/2010 |
| GB | 2202328 | 9/1988 |

(Continued)

OTHER PUBLICATIONS

Feldgarden, M. et al, "*Staphylococcus aureus* subsp. *aureus* 68-397; Full-predicted protein", XP002682642, EBI accession C8A9W6, (Oct. 13, 2009).

(Continued)

*Primary Examiner* — Padmavathi Baskar
(74) *Attorney, Agent, or Firm* — McHale & Slavin, P.A.

(57) ABSTRACT

Disclosed are novel immunogenic proteins derived from *Staphylococcus aureus*, as well as methods for their use in conferring protective immunity against *S. aureus* infections. Also disclosed are nucleic acids encoding the proteins and methods of use of these nucleic acids.

14 Claims, No Drawings

Specification includes a Sequence Listing.

(56) References Cited

U.S. PATENT DOCUMENTS

| | | | |
|---|---|---|---|
| 5,866,366 | A | 2/1999 | Kallender |
| 5,871,986 | A | 2/1999 | Boyce |
| 5,916,776 | A | 6/1999 | Kumar |
| 5,922,574 | A | 7/1999 | Minter |
| 5,925,565 | A | 7/1999 | Berlioz et al. |
| 5,928,905 | A | 7/1999 | Stemmer et al. |
| 5,928,906 | A | 7/1999 | Koster et al. |
| 5,932,451 | A | 8/1999 | Wang et al. |
| 5,935,819 | A | 8/1999 | Eichner et al. |
| 5,935,825 | A | 8/1999 | Nishimura et al. |
| 5,939,291 | A | 8/1999 | Loewy et al. |
| 5,942,391 | A | 8/1999 | Zhang et al. |
| 5,945,100 | A | 8/1999 | Fick |
| 5,981,274 | A | 11/1999 | Tyrrell et al. |
| 5,994,624 | A | 11/1999 | Trolinder et al. |
| 7,608,276 | B2 | 10/2009 | Masignani et al. |
| 8,703,148 | B2 | 4/2014 | Biemans et al. |
| 9,085,631 | B2 | 7/2015 | Moller et al. |
| 9,534,022 | B2 | 1/2017 | Moller et al. |
| 10,034,928 | B2 | 7/2018 | Moller et al. |
| 2014/0072556 | A1 | 3/2014 | Moller et al. |
| 2018/0296659 | A1 | 10/2018 | Moller et al. |

FOREIGN PATENT DOCUMENTS

| | | |
|---|---|---|
| WO | WO8909284 | 10/1989 |
| WO | WO9014837 | 12/1990 |
| WO | WO9409699 | 5/1994 |
| WO | WO9506128 | 3/1995 |
| WO | WO9820734 | 5/1998 |
| WO | WO2002094868 | 11/2002 |
| WO | WO2005014857 | 2/2005 |
| WO | WO2010119343 | 10/2010 |
| WO | WO2012136653 | 10/2012 |

OTHER PUBLICATIONS

Feldgarden, M. et al, "*Staphylococcus aureus* subsp. strain *aureus* MRSA252, complete genome", XP002682643, EM-PRO accession BX571856.1, 766363-766752, (Jun. 23, 2004).

Li, W. et al, Structural insights into the pro-apoptotic function of mitochondrial serine protease HtrA2/0mi:, Nat. Struct. Biol., vol. 9(6), pp. 436-441, (Jun. 2002).

Holden, M. et al, *Staphlyococcus aureus* subsp., *aureus* strain MRSA252, complete genome, XP002682643, (Jun. 2004, updated May 2009).

Donnelly, J. et al, "DNA vaccines", Ann. Rev. Immunol., vol. 15, pp. 617-648, (1997).

Robinson, H. et, "DNA vaccines", Seminars in Immunology, vol. 9(5), pp. 271-283, (Oct. 1997) Abstract.

Kohler, G. et al, "Continuous cultures of fused cells secreting antibody of predefined specificity", Nature, vol. 256(5517), pp. 495-497, (1975) Abstract.

UniProt: Accession No. B5WZQ3 2008 (Year: 2008).

SEQUENCE LISTING

<160> NUMBER OF SEQ ID NOS: 59

<210> SEQ ID NO 1
<211> LENGTH: 154
<212> TYPE: PRT
<213> ORGANISM: Staphylococcus aureus

<400> SEQUENCE: 1

Met Lys Arg Leu Leu Gly Leu Leu Leu Val Ser Thr Leu Val Leu Ser
1 5 10 15

Ala Cys Gly Asn Asp Glu Asn Gln Glu Glu Ser Lys Lys Glu Val Lys
20 25 30

Ser Lys Glu Lys Lys Ile Glu Lys Glu Lys Glu Asn Lys Ser Lys Lys
35 40 45

Asp Lys Glu Lys Glu Val Ala Thr Gln Gln Gln Pro Asp Asn Gln Thr
50 55 60

Val Glu Gln Pro Gln Ser Gln Glu Gln Ser Val Gln Gln Pro Gln Gln
65 70 75 80

Gln Ile Pro Gln Asn Ser Val Pro Gln Gln Asn Val Gln Val Gln Gln
85 90 95

Asn Lys Lys Gln Lys Val Asp Leu Asn Asn Met Pro Pro Thr Asp Phe
100 105 110

Ser Thr Glu Gly Met Ser Glu Gln Ala Gln Lys Gln Ile Glu Glu Leu
115 120 125

Ser Met Gln Lys Asp Tyr His Gly Leu Ser Gln Arg Glu Tyr Asn Asp
130 135 140

Arg Val Ser Glu Ile Ile Asn Asn Asp Asn
145 150

<210> SEQ ID NO 2
<211> LENGTH: 184
<212> TYPE: PRT
<213> ORGANISM: Staphylococcus aureus

<400> SEQUENCE: 2

Met Leu Lys Gly Cys Gly Gly Cys Leu Ile Ser Phe Ile Ile Leu Ile
1 5 10 15

Ile Leu Leu Ser Ala Cys Ser Met Met Phe Ser Asn Asn Asp Asn Ser
20 25 30

Thr Ser Asn Gln Ser Ser Lys Thr Gln Leu Thr Gln Lys Asp Glu Asp
35 40 45

Lys Ser Glu Asn Met Pro Glu Glu Lys Ser Glu Ser Glu Thr Asp Lys
50 55 60

Asp Leu Gln Ser Thr Glu Glu Val Pro Ala Asn Glu Asn Thr Glu Asn

-continued

```
65                  70                  75                  80

Asn Gln His Glu Ile Asp Glu Ile Thr Thr Thr Asp Gln Ser Asp Asp
                85                  90                  95

Glu Ile Asn Thr Pro Asn Val Ala Glu Glu Glu Ser Gln Asp Asp Leu
            100                 105                 110

Lys Asp Asp Leu Lys Glu Lys Gln Gln Pro Ser Asp His His Gln Ser
        115                 120                 125

Thr Gln Pro Lys Thr Ser Pro Ser Thr Glu Thr Asn Lys Gln Gln Ser
    130                 135                 140

Phe Ala Asn Cys Lys Gln Leu Arg Gln Val Tyr Pro Asn Gly Val Thr
145                 150                 155                 160

Ala Asp His Pro Ala Tyr Arg Pro His Leu Asp Arg Asp Lys Asp Lys
                165                 170                 175

Arg Ala Cys Glu Pro Asp Lys Tyr
            180


<210> SEQ ID NO 3
<211> LENGTH: 129
<212> TYPE: PRT
<213> ORGANISM: Staphylococcus aureus

<400> SEQUENCE: 3

Met Lys Lys Leu Ile Ile Ser Ile Met Ala Ile Met Leu Phe Leu Thr
1               5                   10                  15

Gly Cys Gly Lys Ser Gln Glu Lys Ala Thr Leu Glu Lys Asp Ile Asp
            20                  25                  30

Asn Leu Gln Lys Glu Asn Lys Glu Leu Lys Asp Lys Lys Glu Lys Leu
        35                  40                  45

Gln Gln Glu Lys Glu Lys Leu Ala Asp Lys Gln Lys Asp Leu Glu Lys
    50                  55                  60

Glu Val Lys Asp Leu Lys Pro Ser Lys Glu Asp Asn Lys Asp Asp Lys
65                  70                  75                  80

Lys Asp Glu Asp Lys Asn Lys Asp Lys Asp Lys Glu Ala Ser Gln Asp
                85                  90                  95

Lys Gln Ser Lys Asp Gln Thr Lys Ser Ser Asp Lys Asp Asn His Lys
            100                 105                 110

Lys Pro Thr Ser Thr Asp Lys Asp Gln Lys Ala Asn Asp Lys His Gln
        115                 120                 125

Ser


<210> SEQ ID NO 4
<211> LENGTH: 993
<212> TYPE: PRT
<213> ORGANISM: Staphylococcus aureus

<400> SEQUENCE: 4

Met Lys Asn Ala Phe Lys Leu Phe Lys Met Asp Leu Lys Lys Val Ala
1               5                   10                  15

Lys Thr Pro Ala Val Trp Ile Ile Leu Ala Gly Leu Ala Ile Leu Pro
            20                  25                  30

Ser Phe Tyr Ala Trp Phe Asn Leu Trp Ala Met Trp Asp Pro Tyr Gly
        35                  40                  45

Asn Thr Gly His Ile Lys Val Ala Val Val Asn Glu Asp Lys Gly Asp
    50                  55                  60

Thr Ile Arg Gly Lys Lys Val Asn Val Gly Asn Thr Met Val Asn Thr
65                  70                  75                  80
```

-continued

```
Leu Lys Lys Asn Lys Ser Phe Asp Trp Gln Phe Val Ser Arg Glu Lys
                85                  90                  95

Ala Asp His Glu Ile Lys Met Gly Lys Tyr Phe Ala Gly Ile Tyr Ile
            100                 105                 110

Pro Ser Lys Phe Thr His Glu Ile Thr Gly Thr Leu Arg Lys Gln Pro
        115                 120                 125

Gln Lys Ala Asp Val Glu Phe Lys Val Asn Gln Lys Ile Asn Ala Val
    130                 135                 140

Ala Ser Lys Leu Thr Asp Thr Gly Ser Ser Val Val Val Glu Lys Ala
145                 150                 155                 160

Asn Glu Gln Phe Asn Lys Thr Val Thr Arg Ala Leu Leu Glu Glu Ala
                165                 170                 175

Asn Lys Ala Gly Leu Thr Ile Glu Glu Asn Val Pro Thr Ile Asn Lys
            180                 185                 190

Ile Lys Asn Ala Val Tyr Ser Ala Asp Lys Ala Leu Pro Lys Ile Asn
        195                 200                 205

Asp Phe Ala Asn Lys Ile Val Tyr Leu Asn Asn His Gln Ala Asp Leu
    210                 215                 220

Asp Lys Tyr Ala Asn Asp Phe Arg Lys Leu Gly Asn Tyr Lys Gly Asp
225                 230                 235                 240

Ile Leu Asp Ala Gln Lys Lys Leu Asn Glu Val Asn Gly Ala Ile Pro
                245                 250                 255

Gln Leu Asn Glu Lys Ala Lys Leu Ile Leu Ala Leu Asn Asn Tyr Met
            260                 265                 270

Pro Lys Ile Glu Lys Ala Leu Asn Phe Ala Ala Asp Asp Val Pro Ala
        275                 280                 285

Gln Phe Pro Lys Ile Asn Gln Gly Leu Asn Ile Ala Ser Gln Gly Ile
    290                 295                 300

Asp Gln Ala Asn Gly Gln Leu Asn Asp Ala Lys Gly Phe Val Thr Gln
305                 310                 315                 320

Val Arg Ser Arg Val Gly Asp Tyr Gln Glu Ala Ile Arg Arg Ala Gln
                325                 330                 335

Asp Leu Asn Arg Arg Asn Gln Gln Gln Ile Pro Gln Asn Ser Ala Ala
            340                 345                 350

Asn Asn Glu Thr Ser Asn Ser Ala Pro Ala Ala Gly Asn Gly Val Thr
        355                 360                 365

Ser Thr Pro Pro Ser Ala Pro Asn Gly Asn Thr Thr Pro Asn Asn Asn
    370                 375                 380

Val Thr Gln Asn Thr Ala Pro Asn Ser Asn Asn Ala Pro Val Ser Thr
385                 390                 395                 400

Thr Pro Gln Ser Thr Ser Gly Lys Lys Asp Gly Gln Ser Phe Ala Asp
                405                 410                 415

Ile Thr Thr Thr Gln Val Ser Thr Ala Asn Glu Asn Thr Gln Asn Ile
            420                 425                 430

Thr Asp Lys Asp Val Lys Ser Met Glu Ala Ala Leu Thr Gly Ser Leu
        435                 440                 445

Leu Ser Leu Ser Asn Asn Leu Asp Thr Gln Ala Lys Ala Ala Gln Lys
    450                 455                 460

Asp Ser Gln Ala Leu Arg Asn Ile Ser Tyr Gly Ile Leu Ala Ser Asp
465                 470                 475                 480

Lys Pro Ser Asp Phe Arg Glu Ser Leu Asp Asn Val Lys Ser Gly Leu
                485                 490                 495
```

```
Glu Tyr Thr Thr Gln Tyr Asn Gln Gln Phe Ile Asp Thr Leu Lys Glu
            500                 505                 510

Ile Glu Lys Asn Glu Asn Val Asp Leu Ser Lys Glu Ile Asp Lys Val
        515                 520                 525

Lys Thr Ala Asn Asn Arg Ile Asn Glu Ser Leu Arg Leu Val Asn Gln
    530                 535                 540

Leu Ser Asn Ala Leu Lys Asn Gly Ser Ser Gly Thr Ala Glu Ala Thr
545                 550                 555                 560

Lys Leu Leu Asp Gln Leu Ser Lys Leu Asp Ser Ser Leu Ser Ser Phe
                565                 570                 575

Arg Asp Tyr Val Lys Lys Asp Leu Asn Ser Ser Leu Val Ser Ile Ser
            580                 585                 590

Gln Arg Ile Met Asp Glu Leu Asn Lys Gly Gln Thr Ala Leu Ser Asn
        595                 600                 605

Val Gln Ser Lys Leu Asn Thr Ile Asp Gln Val Ile Asn Ser Gly Gln
    610                 615                 620

Ser Ile Leu Lys Asn Gly Lys Thr Arg Ile Asp Arg Leu Gln Thr Val
625                 630                 635                 640

Leu Pro Ser Ile Glu Gln Gln Tyr Ile Ser Ala Ile Lys Asn Ala Gln
                645                 650                 655

Ala Asn Phe Pro Lys Val Lys Ser Asp Val Ala Lys Ala Ala Asn Phe
            660                 665                 670

Val Arg Asn Asp Leu Pro Gln Leu Glu Gln Arg Leu Thr Asn Ala Thr
        675                 680                 685

Ala Ser Val Asn Lys Asn Leu Pro Thr Leu Leu Asn Gly Tyr Asp Gln
    690                 695                 700

Ala Val Gly Leu Leu Asn Lys Asn Gln Pro Gln Ala Lys Lys Ala Leu
705                 710                 715                 720

Ser Asp Leu Ala Asp Phe Ala Gln Asn Lys Leu Pro Asp Val Glu Lys
                725                 730                 735

Asp Leu Lys Lys Ala Asn Lys Ile Phe Lys Lys Leu Asp Lys Asp Asp
            740                 745                 750

Ala Val Asp Lys Leu Ile Asp Thr Leu Lys Asn Asp Leu Lys Lys Gln
        755                 760                 765

Ala Gly Ile Ile Ala Asn Pro Ile Asn Lys Lys Thr Val Asp Val Phe
    770                 775                 780

Pro Val Lys Asp Tyr Gly Ser Gly Met Thr Pro Phe Tyr Thr Ala Leu
785                 790                 795                 800

Ser Val Trp Val Gly Ala Leu Leu Met Val Ser Leu Leu Thr Val Asp
                805                 810                 815

Asn Lys His Lys Ser Leu Glu Pro Val Leu Thr Thr Arg Gln Val Phe
            820                 825                 830

Leu Gly Lys Ala Gly Phe Phe Ile Met Leu Gly Met Leu Gln Ala Leu
        835                 840                 845

Ile Val Ser Val Gly Asp Leu Leu Ile Leu Lys Ala Gly Val Glu Ser
    850                 855                 860

Pro Val Leu Phe Val Leu Ile Thr Ile Phe Cys Ser Ile Ile Phe Asn
865                 870                 875                 880

Ser Ile Val Tyr Thr Cys Val Ser Leu Leu Gly Asn Pro Gly Lys Ala
                885                 890                 895

Ile Ala Ile Val Leu Leu Val Leu Gln Ile Ala Gly Gly Gly Gly Thr
            900                 905                 910

Phe Pro Ile Gln Thr Thr Pro Gln Phe Phe Gln Asn Ile Ser Pro Tyr
```

```
        915                 920                 925

Leu Pro Phe Thr Tyr Ala Ile Asp Ser Leu Arg Glu Thr Val Gly Gly
    930                 935                 940

Ile Val Pro Glu Ile Leu Ile Thr Lys Leu Ile Ile Leu Thr Leu Phe
945                 950                 955                 960

Gly Ile Gly Phe Phe Val Val Gly Leu Ile Leu Lys Pro Val Thr Asp
                965                 970                 975

Pro Leu Met Lys Arg Val Ser Glu Lys Val Asp Gln Ser Asn Val Thr
            980                 985                 990

Glu


<210> SEQ ID NO 5
<211> LENGTH: 2066
<212> TYPE: PRT
<213> ORGANISM: Staphylococcus aureus

<400> SEQUENCE: 5

Met Asn Glu Lys Val Glu Gly Met Thr Leu Glu Leu Lys Leu Asp His
1               5                   10                  15

Leu Gly Val Gln Glu Gly Met Lys Gly Leu Lys Arg Gln Leu Gly Val
            20                  25                  30

Val Asn Ser Glu Met Lys Ala Asn Leu Ser Ala Phe Asp Lys Ser Glu
        35                  40                  45

Lys Ser Met Glu Lys Tyr Gln Ala Arg Ile Lys Gly Leu Asn Asp Arg
    50                  55                  60

Leu Lys Val Gln Lys Lys Met Tyr Ser Gln Val Glu Asp Glu Leu Lys
65                  70                  75                  80

Gln Val Asn Ala Asn Tyr Gln Lys Ala Lys Ser Ser Val Lys Asp Val
                85                  90                  95

Glu Lys Ala Tyr Leu Lys Leu Val Glu Ala Asn Lys Lys Glu Lys Leu
            100                 105                 110

Ala Leu Asp Lys Ser Lys Glu Ala Leu Lys Ser Ser Asn Thr Glu Leu
        115                 120                 125

Lys Lys Ala Glu Asn Gln Tyr Lys Arg Thr Asn Gln Arg Lys Gln Asp
    130                 135                 140

Ala Tyr Gln Lys Leu Lys Gln Leu Arg Asp Ala Glu Gln Lys Leu Lys
145                 150                 155                 160

Asn Ser Asn Gln Ala Thr Thr Ala Gln Leu Lys Arg Ala Ser Asp Ala
                165                 170                 175

Val Gln Lys Gln Ser Ala Lys His Lys Ala Leu Val Glu Gln Tyr Lys
            180                 185                 190

Gln Glu Gly Asn Gln Val Gln Lys Leu Lys Val Gln Asn Asp Asn Leu
        195                 200                 205

Ser Lys Ser Asn Asp Lys Ile Glu Ser Ser Tyr Ala Lys Thr Asn Thr
    210                 215                 220

Lys Leu Lys Gln Thr Glu Lys Glu Phe Asn Asp Leu Asn Asn Thr Ile
225                 230                 235                 240

Lys Asn His Ser Ala Asn Val Ala Lys Ala Glu Thr Ala Val Asn Lys
                245                 250                 255

Glu Lys Ala Ala Leu Asn Asn Leu Glu Arg Ser Ile Asp Lys Ala Ser
            260                 265                 270

Ser Glu Met Lys Thr Phe Asn Lys Glu Gln Met Ile Ala Gln Ser His
        275                 280                 285

Phe Gly Lys Leu Ala Ser Gln Ala Asp Val Met Ser Lys Lys Phe Ser
```

```
    290                 295                 300

Ser Ile Gly Asp Lys Met Thr Ser Leu Gly Arg Thr Met Thr Met Gly
305                 310                 315                 320

Val Ser Thr Pro Ile Thr Leu Gly Leu Gly Ala Ala Leu Lys Thr Ser
                325                 330                 335

Ala Asp Phe Glu Gly Gln Met Ser Arg Val Gly Ala Ile Ala Gln Ala
            340                 345                 350

Ser Ser Lys Asp Leu Lys Ser Met Ser Asn Gln Ala Val Asp Leu Gly
        355                 360                 365

Ala Lys Thr Ser Lys Ser Ala Asn Glu Val Ala Lys Gly Met Glu Glu
    370                 375                 380

Leu Ala Ala Leu Gly Phe Asn Ala Lys Gln Thr Met Glu Ala Met Pro
385                 390                 395                 400

Gly Val Ile Ser Ala Ala Glu Ala Ser Gly Ala Glu Met Ala Thr Thr
                405                 410                 415

Ala Thr Val Met Ala Ser Ala Ile Asn Ser Phe Gly Leu Lys Ala Ser
            420                 425                 430

Asp Ala Asn His Val Ala Asp Leu Leu Ala Arg Ser Ala Asn Asp Ser
        435                 440                 445

Ala Ala Asp Ile Gln Tyr Met Gly Asp Ala Leu Lys Tyr Ala Gly Thr
    450                 455                 460

Pro Ala Lys Ala Leu Gly Val Ser Ile Glu Asp Thr Ser Ala Ala Ile
465                 470                 475                 480

Glu Val Leu Ser Asn Ser Gly Leu Glu Gly Ser Gln Ala Gly Thr Ala
                485                 490                 495

Leu Arg Ala Ser Phe Ile Arg Leu Ala Asn Pro Ser Lys Asn Thr Ala
            500                 505                 510

Lys Glu Met Lys Lys Leu Gly Ile His Leu Ser Asp Ala Lys Gly Gln
        515                 520                 525

Phe Val Gly Met Gly Glu Leu Ile Arg Gln Phe Gln Asp Asn Met Lys
    530                 535                 540

Gly Met Thr Arg Glu Gln Lys Leu Ala Thr Val Ala Thr Ile Val Gly
545                 550                 555                 560

Thr Glu Ala Ala Ser Gly Phe Leu Ala Leu Ile Glu Ala Gly Pro Asp
                565                 570                 575

Lys Ile Asn Ser Tyr Ser Lys Ser Leu Lys Asn Ser Asn Gly Glu Ser
            580                 585                 590

Lys Lys Ala Ala Asp Leu Met Lys Asp Asn Leu Lys Gly Ala Leu Glu
        595                 600                 605

Gln Leu Gly Gly Ala Phe Glu Ser Leu Ala Ile Glu Val Gly Lys Asp
    610                 615                 620

Leu Thr Pro Met Ile Arg Ala Gly Ala Glu Gly Leu Thr Lys Leu Val
625                 630                 635                 640

Asp Gly Phe Thr His Leu Pro Gly Trp Val Arg Lys Ala Ser Val Gly
                645                 650                 655

Leu Ala Leu Phe Gly Ala Ser Ile Gly Pro Ala Val Leu Ala Gly Gly
            660                 665                 670

Leu Leu Ile Arg Ala Val Gly Ser Ala Ala Lys Gly Tyr Ala Ser Leu
        675                 680                 685

Asn Arg Arg Ile Ala Glu Asn Thr Ile Leu Ser Asn Thr Asn Ser Lys
    690                 695                 700

Ala Met Lys Ser Leu Gly Leu Gln Thr Leu Phe Leu Gly Ser Thr Thr
705                 710                 715                 720
```

-continued

```
Gly Lys Thr Ser Lys Gly Phe Lys Gly Leu Ala Gly Ala Met Leu Phe
                725                 730                 735

Asn Leu Lys Pro Ile Asn Val Leu Lys Asn Ser Ala Lys Leu Ala Ile
            740                 745                 750

Leu Pro Phe Lys Leu Leu Lys Asn Gly Leu Gly Leu Ala Ala Lys Ser
        755                 760                 765

Leu Phe Ala Val Ser Gly Gly Ala Arg Phe Ala Gly Val Ala Leu Lys
    770                 775                 780

Phe Leu Thr Gly Pro Ile Gly Ala Thr Ile Thr Ala Ile Thr Ile Ala
785                 790                 795                 800

Tyr Lys Val Phe Lys Thr Ala Tyr Asp Arg Val Glu Trp Phe Arg Asn
                805                 810                 815

Gly Ile Asn Gly Leu Gly Glu Thr Ile Lys Phe Phe Gly Gly Lys Ile
            820                 825                 830

Ile Gly Gly Ala Val Arg Lys Leu Gly Glu Phe Lys Asn Tyr Leu Gly
        835                 840                 845

Ser Ile Gly Lys Ser Phe Lys Glu Lys Phe Ser Lys Asp Met Lys Asp
    850                 855                 860

Gly Tyr Lys Ser Leu Ser Asp Asp Asp Leu Leu Lys Val Gly Val Asn
865                 870                 875                 880

Lys Phe Lys Gly Phe Met Gln Thr Met Gly Thr Ala Ser Lys Lys Ala
                885                 890                 895

Ser Asp Thr Val Lys Val Leu Gly Lys Gly Val Ser Lys Glu Thr Glu
            900                 905                 910

Lys Ala Leu Glu Lys Tyr Val His Tyr Ser Glu Glu Asn Asn Arg Ile
        915                 920                 925

Met Glu Lys Val Arg Leu Asn Ser Gly Gln Ile Thr Glu Asp Lys Ala
    930                 935                 940

Lys Lys Leu Leu Lys Ile Glu Ala Asp Leu Ser Asn Asn Leu Ile Ala
945                 950                 955                 960

Glu Ile Glu Lys Arg Asn Lys Lys Glu Leu Glu Lys Thr Gln Glu Leu
                965                 970                 975

Ile Asp Lys Tyr Ser Ala Phe Asp Glu Gln Glu Lys Gln Asn Ile Leu
            980                 985                 990

Thr Arg Thr Lys Glu Lys Asn Asp  Leu Arg Ile Lys Lys  Glu Gln Glu
        995                 1000                1005

Leu Asn  Gln Lys Ile Lys Glu  Leu Lys Glu Lys Ala  Leu Ser Asp
    1010                1015                1020

Gly Gln  Ile Ser Glu Asn Glu  Arg Lys Glu Ile Glu  Lys Leu Glu
    1025                1030                1035

Asn Gln  Arg Arg Asp Ile Thr  Val Lys Glu Leu Ser  Lys Thr Glu
    1040                1045                1050

Lys Glu  Gln Glu Arg Ile Leu  Val Arg Met Gln Arg  Asn Arg Asn
    1055                1060                1065

Ser Tyr  Ser Ile Asp Glu Ala  Ser Lys Ala Ile Lys  Glu Ala Glu
    1070                1075                1080

Lys Ala  Arg Lys Ala Lys Lys  Lys Glu Val Asp Lys  Gln Tyr Glu
    1085                1090                1095

Asp Asp  Val Ile Ala Ile Lys  Asn Asn Val Asn Leu  Ser Lys Ser
    1100                1105                1110

Glu Lys  Asp Lys Leu Leu Ala  Ile Ala Asp Gln Arg  His Lys Asp
    1115                1120                1125
```

-continued

Glu Val Arg Lys Ala Lys Ser Lys Lys Asp Ala Val Val Asp Val
    1130                1135                1140

Val Lys Lys Gln Asn Lys Asp Ile Asp Lys Glu Met Asp Leu Ser
    1145                1150                1155

Ser Gly Arg Val Tyr Lys Asn Thr Glu Lys Trp Trp Asn Gly Leu
    1160                1165                1170

Lys Ser Trp Trp Ser Asn Phe Arg Glu Asp Gln Lys Lys Lys Ser
    1175                1180                1185

Asp Lys Tyr Ala Lys Glu Gln Glu Glu Thr Ala Arg Arg Asn Arg
    1190                1195                1200

Glu Asn Ile Lys Lys Trp Phe Gly Asn Ala Trp Asp Gly Val Lys
    1205                1210                1215

Ser Lys Thr Gly Glu Ala Phe Ser Lys Met Gly Arg Asn Ala Asn
    1220                1225                1230

His Phe Gly Gly Glu Met Lys Lys Met Trp Ser Gly Ile Lys Gly
    1235                1240                1245

Ile Pro Ser Lys Leu Ser Ser Gly Trp Ser Ser Ala Lys Ser Ser
    1250                1255                1260

Val Gly Tyr His Thr Lys Ala Ile Ala Asn Ser Thr Gly Lys Trp
    1265                1270                1275

Phe Gly Lys Ala Trp Gln Ser Val Lys Ser Thr Thr Gly Ser Ile
    1280                1285                1290

Tyr Asn Gln Thr Lys Gln Lys Tyr Ser Asp Ala Ser Asp Lys Ala
    1295                1300                1305

Trp Ala His Ser Lys Ser Ile Trp Lys Gly Thr Ser Lys Trp Phe
    1310                1315                1320

Ser Asn Ala Tyr Lys Ser Ala Lys Gly Trp Leu Thr Asp Met Ala
    1325                1330                1335

Asn Lys Ser Arg Ser Lys Trp Asp Asn Ile Ser Ser Thr Ala Trp
    1340                1345                1350

Ser Asn Ala Lys Ser Val Trp Lys Gly Thr Ser Lys Trp Phe Ser
    1355                1360                1365

Asn Ser Tyr Lys Ser Leu Lys Gly Trp Thr Gly Asp Met Tyr Ser
    1370                1375                1380

Arg Ala His Asp Arg Phe Asp Ala Ile Ser Ser Ser Ala Trp Ser
    1385                1390                1395

Asn Ala Lys Ser Val Phe Asn Gly Phe Arg Lys Trp Leu Ser Arg
    1400                1405                1410

Thr Tyr Glu Trp Ile Arg Asp Ile Gly Lys Asp Met Gly Arg Ala
    1415                1420                1425

Ala Ala Asp Leu Gly Lys Asn Val Ala Asn Lys Ala Ile Gly Gly
    1430                1435                1440

Leu Asn Ser Met Ile Gly Gly Ile Asn Lys Ile Ser Lys Ala Ile
    1445                1450                1455

Thr Asp Lys Asn Leu Ile Lys Pro Ile Pro Thr Leu Ser Thr Gly
    1460                1465                1470

Thr Leu Ala Gly Lys Gly Val Ala Thr Asp Asn Ser Gly Ala Leu
    1475                1480                1485

Thr Gln Pro Thr Phe Ala Val Leu Asn Asp Arg Gly Ser Gly Asn
    1490                1495                1500

Ala Pro Gly Gly Gly Val Gln Glu Val Ile His Arg Ala Asp Gly
    1505                1510                1515

Thr Phe His Ala Pro Gln Gly Arg Asp Val Val Val Pro Leu Gly

-continued

```
    1520                1525                1530

Val Gly  Asp Ser Val Ile Asn  Ala Asn Asp Thr Leu  Lys Leu Gln
    1535                1540                1545

Arg Met  Gly Val Leu Pro Lys  Phe His Gly Gly Thr  Lys Lys Lys
    1550                1555                1560

Lys Trp  Met Glu Gln Val Thr  Glu Asn Leu Gly Lys  Lys Ala Gly
    1565                1570                1575

Asp Phe  Gly Ser Lys Ala Lys  Asn Thr Ala His Asn  Ile Lys Lys
    1580                1585                1590

Gly Ala  Glu Glu Met Val Glu  Ala Ala Gly Asp Lys  Ile Lys Asp
    1595                1600                1605

Gly Ala  Ser Trp Leu Gly Asp  Lys Ile Gly Asp Val  Trp Asp Tyr
    1610                1615                1620

Val Gln  His Pro Gly Lys Leu  Val Asn Lys Val Met  Ser Gly Leu
    1625                1630                1635

Asn Ile  Asn Phe Gly Gly Gly  Ala Asn Ala Thr Val  Lys Ile Ala
    1640                1645                1650

Lys Gly  Ala Tyr Ser Leu Leu  Lys Lys Lys Leu Val  Asp Lys Val
    1655                1660                1665

Lys Ser  Trp Phe Glu Asp Phe  Gly Gly Gly Gly Asp  Gly Ser Tyr
    1670                1675                1680

Leu Phe  Asp His Pro Ile Trp  Gln Arg Phe Gly Ser  Tyr Thr Gly
    1685                1690                1695

Gly Leu  Asn Phe Asn Gly Gly  Arg His Tyr Gly Ile  Asp Phe Gln
    1700                1705                1710

Met Pro  Thr Gly Thr Asn Ile  Tyr Ala Val Lys Gly  Gly Ile Ala
    1715                1720                1725

Asp Lys  Val Trp Thr Asp Tyr  Gly Gly Gly Asn Ser  Ile Gln Ile
    1730                1735                1740

Lys Thr  Gly Ala Asn Glu Trp  Asn Trp Tyr Met His  Leu Ser Lys
    1745                1750                1755

Gln Leu  Ala Arg Gln Gly Gln  Arg Ile Lys Ala Gly  Gln Leu Ile
    1760                1765                1770

Gly Lys  Ser Gly Ala Thr Gly  Asn Phe Val Arg Gly  Ala His Leu
    1775                1780                1785

His Phe  Gln Leu Met Gln Gly  Ser His Pro Gly Asn  Asp Thr Ala
    1790                1795                1800

Lys Asp  Pro Glu Lys Trp Leu  Lys Ser Leu Lys Gly  Ser Gly Val
    1805                1810                1815

Arg Ser  Gly Ser Gly Val Asn  Lys Ala Ala Ser Ala  Trp Ala Gly
    1820                1825                1830

Asp Ile  Arg Arg Ala Ala Lys  Arg Met Gly Val Asn  Val Thr Ser
    1835                1840                1845

Gly Asp  Val Gly Asn Ile Ile  Ser Leu Ile Gln His  Glu Ser Gly
    1850                1855                1860

Gly Asn  Ala Gly Ile Thr Gln  Ser Ser Ala Leu Arg  Asp Ile Asn
    1865                1870                1875

Val Leu  Gln Gly Asn Pro Ala  Lys Gly Leu Leu Gln  Tyr Ile Pro
    1880                1885                1890

Gln Thr  Phe Arg His Tyr Ala  Val Arg Gly His Asn  Asn Ile Tyr
    1895                1900                1905

Ser Gly  Tyr Asp Gln Leu Leu  Ala Phe Phe Asn Asn  Ser Tyr Trp
    1910                1915                1920
```

```
Arg Ser  Gln Phe Asn Pro Arg  Gly Gly Trp Ser Pro  Ser Gly Pro
    1925                 1930                 1935

Arg Arg  Tyr Ala Asn Gly Gly  Leu Ile Thr Lys His  Gln Leu Ala
    1940                 1945                 1950

Glu Val  Gly Glu Gly Asp Lys  Gln Glu Met Val Ile  Pro Leu Thr
    1955                 1960                 1965

Arg Arg  Lys Arg Ala Ile Gln  Leu Thr Glu Gln Val  Met Arg Ile
    1970                 1975                 1980

Ile Gly  Met Asp Gly Lys Pro  Asn Asn Ile Thr Val  Asn Asn Asp
    1985                 1990                 1995

Thr Ser  Thr Val Glu Lys Leu  Leu Lys Gln Ile Val  Met Leu Ser
    2000                 2005                 2010

Asp Lys  Gly Asn Lys Leu Thr  Asp Ala Leu Ile Gln  Thr Val Ser
    2015                 2020                 2025

Ser Gln  Asp Asn Asn Leu Gly  Ser Asn Asp Ala Ile  Arg Gly Leu
    2030                 2035                 2040

Glu Lys  Ile Leu Ser Lys Gln  Ser Gly His Arg Ala  Asn Ala Asn
    2045                 2050                 2055

Asn Tyr  Met Gly Gly Leu Thr  Asn
    2060                 2065


<210> SEQ ID NO 6
<211> LENGTH: 609
<212> TYPE: PRT
<213> ORGANISM: Staphylococcus aureus

<400> SEQUENCE: 6

Met Lys Lys Gln Ile Ile Ser Leu Gly Ala Leu Ala Val Ala Ser Ser
1               5                   10                  15

Leu Phe Thr Trp Asp Asn Lys Ala Asp Ala Ile Val Thr Lys Asp Tyr
            20                  25                  30

Ser Lys Glu Ser Arg Val Asn Glu Asn Ser Lys Tyr Asp Thr Pro Ile
        35                  40                  45

Pro Asp Trp Tyr Leu Gly Ser Ile Leu Asn Arg Leu Gly Asp Gln Ile
    50                  55                  60

Tyr Tyr Ala Lys Glu Leu Thr Asn Lys Tyr Glu Tyr Gly Glu Lys Glu
65                  70                  75                  80

Tyr Lys Gln Ala Ile Asp Lys Leu Met Thr Arg Val Leu Gly Glu Asp
                85                  90                  95

His Tyr Leu Leu Glu Lys Lys Lys Ala Gln Tyr Glu Ala Tyr Lys Lys
            100                 105                 110

Trp Phe Glu Lys His Lys Ser Glu Asn Pro His Ser Ser Leu Lys Lys
        115                 120                 125

Ile Lys Phe Asp Asp Phe Asp Leu Tyr Arg Leu Thr Lys Lys Glu Tyr
    130                 135                 140

Asn Glu Leu His Gln Ser Leu Lys Glu Ala Val Asp Glu Phe Asn Ser
145                 150                 155                 160

Glu Val Lys Asn Ile Gln Ser Lys Gln Lys Asp Leu Leu Pro Tyr Asp
                165                 170                 175

Glu Ala Thr Glu Asn Arg Val Thr Asn Gly Ile Tyr Asp Phe Val Cys
            180                 185                 190

Glu Ile Asp Thr Leu Tyr Ala Ala Tyr Phe Asn His Ser Gln Tyr Gly
        195                 200                 205

His Asn Ala Lys Glu Leu Arg Ala Lys Leu Asp Ile Ile Leu Gly Asp
```

```
    210                 215                 220

Ala Lys Asp Pro Val Arg Ile Thr Asn Glu Arg Ile Arg Lys Glu Met
225                 230                 235                 240

Met Asp Asp Leu Asn Ser Ile Ile Asp Asp Phe Phe Met Asp Thr Asn
                245                 250                 255

Met Asn Arg Pro Leu Asn Ile Thr Lys Phe Asn Pro Asn Ile His Asp
            260                 265                 270

Tyr Thr Asn Lys Pro Glu Asn Arg Asp Asn Phe Asp Lys Leu Val Lys
        275                 280                 285

Glu Thr Arg Glu Ala Ile Ala Asn Ala Asp Glu Ser Trp Lys Thr Arg
    290                 295                 300

Thr Val Lys Asn Tyr Gly Glu Ser Glu Thr Lys Ser Pro Val Val Lys
305                 310                 315                 320

Glu Glu Lys Lys Val Glu Glu Pro Gln Leu Pro Lys Val Gly Asn Gln
                325                 330                 335

Gln Glu Asp Lys Ile Thr Val Gly Thr Thr Glu Glu Ala Pro Leu Pro
            340                 345                 350

Ile Ala Gln Pro Leu Val Lys Ile Pro Gln Gly Thr Ile Gln Gly Glu
        355                 360                 365

Ile Val Lys Gly Pro Glu Tyr Leu Thr Met Glu Asn Lys Thr Leu Gln
    370                 375                 380

Gly Glu Ile Val Gln Gly Pro Asp Phe Pro Thr Met Glu Gln Asn Arg
385                 390                 395                 400

Pro Ser Leu Ser Asp Asn Tyr Thr Gln Pro Thr Thr Pro Asn Pro Ile
                405                 410                 415

Leu Lys Gly Ile Glu Gly Asn Ser Thr Lys Leu Glu Ile Lys Pro Gln
            420                 425                 430

Gly Thr Glu Ser Thr Leu Lys Gly Thr Gln Gly Glu Ser Ser Asp Ile
        435                 440                 445

Glu Val Lys Pro Gln Ala Thr Glu Thr Thr Glu Ala Ser His Tyr Pro
    450                 455                 460

Ala Arg Pro Gln Phe Asn Lys Thr Pro Lys Tyr Val Lys Tyr Arg Asp
465                 470                 475                 480

Ala Gly Thr Gly Ile Arg Glu Tyr Asn Asp Gly Thr Phe Gly Tyr Glu
                485                 490                 495

Ala Arg Pro Arg Phe Asn Lys Pro Ser Glu Thr Asn Ala Tyr Asn Val
            500                 505                 510

Thr Thr Asn Gln Asp Gly Thr Val Ser Tyr Gly Ala Arg Pro Thr Gln
        515                 520                 525

Asn Lys Pro Ser Glu Thr Asn Ala Tyr Asn Val Thr Thr His Ala Asn
    530                 535                 540

Gly Gln Val Ser Tyr Gly Ala Arg Pro Thr Gln Asn Lys Pro Ser Glu
545                 550                 555                 560

Thr Asn Ala Tyr Asn Val Thr Thr His Ala Asn Gly Gln Val Ser Tyr
                565                 570                 575

Gly Ala Arg Pro Thr Gln Asn Lys Pro Ser Lys Thr Asn Ala Tyr Asn
            580                 585                 590

Val Thr Thr His Ala Asp Gly Thr Ala Thr Tyr Gly Pro Arg Val Thr
        595                 600                 605

Lys

<210> SEQ ID NO 7
<211> LENGTH: 144
```

<212> TYPE: PRT
<213> ORGANISM: Staphylococcus aureus

<400> SEQUENCE: 7

Met Lys Lys Val Ile Gly Leu Leu Leu Val Ser Thr Leu Ala Leu Thr
1               5                   10                  15

Ala Cys Gly Glu Lys Glu Lys Pro Lys Lys Glu Glu Asn Lys Lys Ser
            20                  25                  30

Gln Thr Gln Lys His Lys Asp Ser Lys Pro Lys Thr Gln Gln Glu Lys
        35                  40                  45

Met Lys Lys Val Glu Asp Lys Asn Pro Pro Asn Asn Ser Ile Gln Asn
    50                  55                  60

Asn Ser Asn Asn Gln Asn Gln Ser Gln Asn Asn Gln Leu Asn Asn Asn
65                  70                  75                  80

Ser Asp Pro Ser Asn Asn Thr Pro Ala Asn Ile Asn Lys Asn Asp Ser
                85                  90                  95

Gln Asn Thr Asn Leu Asn Asp Glu Tyr Val Val Ser Pro Gly Trp Thr
            100                 105                 110

Lys Asp Glu Gln Ala Lys Ala Phe Glu Glu Tyr Lys Lys Gly Lys Glu
        115                 120                 125

Asp Glu Ala Arg Ala Gly Ala Ser Ala Val Pro Gly Ala Asn Ile Asn
    130                 135                 140

<210> SEQ ID NO 8
<211> LENGTH: 1257
<212> TYPE: PRT
<213> ORGANISM: Staphylococcus aureus

<400> SEQUENCE: 8

Met Ala Lys Lys Phe Asn Tyr Lys Leu Pro Ser Met Val Ala Leu Thr
1               5                   10                  15

Leu Val Gly Ser Ala Val Thr Ala His Gln Val Gln Ala Ala Glu Thr
            20                  25                  30

Thr Gln Asp Gln Thr Thr Asn Lys Asn Val Leu Asp Ser Asn Lys Val
        35                  40                  45

Lys Ala Thr Thr Glu Gln Ala Lys Ala Glu Val Lys Asn Pro Thr Gln
    50                  55                  60

Asn Ile Ser Gly Thr Gln Val Tyr Gln Asp Pro Ala Ile Val Gln Pro
65                  70                  75                  80

Lys Ala Ala Asn Lys Thr Gly Asn Ala Gln Val Asn Gln Lys Val Asp
                85                  90                  95

Thr Thr Gln Val Asn Gly Asp Thr Arg Ala Thr Gln Ser Thr Thr Ser
            100                 105                 110

Asn Asn Ala Lys Pro Val Thr Lys Ser Thr Asn Thr Thr Ala Pro Lys
        115                 120                 125

Thr Asn Asn Asn Val Thr Ser Ala Gly Tyr Ser Leu Val Asp Asp Glu
    130                 135                 140

Asp Asp Asn Ser Glu Asn Gln Ile Asn Pro Glu Leu Ile Lys Ser Ala
145                 150                 155                 160

Ala Lys Pro Ala Ala Leu Glu Thr Gln Tyr Lys Ala Ala Ala Pro Lys
                165                 170                 175

Ala Thr Pro Val Ala Pro Lys Ala Lys Thr Glu Ala Thr Pro Lys Val
            180                 185                 190

Thr Thr Phe Ser Ala Ser Ala Gln Pro Arg Ser Ala Ala Ala Ala Pro
        195                 200                 205

-continued

```
Lys Thr Ser Leu Pro Lys Tyr Lys Pro Gln Val Asn Ser Ser Ile Asn
    210                 215                 220

Asp Tyr Ile Arg Lys Asn Asn Leu Lys Ala Pro Lys Ile Glu Glu Asp
225                 230                 235                 240

Tyr Thr Ser Tyr Phe Pro Lys Tyr Ala Tyr Arg Asn Gly Val Gly Arg
                245                 250                 255

Pro Glu Gly Ile Val Val His Asp Thr Ala Asn Asp Arg Ser Thr Ile
            260                 265                 270

Asn Gly Glu Ile Ser Tyr Met Lys Asn Asn Tyr Gln Asn Ala Phe Val
        275                 280                 285

His Ala Phe Val Asp Gly Asp Arg Ile Ile Glu Thr Ala Pro Thr Asp
    290                 295                 300

Tyr Leu Ser Trp Gly Val Gly Ala Val Gly Asn Pro Arg Phe Ile Asn
305                 310                 315                 320

Val Glu Ile Val His Thr His Asp Tyr Ala Ser Phe Ala Arg Ser Met
                325                 330                 335

Asn Asn Tyr Ala Asp Tyr Ala Ala Thr Gln Leu Gln Tyr Tyr Gly Leu
            340                 345                 350

Lys Pro Asp Ser Ala Glu Tyr Asp Gly Asn Gly Thr Val Trp Thr His
        355                 360                 365

Tyr Ala Val Ser Lys Tyr Leu Gly Gly Thr Asp His Ala Asp Pro His
    370                 375                 380

Gly Tyr Leu Arg Ser His Asn Tyr Ser Tyr Asp Gln Leu Tyr Asp Leu
385                 390                 395                 400

Ile Asn Glu Lys Tyr Leu Ile Lys Met Gly Lys Val Ala Pro Trp Gly
                405                 410                 415

Thr Gln Ser Thr Thr Thr Pro Thr Thr Pro Ser Lys Pro Ser Thr Pro
            420                 425                 430

Ser Lys Pro Ser Thr Pro Ser Thr Gly Lys Leu Thr Val Ala Ala Asn
        435                 440                 445

Asn Gly Val Ala Gln Ile Lys Pro Thr Asn Ser Gly Leu Tyr Thr Thr
    450                 455                 460

Val Tyr Asp Lys Thr Gly Lys Ala Thr Asn Glu Val Gln Lys Thr Phe
465                 470                 475                 480

Ala Val Ser Lys Thr Ala Thr Leu Gly Asn Gln Lys Phe Tyr Leu Val
                485                 490                 495

Gln Asp Tyr Asn Ser Gly Asn Lys Phe Gly Trp Val Lys Glu Gly Asp
            500                 505                 510

Val Val Tyr Asn Thr Ala Lys Ser Pro Val Asn Val Asn Gln Ser Tyr
        515                 520                 525

Ser Ile Lys Pro Gly Thr Lys Leu Tyr Thr Val Pro Trp Gly Thr Ser
    530                 535                 540

Lys Gln Val Ala Gly Ser Val Ser Gly Ser Gly Asn Gln Thr Phe Lys
545                 550                 555                 560

Ala Ser Lys Gln Gln Gln Ile Asp Lys Ser Ile Tyr Leu Tyr Gly Ser
                565                 570                 575

Val Asn Gly Lys Ser Gly Trp Val Ser Lys Ala Tyr Leu Val Asp Thr
            580                 585                 590

Ala Lys Pro Thr Pro Thr Pro Thr Pro Lys Pro Ser Thr Pro Thr Thr
        595                 600                 605

Asn Asn Lys Leu Thr Val Ser Ser Leu Asn Gly Val Ala Gln Ile Asn
    610                 615                 620

Ala Lys Asn Asn Gly Leu Phe Thr Thr Val Tyr Asp Lys Thr Gly Lys
```

-continued

```
625                 630                 635                 640

Pro Thr Lys Glu Val Gln Lys Thr Phe Ala Val Thr Lys Glu Ala Ser
                645                 650                 655

Leu Gly Gly Asn Lys Phe Tyr Leu Val Lys Asp Tyr Asn Ser Pro Thr
            660                 665                 670

Leu Ile Gly Trp Val Lys Gln Gly Asp Val Ile Tyr Asn Asn Ala Lys
        675                 680                 685

Ser Pro Val Asn Val Met Gln Thr Tyr Thr Val Lys Pro Gly Thr Lys
    690                 695                 700

Leu Tyr Ser Val Pro Trp Gly Thr Tyr Lys Gln Glu Ala Gly Ala Val
705                 710                 715                 720

Ser Gly Thr Gly Asn Gln Thr Phe Lys Ala Thr Lys Gln Gln Gln Ile
                725                 730                 735

Asp Lys Ser Ile Tyr Leu Tyr Gly Thr Val Asn Gly Lys Ser Gly Trp
            740                 745                 750

Ile Ser Lys Ala Tyr Leu Ala Val Pro Ala Ala Pro Lys Lys Ala Val
        755                 760                 765

Ala Gln Pro Lys Thr Ala Val Lys Ala Tyr Ala Val Thr Lys Pro Gln
    770                 775                 780

Thr Thr Gln Thr Val Ser Lys Ile Ala Gln Val Lys Pro Asn Asn Thr
785                 790                 795                 800

Gly Ile Arg Ala Ser Val Tyr Glu Lys Thr Ala Lys Asn Gly Ala Lys
                805                 810                 815

Tyr Ala Asp Arg Thr Phe Tyr Val Thr Lys Glu Arg Ala His Gly Asn
            820                 825                 830

Glu Thr Tyr Val Leu Leu Asn Asn Thr Ser His Asn Ile Pro Leu Gly
        835                 840                 845

Trp Phe Asn Val Lys Asp Leu Asn Val Gln Asn Leu Gly Lys Glu Val
    850                 855                 860

Lys Thr Thr Gln Lys Tyr Thr Val Asn Arg Ser Asn Asn Gly Leu Ser
865                 870                 875                 880

Met Val Pro Trp Gly Thr Lys Asn Gln Val Ile Leu Thr Gly Asn Asn
                885                 890                 895

Ile Ala Gln Gly Thr Phe Asn Ala Thr Lys Gln Val Ser Val Gly Lys
            900                 905                 910

Asp Val Tyr Leu Tyr Gly Thr Ile Asn Asn Arg Thr Gly Trp Val Asn
        915                 920                 925

Ser Lys Asp Leu Thr Ala Pro Thr Ala Val Lys Pro Thr Thr Ser Ala
    930                 935                 940

Ala Lys Asp Tyr Asn Tyr Thr Tyr Val Ile Lys Asn Gly Asn Gly Tyr
945                 950                 955                 960

Tyr Tyr Val Thr Pro Asn Ser Asp Thr Ala Lys Tyr Ser Leu Lys Ala
                965                 970                 975

Phe Asn Glu Gln Pro Phe Ala Val Val Lys Glu Gln Val Ile Asn Gly
            980                 985                 990

Gln Thr Trp Tyr Tyr Gly Lys Leu  Ser Asn Gly Lys Leu  Ala Trp Ile
        995                 1000                 1005

Lys Ser  Thr Asp Leu Ala Lys  Glu Leu Ile Lys Tyr  Asn Gln Ile
    1010                 1015                 1020

Gly Met  Thr Leu Asn Gln Val  Ala Gln Ile Gln Ala  Gly Leu Gln
    1025                 1030                 1035

Tyr Lys  Pro Gln Val Gln Arg  Val Pro Gly Lys Trp  Thr Asp Ala
    1040                 1045                 1050
```

```
Asn Phe  Asn Asp Val Lys His  Ala Met Asp Thr Lys  Arg Leu Ala
    1055                 1060                 1065

Gln Asp  Pro Ala Leu Lys Tyr  Gln Phe Leu Arg Leu  Asp Gln Pro
    1070                 1075                 1080

Gln Asn  Ile Ser Ile Asp Lys  Ile Asn Gln Phe Leu  Lys Gly Lys
    1085                 1090                 1095

Gly Val  Leu Glu Asn Gln Gly  Ala Ala Phe Asn Lys  Ala Ala Gln
    1100                 1105                 1110

Met Tyr  Gly Ile Asn Glu Val  Tyr Leu Ile Ser His  Ala Leu Leu
    1115                 1120                 1125

Glu Thr  Gly Asn Gly Thr Ser  Gln Leu Ala Lys Gly  Ala Asp Val
    1130                 1135                 1140

Val Asn  Asn Lys Val Val Thr  Asn Ser Asn Thr Lys  Tyr His Asn
    1145                 1150                 1155

Val Phe  Gly Ile Ala Ala Tyr  Asp Asn Asp Pro Leu  Arg Glu Gly
    1160                 1165                 1170

Ile Lys  Tyr Ala Lys Gln Ala  Gly Trp Asp Thr Val  Ser Lys Ala
    1175                 1180                 1185

Ile Val  Gly Gly Ala Lys Phe  Ile Gly Asn Ser Tyr  Val Lys Ala
    1190                 1195                 1200

Gly Gln  Asn Thr Leu Tyr Lys  Met Arg Trp Asn Pro  Ala His Pro
    1205                 1210                 1215

Gly Thr  His Gln Tyr Ala Thr  Asp Val Asp Trp Ala  Asn Ile Asn
    1220                 1225                 1230

Ala Lys  Ile Ile Lys Gly Tyr  Tyr Asp Lys Ile Gly  Glu Val Gly
    1235                 1240                 1245

Lys Tyr  Phe Asp Ile Pro Gln  Tyr Lys
    1250                 1255
```

<210> SEQ ID NO 9
<211> LENGTH: 486
<212> TYPE: PRT
<213> ORGANISM: Staphylococcus aureus

<400> SEQUENCE: 9

```
Met Ser Asn Asn Phe Lys Asp Asp Phe Glu Lys Asn Arg Gln Ser Ile
1               5                   10                  15

Asp Thr Asn Ser His Gln Asp His Thr Glu Asp Val Glu Lys Asp Gln
            20                  25                  30

Ser Glu Leu Glu His Gln Asp Thr Ile Glu Asn Thr Glu Gln Gln Phe
        35                  40                  45

Pro Pro Arg Asn Ala Gln Arg Arg Lys Arg Arg Arg Asp Leu Ala Thr
    50                  55                  60

Asn His Asn Lys Gln Val His Asn Glu Ser Gln Thr Ser Glu Asp Asn
65                  70                  75                  80

Val Gln Asn Glu Ala Gly Thr Ile Asp Asp Arg Gln Val Glu Ser Ser
                85                  90                  95

His Ser Thr Glu Ser Gln Glu Pro Ser His Gln Asp Ser Thr Pro Gln
            100                 105                 110

His Glu Glu Gly Tyr Tyr Asn Lys Asn Ala Phe Ala Met Asp Lys Ser
        115                 120                 125

His Pro Glu Pro Ile Glu Asp Asn Asp Lys His Glu Thr Ile Lys Glu
    130                 135                 140

Ala Glu Asn Asn Thr Glu His Ser Thr Val Ser Asp Lys Ser Glu Ala
```

```
145                 150                 155                 160

Glu Gln Ser Gln Gln Pro Lys Pro Tyr Phe Ala Thr Gly Ala Asn Gln
                165                 170                 175

Ala Asn Thr Ser Lys Asp Lys His Asp Asp Val Thr Val Lys Gln Asp
            180                 185                 190

Lys Asp Glu Ser Lys Asp His His Ser Gly Lys Lys Gly Ala Ala Ile
        195                 200                 205

Gly Ala Gly Thr Ala Gly Val Ala Gly Ala Ala Gly Ala Met Gly Val
    210                 215                 220

Ser Lys Ala Lys Lys His Ser Asn Asp Ala Gln Asn Lys Ser Asn Ser
225                 230                 235                 240

Gly Lys Val Asn Asn Ser Thr Glu Asp Lys Ala Ser Glu Asp Lys Ser
                245                 250                 255

Lys Glu His His Asn Gly Lys Lys Gly Ala Ala Ile Gly Ala Gly Thr
            260                 265                 270

Ala Gly Leu Ala Gly Gly Ala Ala Ser Asn Ser Ala Ser Ala Ala Ser
        275                 280                 285

Lys Pro His Ala Ser Asn Asn Ala Ser Gln Asn Asn Asp Glu His Asp
    290                 295                 300

His His Asp Arg Asp Lys Glu Arg Lys Lys Gly Gly Met Ala Lys Val
305                 310                 315                 320

Leu Leu Pro Leu Ile Ala Ala Val Leu Ile Ile Gly Ala Leu Ala Ile
                325                 330                 335

Phe Gly Gly Met Ala Leu Asn Asn His Asn Asn Gly Thr Lys Glu Asn
            340                 345                 350

Lys Ile Ala Asn Thr Asn Lys Asn Asn Ala Asp Glu Ser Lys Asp Lys
        355                 360                 365

Asp Thr Ser Lys Asp Ala Ser Lys Asp Lys Ser Lys Ser Thr Asp Ser
    370                 375                 380

Asp Lys Ser Lys Asp Asp Gln Asp Lys Ala Thr Lys Asp Glu Ser Asp
385                 390                 395                 400

Asn Asp Gln Asn Asn Ala Asn Gln Ala Asn Asn Gln Ala Gln Asn Asn
                405                 410                 415

Gln Asn Gln Gln Gln Ala Asn Gln Asn Gln Gln Gln Gln Gln Gln Arg
            420                 425                 430

Gln Gly Gly Gly Gln Arg His Thr Val Asn Gly Gln Glu Asn Leu Tyr
        435                 440                 445

Arg Ile Ala Ile Gln Tyr Tyr Gly Ser Gly Ser Pro Glu Asn Val Glu
    450                 455                 460

Lys Ile Arg Arg Ala Asn Gly Leu Ser Gly Asn Asn Ile Arg Asn Gly
465                 470                 475                 480

Gln Gln Ile Val Ile Pro
                485


<210> SEQ ID NO 10
<211> LENGTH: 1274
<212> TYPE: PRT
<213> ORGANISM: Staphylococcus aureus

<400> SEQUENCE: 10

Met Ser Trp Phe Asp Lys Leu Phe Gly Glu Asp Asn Asp Ser Asn Asp
1               5                   10                  15

Asp Leu Ile His Arg Lys Lys Lys Arg Arg Gln Glu Ser Gln Asn Ile
            20                  25                  30
```

-continued

```
Asp Asn Asp His Asp Ser Leu Leu Pro Gln Asn Asn Asp Ile Tyr Ser
        35                  40                  45

Arg Pro Arg Gly Lys Phe Arg Phe Pro Met Ser Val Ala Tyr Glu Asn
    50                  55                  60

Glu Asn Val Glu Gln Ser Ala Asp Thr Ile Ser Asp Glu Lys Glu Gln
65                  70                  75                  80

Tyr His Arg Asp Tyr Arg Lys Gln Ser His Asp Ser Arg Ser Gln Lys
                85                  90                  95

Arg His Arg Arg Arg Arg Asn Gln Thr Thr Glu Glu Gln Asn Tyr Ser
            100                 105                 110

Glu Gln Arg Gly Asn Ser Lys Ile Ser Gln Gln Ser Ile Lys Tyr Lys
        115                 120                 125

Asp His Ser His Tyr His Thr Asn Lys Pro Gly Thr Tyr Val Ser Ala
    130                 135                 140

Ile Asn Gly Ile Glu Lys Glu Thr His Lys Ser Lys Thr His Asn Ile
145                 150                 155                 160

Tyr Ser Asn Asn Thr Asn His Arg Ala Lys Asp Ser Thr Thr Asp Tyr
                165                 170                 175

His Lys Glu Ser Phe Lys Thr Ser Glu Val Pro Ser Ala Ile Phe Gly
            180                 185                 190

Thr Met Lys Pro Lys Lys Leu Glu Asn Gly Arg Ile Pro Val Ser Lys
        195                 200                 205

Ser Ser Glu Lys Val Glu Ser Asp Lys Gln Lys Tyr Asp Lys Tyr Val
    210                 215                 220

Ala Lys Thr Gln Thr Ser Gln Asn Lys His Leu Glu Gln Glu Lys Gln
225                 230                 235                 240

Lys Asp Ser Val Val Lys Gln Gly Thr Ala Ser Lys Ser Ser Asp Glu
                245                 250                 255

Asn Val Ser Ser Thr Thr Lys Ser Thr Pro Asn Tyr Ser Lys Val Asp
            260                 265                 270

Asn Thr Ile Lys Ile Glu Asn Ile Tyr Ala Ser Gln Ile Val Glu Glu
        275                 280                 285

Ile Arg Arg Glu Arg Glu Arg Lys Val Leu Gln Lys Arg Arg Phe Lys
    290                 295                 300

Lys Ala Leu Gln Gln Lys Arg Glu Glu His Lys Asn Glu Glu Gln Asp
305                 310                 315                 320

Ala Ile Gln Arg Ala Ile Asp Glu Met Tyr Ala Lys Gln Ala Glu Arg
                325                 330                 335

Tyr Val Gly Asp Ser Ser Leu Asn Asp Asp Ser Asp Leu Thr Asp Asn
            340                 345                 350

Ser Thr Glu Ala Ser Gln Leu His Thr Asn Glu Ile Glu Asp Glu Ala
        355                 360                 365

Val Ser Asn Asp Glu Asn Lys Lys Ala Ser Ile Gln Asn Glu Asp Thr
    370                 375                 380

Asp Asp Thr His Val Asp Glu Ser Pro Tyr Asn Tyr Glu Glu Val Ser
385                 390                 395                 400

Leu Asn Gln Val Ser Thr Thr Lys Gln Leu Ser Asp Asp Glu Val Thr
                405                 410                 415

Val Ser Asp Val Thr Ser Gln Arg Gln Ser Ala Leu Gln His Asn Val
            420                 425                 430

Glu Val Asn Asn Gln Asp Glu Leu Lys Asn Gln Ser Arg Leu Ile Ala
        435                 440                 445

Asp Ser Glu Glu Asp Gly Ala Thr Asn Glu Glu Glu Tyr Ser Gly Ser
```

```
    450                 455                 460

Gln Ile Asp Asp Ala Glu Phe Tyr Glu Leu Asn Asp Thr Glu Val Asp
465                 470                 475                 480

Glu Asp Thr Thr Ser Asn Ser Glu Asp Asn Thr Asn Arg Asp Ala Ser
                485                 490                 495

Glu Met His Val Asp Ala Pro Lys Thr Gln Glu His Ala Val Thr Glu
            500                 505                 510

Ser Gln Val Asn Asn Ile Asp Lys Thr Val Asp Asn Glu Ile Glu Leu
        515                 520                 525

Ala Pro Arg His Lys Lys Asp Asp Gln Thr Asn Leu Ser Val Asn Ser
    530                 535                 540

Leu Lys Thr Asn Asp Val Asn Asp Gly His Val Val Glu Asp Ser Ser
545                 550                 555                 560

Met Asn Glu Ile Glu Lys Gln Asn Ala Glu Ile Thr Glu Asn Val Gln
                565                 570                 575

Asn Glu Ala Ala Glu Ser Lys Gln Asn Val Glu Glu Lys Thr Ile Glu
            580                 585                 590

Asn Val Asn Pro Lys Lys Gln Thr Glu Lys Val Ser Thr Leu Ser Lys
        595                 600                 605

Arg Pro Phe Asn Val Val Met Thr Pro Ser Asp Lys Lys Arg Met Met
    610                 615                 620

Asp Arg Lys Lys His Ser Lys Val Asn Val Pro Glu Leu Lys Pro Val
625                 630                 635                 640

Gln Ser Lys Gln Ala Ala Ser Glu Ser Lys Thr Ala Thr Gln Asn Thr
                645                 650                 655

Pro Ser Ser Ser Thr Asp Ser Gln Glu Ser Asn Thr Asn Ala Tyr Lys
            660                 665                 670

Thr Asn Asn Met Thr Ser Asn Asn Val Glu Asn Asn Gln Leu Ile Gly
        675                 680                 685

His Ala Ala Thr Glu Asn Asp Tyr Gln Asn Ala Gln Gln Tyr Ser Glu
    690                 695                 700

Gln Lys Pro Ser Ala Asp Ser Thr Gln Thr Glu Ile Phe Glu Glu Ser
705                 710                 715                 720

Gln Asp Asp Asn Gln Leu Glu Asn Glu Gln Val Asp Gln Ser Thr Ser
                725                 730                 735

Ser Ser Val Ser Glu Val Ser Asp Ile Thr Glu Glu Ser Glu Glu Thr
            740                 745                 750

Thr His Gln Asn Asn Thr Ser Gly Gln Gln Asp Asn Asp Asp Gln Gln
        755                 760                 765

Lys Asp Leu Gln Leu Ser Phe Ser Asn Gln Asn Glu Asp Thr Ala Asn
    770                 775                 780

Glu Asn Arg Pro Arg Thr Asn Gln Pro Asp Val Ala Thr Asn Gln Ala
785                 790                 795                 800

Val Gln Thr Ser Lys Pro Met Ile Arg Lys Gly Pro Asn Ile Lys Leu
                805                 810                 815

Pro Ser Val Ser Leu Leu Glu Glu Pro Gln Val Ile Glu Pro Asp Glu
            820                 825                 830

Asp Trp Ile Thr Asp Lys Lys Lys Glu Leu Asn Asp Ala Leu Phe Tyr
        835                 840                 845

Phe Asn Val Pro Ala Glu Val Gln Asp Val Thr Glu Gly Pro Ser Val
    850                 855                 860

Thr Arg Phe Glu Leu Ser Val Glu Lys Gly Val Lys Val Ser Arg Ile
865                 870                 875                 880
```

-continued

```
Thr Ala Leu Gln Asp Asp Ile Lys Met Ala Leu Ala Ala Lys Asp Ile
                885                 890                 895

Arg Ile Glu Ala Pro Ile Pro Gly Thr Ser Arg Val Gly Ile Glu Val
            900                 905                 910

Pro Asn Gln Asn Pro Thr Thr Val Asn Leu Arg Ser Ile Ile Glu Ser
        915                 920                 925

Pro Ser Phe Lys Asn Ala Glu Ser Lys Leu Thr Val Ala Met Gly Tyr
    930                 935                 940

Arg Ile Asn Asn Glu Pro Leu Leu Met Asp Ile Ala Lys Thr Pro His
945                 950                 955                 960

Ala Leu Ile Ala Gly Ala Thr Gly Ser Gly Lys Ser Val Cys Ile Asn
                965                 970                 975

Ser Ile Leu Met Ser Leu Leu Tyr Lys Asn His Pro Glu Glu Leu Arg
            980                 985                 990

Leu Leu Leu Ile Asp Pro Lys Met  Val Glu Leu Ala Pro  Tyr Asn Gly
        995                 1000                1005

Leu Pro  His Leu Val Ala Pro  Val Ile Thr Asp Val  Lys Ala Ala
    1010                1015                1020

Thr Gln  Ser Leu Lys Trp Ala  Val Glu Glu Met Glu  Arg Arg Tyr
    1025                1030                1035

Lys Leu  Phe Ala His Tyr His  Val Arg Asn Ile Thr  Ala Phe Asn
    1040                1045                1050

Lys Lys  Ala Pro Tyr Asp Glu  Arg Met Pro Lys Ile  Val Ile Val
    1055                1060                1065

Ile Asp  Glu Leu Ala Asp Leu  Met Met Met Ala Pro  Gln Glu Val
    1070                1075                1080

Glu Gln  Ser Ile Ala Arg Ile  Ala Gln Lys Ala Arg  Ala Cys Gly
    1085                1090                1095

Ile His  Met Leu Val Ala Thr  Gln Arg Pro Ser Val  Asn Val Ile
    1100                1105                1110

Thr Gly  Leu Ile Lys Ala Asn  Ile Pro Thr Arg Ile  Ala Phe Met
    1115                1120                1125

Val Ser  Ser Ser Val Asp Ser  Arg Thr Ile Leu Asp  Ser Gly Gly
    1130                1135                1140

Ala Glu  Arg Leu Leu Gly Tyr  Gly Asp Met Leu Tyr  Leu Gly Ser
    1145                1150                1155

Gly Met  Asn Lys Pro Ile Arg  Val Gln Gly Thr Phe  Val Ser Asp
    1160                1165                1170

Asp Glu  Ile Asp Asp Val Val  Asp Phe Ile Lys Gln  Gln Arg Glu
    1175                1180                1185

Pro Asp  Tyr Leu Phe Glu Glu  Lys Glu Leu Leu Lys  Lys Thr Gln
    1190                1195                1200

Thr Gln  Ser Gln Asp Glu Leu  Phe Asp Asp Val Cys  Ala Phe Met
    1205                1210                1215

Val Asn  Glu Gly His Ile Ser  Thr Ser Leu Ile Gln  Arg His Phe
    1220                1225                1230

Gln Ile  Gly Tyr Asn Arg Ala  Ala Arg Ile Ile Asp  Gln Leu Glu
    1235                1240                1245

Gln Leu  Gly Tyr Val Ser Ser  Ala Asn Gly Ser Lys  Pro Arg Asp
    1250                1255                1260

Val Tyr  Val Thr Glu Ala Asp  Leu Asn Lys Glu
    1265                1270
```

<210> SEQ ID NO 11
<211> LENGTH: 209
<212> TYPE: PRT
<213> ORGANISM: Staphylococcus aureus

<400> SEQUENCE: 11

```
Met Ser Asn Gln Asn Tyr Asp Tyr Asn Lys Asn Glu Asp Gly Ser Lys
1               5                   10                  15

Lys Lys Met Ser Thr Thr Ala Lys Val Val Ser Ile Ala Thr Val Leu
            20                  25                  30

Leu Leu Leu Gly Gly Leu Val Phe Ala Ile Phe Ala Tyr Val Asp His
        35                  40                  45

Ser Asn Lys Ala Lys Glu Arg Met Leu Asn Glu Gln Lys Gln Glu Gln
    50                  55                  60

Lys Glu Lys Arg Gln Lys Glu Asn Ala Glu Lys Glu Arg Lys Lys Lys
65                  70                  75                  80

Gln Gln Glu Glu Lys Glu Gln Asn Glu Leu Asp Ser Gln Ala Asn Gln
                85                  90                  95

Tyr Gln Gln Leu Pro Gln Gln Asn Gln Tyr Gln Tyr Val Pro Pro Gln
            100                 105                 110

Gln Gln Ala Pro Thr Lys Gln Arg Pro Ala Lys Glu Glu Asn Asp Asp
        115                 120                 125

Lys Ala Ser Lys Asp Glu Ser Lys Asp Lys Asp Asp Lys Ala Ser Gln
    130                 135                 140

Asp Lys Ser Asp Asp Asn Gln Lys Lys Thr Asp Asp Asn Lys Gln Pro
145                 150                 155                 160

Ala Gln Pro Lys Pro Gln Pro Gln Gln Pro Thr Pro Lys Pro Asn Asn
                165                 170                 175

Asn Gln Gln Asn Asn Gln Ser Asn Gln Gln Ala Lys Pro Gln Ala Pro
            180                 185                 190

Gln Gln Asn Ser Gln Ser Thr Thr Asn Lys Gln Asn Asn Ala Asn Asp
        195                 200                 205

Lys
```

<210> SEQ ID NO 12
<211> LENGTH: 190
<212> TYPE: PRT
<213> ORGANISM: Staphylococcus aureus

<400> SEQUENCE: 12

```
Met Lys Leu Lys Ser Leu Ala Val Leu Ser Met Ser Ala Val Val Leu
1               5                   10                  15

Thr Ala Cys Gly Asn Asp Thr Pro Lys Asp Glu Thr Lys Ser Thr Glu
            20                  25                  30

Ser Asn Thr Asn Gln Asp Thr Asn Thr Thr Lys Asp Val Ile Ala Leu
        35                  40                  45

Lys Asp Val Lys Thr Ser Pro Glu Asp Ala Val Lys Lys Ala Glu Glu
    50                  55                  60

Thr Tyr Lys Gly Gln Lys Leu Lys Gly Ile Ser Phe Glu Asn Ser Asn
65                  70                  75                  80

Gly Glu Trp Ala Tyr Lys Val Thr Gln Gln Lys Ser Gly Glu Glu Ser
                85                  90                  95

Glu Val Leu Val Asp Asp Lys Asn Lys Lys Val Ile Asn Lys Lys Thr
            100                 105                 110

Glu Lys Glu Asp Thr Val Asn Glu Asn Asp Asn Phe Lys Tyr Ser Asp
```

-continued

```
        115                 120                 125

Ala Ile Asp Tyr Lys Lys Ala Ile Lys Glu Gly Gln Lys Glu Phe Asp
    130                 135                 140

Gly Asp Ile Lys Glu Trp Ser Leu Glu Lys Asp Asp Gly Lys Leu Val
145                 150                 155                 160

Tyr Asn Ile Asp Leu Lys Lys Gly Asn Lys Lys Gln Glu Val Thr Val
                165                 170                 175

Asp Ala Lys Asn Gly Lys Val Leu Lys Ser Glu Gln Asp Gln
            180                 185                 190


<210> SEQ ID NO 13
<211> LENGTH: 1009
<212> TYPE: PRT
<213> ORGANISM: Staphylococcus aureus

<400> SEQUENCE: 13

Met Lys Lys Lys Asn Trp Ile Tyr Ala Leu Ile Val Thr Leu Ile Ile
1               5                   10                  15

Ile Ile Ala Ile Val Ser Met Ile Phe Phe Val Gln Thr Lys Tyr Gly
            20                  25                  30

Asp Gln Ser Glu Lys Gly Ser Gln Ser Val Ser Asn Lys Asn Asn Lys
        35                  40                  45

Ile His Ile Ala Ile Val Asn Glu Asp Gln Pro Thr Thr Tyr Asn Gly
    50                  55                  60

Lys Lys Val Glu Leu Gly Gln Ala Phe Ile Lys Arg Leu Ala Asn Glu
65                  70                  75                  80

Lys Asn Tyr Lys Phe Glu Thr Val Thr Arg Asn Val Ala Glu Ser Gly
                85                  90                  95

Leu Lys Asn Gly Gly Tyr Gln Val Met Ile Val Ile Pro Glu Asn Phe
            100                 105                 110

Ser Lys Leu Ala Met Gln Leu Asp Ala Lys Thr Pro Ser Lys Ile Ser
        115                 120                 125

Leu Gln Tyr Lys Thr Ala Val Gly Gln Lys Glu Glu Val Ala Lys Asn
    130                 135                 140

Thr Glu Lys Val Val Ser Asn Val Leu Asn Asp Phe Asn Lys Asn Leu
145                 150                 155                 160

Val Glu Ile Tyr Leu Thr Ser Ile Ile Asp Asn Leu His Asn Ala Gln
                165                 170                 175

Lys Asn Val Gly Ala Ile Met Thr Arg Glu His Gly Val Asn Ser Lys
            180                 185                 190

Phe Ser Asn Tyr Leu Leu Asn Pro Ile Asn Asp Phe Pro Glu Leu Phe
        195                 200                 205

Thr Asp Thr Leu Val Asn Ser Ile Ser Ala Asn Lys Asp Ile Thr Lys
    210                 215                 220

Trp Phe Gln Thr Tyr Asn Lys Ser Leu Leu Ser Ala Asn Ser Asp Thr
225                 230                 235                 240

Phe Arg Val Asn Thr Asp Tyr Asn Val Ser Thr Leu Ile Glu Lys Gln
                245                 250                 255

Asn Ser Leu Phe Asp Glu His Asn Thr Ala Met Asp Lys Met Leu Gln
            260                 265                 270

Asp Tyr Lys Ser Gln Lys Asp Ser Val Glu Leu Asp Asn Tyr Ile Asn
        275                 280                 285

Ala Leu Lys Gln Met Asp Ser Gln Ile Asp Gln Gln Ser Ser Met Gln
    290                 295                 300
```

-continued

```
Asp Thr Gly Lys Glu Glu Tyr Lys Gln Thr Val Lys Glu Asn Leu Asp
305                 310                 315                 320

Lys Leu Arg Glu Ile Ile Gln Ser Gln Glu Ser Pro Phe Ser Lys Gly
                325                 330                 335

Met Ile Glu Asp Tyr Arg Lys Gln Leu Thr Glu Ser Leu Gln Asp Glu
            340                 345                 350

Leu Ala Asn Asn Lys Asp Leu Gln Asp Ala Leu Asn Ser Ile Lys Met
        355                 360                 365

Asn Asn Ala Gln Phe Ala Glu Asn Leu Glu Lys Gln Leu His Asp Asp
    370                 375                 380

Ile Val Lys Glu Pro Asp Ser Asp Thr Thr Phe Ile Tyr Asn Met Ser
385                 390                 395                 400

Lys Gln Asp Phe Ile Ala Ala Gly Leu Asn Glu Asp Glu Ala Asn Lys
                405                 410                 415

Tyr Glu Ala Ile Val Lys Glu Ala Lys Arg Tyr Lys Asn Glu Tyr Asn
            420                 425                 430

Leu Lys Lys Pro Leu Ala Glu His Ile Asn Leu Thr Asp Tyr Asp Asn
        435                 440                 445

Gln Val Ala Gln Asp Thr Ser Ser Leu Ile Asn Asp Gly Val Lys Val
    450                 455                 460

Gln Arg Thr Glu Thr Ile Lys Ser Asn Asp Ile Asn Gln Leu Thr Val
465                 470                 475                 480

Ala Thr Asp Pro His Phe Asn Phe Glu Gly Asp Ile Lys Ile Asn Gly
                485                 490                 495

Lys Lys Tyr Asp Ile Lys Asp Gln Ser Val Gln Leu Asp Thr Ser Asn
            500                 505                 510

Lys Glu Tyr Lys Val Glu Val Asn Gly Val Ala Lys Leu Lys Lys Asp
        515                 520                 525

Ala Glu Lys Asp Phe Leu Lys Asp Lys Thr Met His Leu Gln Leu Leu
    530                 535                 540

Phe Gly Gln Ala Asn Arg Gln Asp Glu Pro Asn Asp Lys Lys Ala Thr
545                 550                 555                 560

Ser Val Val Asp Val Thr Leu Asn His Asn Leu Asp Gly Arg Leu Ser
                565                 570                 575

Lys Asp Ala Leu Ser Gln Gln Leu Ser Ala Leu Ser Arg Phe Asp Ala
            580                 585                 590

His Tyr Lys Met Tyr Thr Asp Thr Lys Gly Arg Glu Asp Lys Pro Phe
        595                 600                 605

Asp Asn Lys Arg Leu Ile Asp Met Met Val Asp Gln Val Ile Asn Asp
    610                 615                 620

Met Glu Ser Phe Lys Asp Asp Lys Val Ala Val Leu His Gln Ile Asp
625                 630                 635                 640

Ser Met Glu Glu Asn Ser Asp Lys Leu Ile Asp Asp Ile Leu Asn Asn
                645                 650                 655

Lys Lys Asn Thr Thr Lys Asn Lys Glu Asp Ile Ser Lys Leu Ile Asp
            660                 665                 670

Gln Leu Glu Asn Val Lys Lys Thr Phe Ala Glu Glu Pro Gln Glu Pro
        675                 680                 685

Lys Ile Asp Lys Gly Lys Asn Asp Glu Phe Asn Thr Met Ser Ser Asn
    690                 695                 700

Leu Asp Lys Glu Ile Ser Arg Ile Ser Glu Lys Ser Thr Gln Leu Leu
705                 710                 715                 720

Ser Asp Thr Gln Glu Ser Lys Thr Ile Ala Asp Ser Val Ser Gly Gln
```

-continued

```
                725                 730                 735

Leu Asn Gln Leu Asp Asn Asn Val Asn Lys Leu His Ala Thr Gly Arg
            740                 745                 750

Ala Leu Gly Val Arg Ala Asn Asp Leu Asn Arg Gln Met Ala Lys Asn
        755                 760                 765

Asp Lys Asp Asn Glu Leu Phe Ala Lys Glu Phe Lys Lys Val Leu Gln
    770                 775                 780

Asn Ser Lys Asp Gly Asp Arg Gln Asn Gln Ala Leu Lys Ala Phe Met
785                 790                 795                 800

Ser Asn Pro Val Gln Lys Lys Asn Leu Glu Asn Val Leu Ala Asn Asn
                805                 810                 815

Gly Asn Thr Asp Val Ile Ser Pro Thr Leu Phe Val Leu Leu Met Tyr
            820                 825                 830

Leu Leu Ser Met Ile Thr Ala Tyr Ile Phe Tyr Ser Tyr Glu Arg Ala
        835                 840                 845

Lys Gly Gln Met Asn Phe Ile Lys Asp Asp Tyr Ser Ser Lys Asn Asn
    850                 855                 860

Leu Trp Asn Asn Ala Ile Thr Ser Gly Val Ile Gly Ala Thr Gly Leu
865                 870                 875                 880

Val Glu Gly Leu Ile Val Gly Leu Ile Ala Met Asn Lys Phe His Val
                885                 890                 895

Leu Ala Gly Tyr Arg Ala Lys Phe Ile Leu Met Val Ile Leu Thr Met
            900                 905                 910

Met Val Phe Val Leu Ile Asn Thr Tyr Leu Leu Arg Gln Val Lys Ser
        915                 920                 925

Ile Gly Met Phe Leu Met Ile Ala Ala Leu Gly Leu Tyr Phe Val Ala
    930                 935                 940

Met Asn Asn Leu Lys Ala Ala Gly Gln Gly Val Thr Asn Lys Ile Ser
945                 950                 955                 960

Pro Leu Ser Tyr Ile Asp Asn Met Phe Phe Asn Tyr Leu Asn Ala Glu
                965                 970                 975

His Pro Ile Gly Leu Ala Leu Val Ile Leu Thr Val Leu Val Ile Ile
            980                 985                 990

Gly Phe Val Leu Asn Met Phe Ile  Lys His Phe Lys Lys  Glu Arg Leu
        995                 1000                1005

Ile


<210> SEQ ID NO 14
<211> LENGTH: 396
<212> TYPE: PRT
<213> ORGANISM: Staphylococcus aureus

<400> SEQUENCE: 14

Met Thr Gln Gln Gln Asn Asn Lys Arg Thr Leu Lys Asn Lys His Thr
1               5                   10                  15

Tyr Gln Asn Glu Pro Leu Pro Asn Arg Lys Asp Phe Val Val Ser Phe
            20                  25                  30

Ile Thr Gly Ala Leu Val Gly Ser Ala Leu Gly Leu Tyr Phe Lys Asn
        35                  40                  45

Lys Val Tyr Gln Lys Ala Asp Asp Leu Lys Val Lys Glu Gln Glu Leu
    50                  55                  60

Ser Gln Lys Phe Glu Glu Arg Lys Thr Gln Leu Glu Glu Thr Val Ala
65                  70                  75                  80

Phe Thr Lys Glu Arg Val Glu Gly Phe Leu Asn Lys Ser Lys Asn Glu
```

```
                85                  90                  95

Gln Ala Ala Leu Lys Ala Gln Gln Ala Ala Ile Lys Glu Glu Ala Ser
            100                 105                 110

Ala Asn Asn Leu Ser Asp Thr Ser Gln Glu Ala Gln Glu Ile Gln Glu
        115                 120                 125

Ala Lys Arg Glu Ala Gln Thr Glu Thr Asp Lys Ser Ala Ala Val Ser
    130                 135                 140

Asn Glu Glu Ser Lys Ala Ser Ala Leu Lys Ala Gln Gln Ala Ala Ile
145                 150                 155                 160

Lys Glu Glu Ala Ser Ala Asn Asn Leu Ser Asp Thr Ser Gln Glu Ala
                165                 170                 175

Gln Ala Ile Gln Glu Val Lys Lys Glu Ala Gln Ala Glu Thr Asp Lys
            180                 185                 190

Ser Ala Asp Val Ser Asn Glu Glu Ser Lys Ala Ser Thr Leu Asn Val
        195                 200                 205

Ser Lys Glu Glu Ser Gln Ala Glu Arg Leu Ala Asn Ala Ala Lys Gln
    210                 215                 220

Lys Gln Ala Lys Leu Thr Pro Gly Ser Lys Glu Ser Gln Leu Thr Glu
225                 230                 235                 240

Ala Leu Phe Ala Glu Lys Pro Val Ala Lys Asn Asp Leu Lys Glu Ile
                245                 250                 255

Pro Leu Leu Val Thr Lys Lys Asn Asp Val Ser Glu Thr Val Asn Thr
            260                 265                 270

Asp Asn Lys Asp Thr Val Lys Gln Lys Glu Ala Lys Phe Glu Asn Gly
        275                 280                 285

Val Ile Thr Arg Lys Ala Asp Glu Lys Thr Pro Asn Asn Thr Ala Val
    290                 295                 300

Asp Lys Lys Ser Gly Lys Gln Ser Lys Lys Thr Thr Pro Ser Asn Lys
305                 310                 315                 320

Arg Asn Ala Ser Lys Ala Ser Thr Asn Lys Thr Ser Gly Gln Lys Lys
                325                 330                 335

Gln His Asn Lys Lys Ala Ser Gln Gly Ala Lys Lys Gln Ser Ser Ser
            340                 345                 350

Ser Asn Ser Thr Thr Lys Thr Asn Gln Lys Asn Ser Lys Ala Thr Asn
        355                 360                 365

Ala Lys Ser Ser Asn Ala Ser Lys Lys Ser Asn Ala Lys Val Glu Lys
    370                 375                 380

Ala Lys Ser Lys Ile Glu Lys Arg Thr Phe Asn Asp
385                 390                 395


<210> SEQ ID NO 15
<211> LENGTH: 769
<212> TYPE: PRT
<213> ORGANISM: Staphylococcus aureus

<400> SEQUENCE: 15

Met Asp Ile Gly Lys Lys His Val Ile Pro Lys Ser Gln Tyr Arg Arg
1               5                   10                  15

Lys Arg Arg Glu Phe Phe His Asn Glu Asp Arg Glu Glu Asn Leu Asn
            20                  25                  30

Gln His Gln Asp Lys Gln Asn Ile Asp Asn Thr Thr Ser Lys Lys Ala
        35                  40                  45

Asp Lys Gln Ile His Lys Asp Ser Ile Asp Lys His Glu Arg Phe Lys
    50                  55                  60
```

-continued

```
Asn Ser Leu Ser Ser His Leu Glu Gln Arg Asn Arg Asp Val Asn Glu
65                  70                  75                  80

Asn Lys Ala Glu Glu Ser Lys Ser Asn Gln Gly Ser Lys Ser Ala Tyr
                85                  90                  95

Asn Lys Asp His Tyr Leu Thr Asp Asp Val Ser Lys Lys Gln Asn Ser
            100                 105                 110

Leu Asp Ser Val Asp Gln Asp Thr Glu Lys Ser Lys Tyr Tyr Glu Gln
        115                 120                 125

Asn Thr Glu Ala Thr Leu Ser Thr Asn Ser Thr Asp Lys Val Glu Ser
    130                 135                 140

Thr Asp Met Arg Lys Leu Ser Ser Asp Lys Asn Lys Val Gly His Glu
145                 150                 155                 160

Glu Gln His Val Leu Ser Lys Pro Ser Glu His Asp Lys Glu Thr Arg
                165                 170                 175

Ile Asp Phe Glu Ser Ser Arg Thr Asp Ser Asp Ser Ser Met Gln Thr
            180                 185                 190

Glu Lys Ile Lys Lys Asp Ser Ser Asp Gly Asn Lys Ser Ser Asn Leu
        195                 200                 205

Lys Ser Glu Val Ile Ser Asp Lys Ser Asn Ser Val Pro Ile Leu Ser
    210                 215                 220

Glu Ser Asp Asp Glu Val Asn Asn Gln Lys Pro Leu Thr Leu Pro Glu
225                 230                 235                 240

Glu Gln Lys Leu Lys Arg Gln Gln Ser Gln Asn Glu Gln Thr Lys Thr
                245                 250                 255

Tyr Thr Tyr Gly Asp Ser Glu Gln Asn Asp Lys Ser Asn His Glu Asn
            260                 265                 270

Asp Leu Ser His His Thr Pro Ser Ile Ser Asp Asp Lys Asp Tyr Val
        275                 280                 285

Met Arg Glu Asp His Ile Val Asp Asp Asn Pro Asp Asn Asp Ile Asn
    290                 295                 300

Thr Pro Ser Leu Ser Lys Ile Asp Asp Asp Arg Lys Leu Asp Glu Lys
305                 310                 315                 320

Ile His Val Glu Asp Lys His Lys Gln Asn Ala Asp Ser Ser Glu Thr
                325                 330                 335

Val Gly Tyr Gln Ser Gln Ser Ser Ala Ser His Arg Ser Thr Glu Lys
            340                 345                 350

Arg Asn Met Ala Ile Asn Asp His Asp Lys Leu Asn Gly Gln Lys Pro
        355                 360                 365

Asn Thr Lys Thr Ser Ala Asn Asn Asn Gln Lys Lys Ala Thr Ser Lys
    370                 375                 380

Leu Asn Lys Gly Arg Ala Thr Asn Asn Asn Tyr Ser Ala Ile Leu Lys
385                 390                 395                 400

Lys Phe Trp Met Met Tyr Trp Pro Lys Leu Val Ile Leu Met Gly Ile
                405                 410                 415

Ile Ile Leu Ile Val Ile Leu Asn Ala Ile Phe Asn Asn Val Asn Lys
            420                 425                 430

Asn Asp Arg Met Asn Asp Asn Asn Asp Ala Asp Ala Gln Lys Tyr Thr
        435                 440                 445

Thr Thr Met Lys Asn Ala Asn Asn Ala Val Lys Ser Val Val Thr Val
    450                 455                 460

Glu Asn Glu Thr Ser Lys Asp Ser Ser Leu Pro Lys Asp Lys Ala Ser
465                 470                 475                 480

Gln Asp Glu Val Gly Ser Gly Val Val Tyr Lys Lys Ser Gly Asp Thr
```

```
                485                 490                 495

Leu Tyr Ile Val Thr Asn Ala His Val Val Gly Asp Lys Glu Asn Gln
            500                 505                 510

Lys Ile Thr Phe Ser Asn Asn Lys Ser Val Val Gly Lys Val Leu Gly
        515                 520                 525

Lys Asp Lys Trp Ser Asp Leu Ala Val Val Lys Ala Thr Ser Ser Asp
    530                 535                 540

Ser Ser Val Lys Glu Ile Ala Ile Gly Asp Ser Asn Asn Leu Val Leu
545                 550                 555                 560

Gly Glu Pro Ile Leu Val Val Gly Asn Pro Leu Gly Val Asp Phe Lys
                565                 570                 575

Gly Thr Val Thr Glu Gly Ile Ile Ser Gly Leu Asn Arg Asn Val Pro
            580                 585                 590

Ile Asp Phe Asp Lys Asp Asn Lys Tyr Asp Met Leu Met Lys Ala Phe
        595                 600                 605

Gln Ile Asp Ala Ser Val Asn Pro Gly Asn Ser Gly Gly Ala Val Val
    610                 615                 620

Asn Arg Glu Gly Lys Leu Ile Gly Val Val Ala Ala Lys Ile Ser Met
625                 630                 635                 640

Pro Asn Val Glu Asn Met Ser Phe Ala Ile Pro Val Asn Glu Val Gln
                645                 650                 655

Lys Ile Val Lys Glu Leu Glu Thr Lys Gly Lys Ile Asp Tyr Pro Asp
            660                 665                 670

Val Gly Val Lys Met Lys Asn Ile Ala Ser Leu Asn Ser Phe Glu Arg
        675                 680                 685

Gln Ala Val Lys Leu Leu Gly Lys Val Lys Asn Gly Val Val Val Asp
    690                 695                 700

Gln Val Asp Asn Asn Gly Leu Ala Asp Gln Ser Gly Leu Lys Lys Gly
705                 710                 715                 720

Asp Val Ile Thr Glu Leu Asp Gly Lys Leu Leu Glu Asp Asp Leu Arg
                725                 730                 735

Phe Arg Gln Ile Ile Phe Ser His Lys Asp Asp Leu Lys Ser Ile Thr
            740                 745                 750

Ala Lys Ile Tyr Arg Asp Gly Lys Glu Lys Glu Ile Asn Ile Lys Leu
        755                 760                 765

Lys


<210> SEQ ID NO 16
<211> LENGTH: 208
<212> TYPE: PRT
<213> ORGANISM: Staphylococcus aureus

<400> SEQUENCE: 16

Met Lys Phe Lys Ala Ile Val Ala Ile Thr Leu Ser Leu Ser Leu Leu
1               5                   10                  15

Thr Ala Cys Gly Ala Asn Gln His Lys Glu Asn Ser Ser Lys Ser Asn
            20                  25                  30

Asp Thr Asn Lys Lys Thr Gln Gln Thr Asp Asn Thr Thr Gln Ser Asn
        35                  40                  45

Thr Glu Lys Gln Met Thr Pro Gln Glu Ala Glu Asp Ile Val Arg Asn
    50                  55                  60

Asp Tyr Lys Ala Arg Gly Ala Asn Glu Asn Gln Thr Leu Asn Tyr Lys
65                  70                  75                  80

Thr Asn Leu Glu Arg Ser Asn Glu His Glu Tyr Tyr Val Glu His Leu
```

```
                85                  90                  95

Val Arg Asp Ala Val Gly Thr Pro Leu Lys Arg Cys Ala Ile Val Asn
            100                 105                 110

Arg His Asn Gly Thr Ile Ile Asn Ile Phe Asp Asp Met Ser Glu Lys
        115                 120                 125

Asp Lys Glu Glu Phe Glu Ala Phe Lys Lys Arg Ser Pro Lys Tyr Asn
    130                 135                 140

Pro Gly Met Asn Asp Gln Ala Glu Met Asp Asn Glu Ser Glu Asp Ile
145                 150                 155                 160

Gln His His Asp Ile Asp Asn Asn Lys Ala Ile Gln Asn Asp Leu Pro
                165                 170                 175

Asp Gln Lys Val Asp Asp Lys Asn Asp Lys Asn Ala Val Asn Lys Glu
            180                 185                 190

Glu Lys His Asp Asn Arg Glu Asn Asn Ser Ala Glu Thr Lys Val Lys
        195                 200                 205


<210> SEQ ID NO 17
<211> LENGTH: 227
<212> TYPE: PRT
<213> ORGANISM: Staphylococcus aureus

<400> SEQUENCE: 17

Met Asp Lys Lys Lys Val Ile Lys Phe Met Ile Asn Val Leu Pro Ile
1               5                   10                  15

Val Leu Val Pro Leu Ile Val Glu Arg Lys Arg Ile Lys Gln His Pro
            20                  25                  30

Asp Val Gln Lys Val Thr Asp Ala Thr Ser Lys Val Ala Ser Lys Thr
        35                  40                  45

Ser Ala Ala Ile Ser Asn Thr Ala Ser Asp Val Lys Glu Tyr Val Gly
    50                  55                  60

Asp Lys Lys Gln Asp Phe Glu Asn Lys Arg Glu Leu Lys Lys Phe Ala
65                  70                  75                  80

Arg Glu His Asp Pro Ala Tyr Ile Glu Lys Lys Gly Glu Lys Leu Ala
                85                  90                  95

Lys Gln Asn Arg Lys Asp Ala Asp Lys Met Asn Lys Ile Leu Gln Lys
            100                 105                 110

Asn Ile Glu Lys Arg His Lys Glu Glu Gln Lys Ala Arg Glu Lys Asn
        115                 120                 125

Glu Ile Gln Arg Ile Lys Asp Met Lys Lys Ser Gln Lys Tyr Glu Val
    130                 135                 140

Lys Ala Gly Leu Thr Pro Asn Lys Leu Asp Glu Lys Thr Glu Lys Lys
145                 150                 155                 160

Gly Asp Lys Leu Ala Glu Lys Asn Arg Lys Glu Ile Ala Lys Met Asn
                165                 170                 175

Lys Lys Leu Gln Lys Asn Ile Glu Lys Arg His Lys Glu Glu Gln Lys
            180                 185                 190

Arg Gln Gln Glu Ala Asp Lys Ala Arg Ile Lys Ser Phe Lys Lys Tyr
        195                 200                 205

Lys Asp Tyr Val Ala Lys Ser Ala Ser Gln Gln Asn Lys Glu Asn Asn
    210                 215                 220

Thr Glu Ala
225


<210> SEQ ID NO 18
<211> LENGTH: 404
```

<212> TYPE: PRT
<213> ORGANISM: Staphylococcus aureus

<400> SEQUENCE: 18

```
Met Ser Tyr His Trp Phe Lys Lys Met Leu Leu Ser Thr Ser Met Leu
1               5                   10                  15

Ile Leu Ser Ser Ser Ser Ser Leu Gly Leu Ala Thr His Thr Val Glu
            20                  25                  30

Ala Lys Asp Asn Leu Asn Gly Glu Lys Pro Thr Thr Asn Leu Asn His
        35                  40                  45

Asn Val Thr Ser Pro Ser Val Asn Ser Glu Met Asn Asn Asn Glu Thr
    50                  55                  60

Gly Thr Pro His Glu Ser Asn Gln Ala Gly Asn Glu Gly Thr Gly Ser
65                  70                  75                  80

Asn Ser Arg Asp Ala Asn Pro Asp Ser Asn Asn Val Lys Pro Asp Ser
                85                  90                  95

Asn Asn Gln Asn Pro Ser Pro Asp Ser Lys Pro Asp Pro Asn Asn Pro
            100                 105                 110

Asn Pro Gly Pro Asn Pro Lys Pro Asp Pro Asp Lys Pro Lys Pro Asn
        115                 120                 125

Pro Glu Pro Lys Pro Asp Pro Asp Lys Pro Lys Pro Asn Pro Asp Pro
    130                 135                 140

Lys Pro Asp Pro Asp Lys Pro Lys Pro Asn Pro Asp Pro Lys Pro Asp
145                 150                 155                 160

Pro Asn Pro Asn Pro Asn Pro Lys Pro Asp Pro Asn Lys Pro Asn Pro
                165                 170                 175

Asn Pro Ser Pro Asn Pro Asn Gln Pro Gly Asp Ser Asn Gln Ser Gly
            180                 185                 190

Gly Ser Lys Asn Gly Gly Thr Trp Asn Pro Asn Ala Ser Asp Gly Ser
        195                 200                 205

Asn Gln Gly Gln Trp Gln Pro Asn Gly Asn Gln Gly Asn Ser Gln Asn
    210                 215                 220

Pro Thr Gly Asn Asp Phe Val Ser Gln Arg Phe Leu Ala Leu Ala Asn
225                 230                 235                 240

Gly Ala Tyr Lys Tyr Asn Pro Tyr Ile Leu Asn Gln Ile Asn Gln Leu
                245                 250                 255

Gly Lys Glu Tyr Gly Glu Val Thr Asp Glu Asp Ile Tyr Asn Ile Ile
            260                 265                 270

Arg Lys Gln Asn Phe Ser Gly Asn Ala Tyr Leu Asn Gly Leu Gln Gln
        275                 280                 285

Gln Ser Asn Tyr Phe Arg Phe Gln Tyr Phe Asn Pro Leu Lys Ser Glu
    290                 295                 300

Arg Tyr Tyr Arg Asn Leu Asp Glu Gln Val Leu Ala Leu Ile Thr Gly
305                 310                 315                 320

Glu Ile Gly Ser Met Pro Asp Leu Lys Lys Pro Glu Asp Lys Pro Asp
                325                 330                 335

Ser Lys Gln Arg Ser Phe Glu Pro His Glu Lys Asp Asp Phe Thr Val
            340                 345                 350

Val Lys Lys Gln Glu Asp Asn Lys Lys Ser Ala Ser Thr Ala Tyr Ser
        355                 360                 365

Lys Ser Trp Leu Ala Ile Val Cys Ser Met Met Val Val Phe Ser Ile
    370                 375                 380

Met Leu Phe Leu Phe Val Lys Arg Asn Lys Lys Lys Asn Lys Asn Glu
385                 390                 395                 400
```

Ser Gln Arg Arg

<210> SEQ ID NO 19
<211> LENGTH: 231
<212> TYPE: PRT
<213> ORGANISM: Staphylococcus aureus

<400> SEQUENCE: 19

Met Lys Lys Thr Leu Leu Ala Ser Ser Leu Ala Val Gly Leu Gly Ile
1               5                   10                  15

Val Ala Gly Asn Ala Gly His Glu Ala Gln Ala Ser Glu Ala Asp Leu
            20                  25                  30

Asn Lys Ala Ser Leu Ala Gln Met Ala Gln Ser Asn Asp Gln Thr Leu
        35                  40                  45

Asn Gln Lys Pro Ile Glu Ala Gly Ala Tyr Asn Tyr Thr Phe Asp Tyr
    50                  55                  60

Glu Gly Phe Thr Tyr His Phe Glu Ser Asp Gly Thr His Phe Ala Trp
65                  70                  75                  80

Asn Tyr His Ala Thr Gly Ala Asn Gly Ala Asp Met Ser Ala Gln Ala
                85                  90                  95

Pro Ala Thr Asn Asn Val Ala Pro Ser Ala Asp Gln Ser Asn Gln Val
            100                 105                 110

Gln Ser Gln Glu Val Glu Ala Pro Gln Asn Ala Gln Thr Gln Gln Pro
        115                 120                 125

Gln Ala Ser Thr Ser Asn Asn Ser Gln Val Thr Ala Thr Pro Thr Glu
    130                 135                 140

Ser Lys Ala Ser Glu Gly Ser Ser Val Asn Val Asn Asp His Leu Lys
145                 150                 155                 160

Gln Ile Ala Gln Arg Glu Ser Gly Gly Asn Ile His Ala Val Asn Pro
                165                 170                 175

Thr Ser Gly Ala Ala Gly Lys Tyr Gln Phe Leu Gln Ser Thr Trp Asp
            180                 185                 190

Ser Val Ala Pro Ala Lys Tyr Lys Gly Val Ser Pro Ala Asn Ala Pro
        195                 200                 205

Glu Ser Val Gln Asp Ala Ala Ala Val Lys Leu Tyr Asn Thr Gly Gly
    210                 215                 220

Ala Gly His Trp Val Thr Ala
225                 230

<210> SEQ ID NO 20
<211> LENGTH: 465
<212> TYPE: DNA
<213> ORGANISM: Staphylococcus aureus

<400> SEQUENCE: 20
atgaaaagat tgttaggttt attattagtg agcacgttag tgttaagtgc atgtggaaat 60
gatgagaatc aggaagaatc taaaaaagaa gttaaatcaa aagaaaagaa aattgagaag 120
gaaaaggaaa ataaatcgaa aaaagataag gaaaaagaag ttgcaacaca acaacaacca 180
gacaatcaaa ccgttgaaca accccaatca caagagcaat cggttcaaca accgcaacaa 240
cagataccac aaaatagtgt tcctcagcaa aatgtccaag ttcaacaaaa caaaaagcaa 300
aaagttgatt taaataatat gcctcccact gatttttcta cagagggtat gtctgagcag 360
gctcaaaaac aaattgaaga gctttcaatg caaaaagact atcatggtct gtcacaaaga 420
gaatacaatg atagagtttc tgaaattata aataatgata attga 465

<210> SEQ ID NO 21
<211> LENGTH: 555
<212> TYPE: DNA
<213> ORGANISM: Staphylococcus aureus

<400> SEQUENCE: 21
atgttaaaag gatgcggcgg ttgccttatt tcttttatta tattaattat cttattatca 60
gcctgttcaa tgatgtttag taataatgac aattccacta gtaatcaatc atcaaaaacg 120
caattaactc aaaaagacga agataaaagt gaaaatatgc ctgaagaaaa atcagaatca 180
gaaacagata aggatttaca atcaaccgaa gaagtacccg caaatgaaaa tactgaaaat 240
aatcaacatg aaattgatga aataacaaca acagatcaat cagatgatga aattaacaca 300
ccaaacgttg cagaagaaga atcacaagat gacttgaaag atgatttaaa agaaaagcaa 360
caaccaagtg accatcatca atccacgcaa cctaagactt caccatcaac tgaaacaaac 420
aagcaacaat catttgctaa ttgtaagcaa cttagacaag tatatccgaa tggtgtcact 480
gccgatcatc cagcatatcg accacattta gatagagata aagataaacg tgcatgtgaa 540
cctgataaat attaa 555

<210> SEQ ID NO 22
<211> LENGTH: 390
<212> TYPE: DNA
<213> ORGANISM: Staphylococcus aureus

<400> SEQUENCE: 22
atgaagaaat taatcatcag cattatggcg atcatgctat ttttaacagg ttgtggtaaa 60
agccaagaga aagccactct ggaaaaggat atcgataatt tacaaaaaga aaataaagaa 120
ttaaaagata aaaaagaaaa gcttcaacaa gaaaaagaaa aattagcaga taagcaaaaa 180
gaccttgaaa aagaagtgaa agatttaaaa ccttcaaaag aagataacaa ggacgataaa 240
aaagacgaag acaaaaataa agacaaagat aaagaggcat cacaagataa gcaatcaaaa 300
gatcaaacta agtcatcgga taaagataat cacaaaaagc ctacatcaac agataaagat 360
caaaaagcta atgacaaaca ccaatcataa 390

<210> SEQ ID NO 23
<211> LENGTH: 2982
<212> TYPE: DNA
<213> ORGANISM: Staphylococcus aureus

<400> SEQUENCE: 23
atgaagaacg catttaaatt atttaaaatg gatctgaaga aagtagctaa gacgccagct 60
gtgtggatta tcttagcagg cttagctatt ttgccatcgt tctacgcttg gtttaactta 120
tgggcaatgt gggatccata tggcaacacg ggacacatca aggtcgcagt cgttaatgaa 180
gataaaggcg acacaatcag agggaaaaaa gttaatgtcg gtaatacgat ggttaacaca 240
ctcaagaaaa ataaaagttt tgattggcag tttgtaagta gagagaaagc tgatcatgag 300
ataaaaatgg gtaaatattt tgcaggtatt tacatcccat ctaagtttac acatgaaatt 360
accgggacac tacgtaagca gcctcaaaaa gcagatgtag aatttaaggt gaatcagaag 420
attaacgctg ttgcgtctaa gctaacagat actggttcgt cagttgtcgt tgaaaaagcg 480
aatgaacaat ttaataaaac agtaactcga gcattattag aagaagctaa caaagcaggt 540
ttaactattg aagaaaatgt gccgacaatt aataagataa aaaatgcggt atattcggca 600

-continued

```
gataaagctt tacctaagat taatgacttt gcgaataaaa ttgtatattt gaataaccac    660
caagcggatt tagataaata tgcgaatgat tttagaaaac taggaaatta taaaggtgat    720
attttagatg ctcagaaaaa attaaacgaa gtcaatggtg ctattccgca acttaatgaa    780
aaggctaagt tgatattagc tttaaataat tatatgccga aaattgaaaa agcgttaaat    840
tttgcagctg atgacgtgcc agcgcagttc cctaaaatta atcaaggact taacattgcg    900
agtcaaggta ttgatcaagc taatggacag ttaaatgatg ccaaaggctt cgtcacacaa    960
gttagaagta gagtcggtga ttatcaagaa gcaattcgac gcgcgcaaga tttgaatcga   1020
agaaaccagc aacagattcc tcaaaatagc gcggcgaaca acgaaacatc aaatagtgca   1080
cctgcagctg gtaatggtgt aacatcaacg ccaccaagtg caccaaatgg caatactaca   1140
ccaaataata atgttacgca aaataccgca ccaaatagta ataatgcacc tgtatcgact   1200
acaccacaaa gtacaagcgg gaaaaaagat ggtcaaagtt ttgcagatat aacaacaaca   1260
caagtcagca cagctaacga gaacacacaa aatattacag ataaagatgt taaatcaatg   1320
gaagcggcat taacgggctc tttattatca ttatcaaata atttagatac ccaagcgaaa   1380
gccgcacaaa aagatagtca ggcattacgt aatatttcgt atggcatttt agcatcggac   1440
aagccatctg attttagaga gtctttagat aatgttaagt ccggtttaga atacacaact   1500
caatataatc aacaatttat cgatacatta aaagagattg agaagaatga aaatgttgat   1560
ttatcaaaag aaattgataa ggtaaagaca gctaataatc gaattaatga atcattaagg   1620
ttagttaatc aattaagtaa tgcattaaag aatggtagtt caggaactgc tgaagctact   1680
aaattactag atcaactgtc aaaactagat tcatcattat catcatttag agattatgtt   1740
aaaaaagatc ttaacagctc tttagtatca atatcacaac gtattatgga tgaattgaac   1800
aaagggcaaa cggcattgtc taatgttcag tctaagctaa atacaattga tcaagtcatc   1860
aacagtggtc aatctatttt aaaaaatggt aaaacacgta tcgatcgttt acaaacagta   1920
ttaccaagta ttgaacaaca atacattagt gctattaaaa atgctcaagc aaacttcccg   1980
aaagtgaaaa gtgatgtagc gaaagcagct aactttgtac gtaacgattt accacagttg   2040
gagcaacgtt taaccaatgc gactgcaagt gtgaataaaa atttaccaac gttattaaat   2100
ggttatgatc aagcggtagg attactaaat aaaaatcagc cacaagcgaa aaaggcttta   2160
tcagatttag ctgattttgc acaaaataaa ttgccagatg ttgaaaaaga tctgaaaaaa   2220
gcgaataaga ttttcaagaa gttagacaaa gacgatgcag tcgataaatt aatcgacaca   2280
cttaagaatg atttgaaaaa gcaagcgggt attattgcaa atcctattaa taagaagact   2340
gttgatgttt tcccagttaa ggattatgga tcagggatga caccattcta tactgcatta   2400
tcggtatggg taggcgcact cttaatggta agcctattaa ctgttgataa taaacataag   2460
agcttagagc cagtgttaac gacacgacaa gtattcttag gtaaagcagg attctttata   2520
atgcttggta tgttgcaagc actcattgta tcggttggag atttgttaat cctaaaagca   2580
ggagttgagt cacctgtatt attcgtactt ataacgattt tctgttcgat tattttcaac   2640
tcaatcgtat atacgtgcgt atcattactt ggtaacccag gtaaagccat tgcaatcgta   2700
ttgcttgtat tacaaattgc aggtggtgga ggtacattcc caattcaaac gacaccacaa   2760
tttttccaaa acatttcgcc atacttacca tttacgtatg caattgattc attacgtgaa   2820
acagtaggcg gtattgttcc ggaaatctta attacaaaat taattatatt aacgttattt   2880
ggcataggat tcttcgttgt aggtttaatt ttaaaacctg taacagatcc attgatgaag   2940
cgcgtatctg aaaaagttga ccaaagtaac gttacagaat aa                      2982
```

<210> SEQ ID NO 24
<211> LENGTH: 6201
<212> TYPE: DNA
<213> ORGANISM: Staphylococcus aureus

<400> SEQUENCE: 24
atgaatgaaa aagtagaagg catgaccttg gagctgaaat tagaccattt aggtgtccaa 60
gaaggcatga aaggtttaaa gcgacaatta ggtgttgtta atagtgaaat gaaagctaat 120
ctgtcagcat ttgataagtc tgaaaaatca atggaaaaat atcaggcgag aattaagggg 180
ttaaatgata ggcttaaagt tcaaaaaaag atgtattctc aagtagaaga tgagcttaaa 240
caagttaacg ctaattacca aaaagctaaa tccagtgtaa aagatgttga gaaagcatat 300
ttaaagttag tagaagccaa taaaaaagaa aaattagctc ttgataaatc taaagaagcc 360
ttaaaatcat cgaatacaga acttaaaaaa gctgaaaatc aatataaacg tacaaatcaa 420
cgtaaacaag atgcgtatca aaaacttaaa cagttgagag atgcagaaca aaagcttaag 480
aatagtaacc aagctactac tgcacaacta aaaagagcaa gtgacgcagt acagaagcag 540
tccgctaagc ataaagcact tgttgaacaa tataaacaag aaggcaatca agttcaaaaa 600
ctaaaagtgc aaaatgacaa tctttcaaaa tcaaatgata aaattgaaag ttcttacgct 660
aaaactaata ctaaattaaa gcaaacagaa aaagaattta atgatttaaa caatactatt 720
aagaatcata gcgctaatgt cgcaaaagct gaaacagctg ttaataaaga aaaagctgct 780
ttaaataatt tggagcgttc aatagataaa gcttcatccg aaatgaagac ttttaacaaa 840
gaacaaatga tagctcaaag tcatttcggt aaacttgcaa gtcaagcgga tgtcatgtca 900
aagaaattta gttctattgg agacaaaatg acttccctgg gacgtacaat gacgatgggc 960
gtatctacac caattacttt agggttaggt gcagcattaa aaacaagtgc agactttgaa 1020
ggccaaatgt ctcgagttgg agcgattgcg caagcaagca gtaaagactt gaaaagcatg 1080
tctaatcaag cagttgactt aggagctaaa accagtaaaa gtgctaacga agttgctaaa 1140
ggtatggaag aattggcagc tttaggcttt aatgccaaac aaacaatgga ggctatgcca 1200
ggtgttatca gtgcagcaga agcaagtggt gcagaaatgg ctacaactgc aactgtaatg 1260
gcttcagcga ttaactcttt cggtttaaaa gcatctgatg caaatcatgt tgctgattta 1320
cttgcgagat cagcaaatga tagtgctgca gatattcagt acatgggaga tgcattgaag 1380
tatgctggta ctcctgcaaa agcattagga gtttcaatag aggacacttc cgcagcaatt 1440
gaagttttat ctaactcagg tttagagggt tctcaagcag gtactgccct aagagcttca 1500
tttatcaggc tagctaatcc aagtaaaaat acagctaagg aaatgaaaaa attaggtatt 1560
catttgtctg atgctaaagg tcaatttgtt ggcatgggtg aattgattag acagttccaa 1620
gataatatga aaggcatgac gagagaacaa aaactagcta cagtggctac aatagttggt 1680
actgaagcag caagtggatt tttagccttg attgaagcgg gaccagataa aattaatagc 1740
tatagtaaat ccttaaagaa ttccaatggc gaaagtaaaa aagcagcaga tttgatgaaa 1800
gataatctca aaggcgctct ggaacaatta ggtggcgctt ttgaatcatt agcaatcgaa 1860
gtcggtaaag atttaacgcc tatgattaga gcaggagcgg aaggtttaac aaaattagtt 1920
gatggattta cacatctccc tggttgggtt agaaaagctt cagtaggatt agcacttttt 1980
ggtgcatcta ttggccctgc tgttcttgct ggtggcttat taatacgtgc agttggaagt 2040
gctgctaaag gctatgcatc attaaataga cgcattgctg aaaatacaat actgtctaat 2100

-continued

```
accaattcaa aagcaatgaa atctttaggt cttcaaacct tatttcttgg ttctacaaca   2160
ggaaaaacgt caaaaggctt taaaggatta gccggagcta tgttgtttaa tttaaaacct   2220
ataaatgttt tgaaaaattc tgcaaagcta gcaattttac cgttcaaact tttgaaaaac   2280
ggtttaggat tagccgcaaa atccttattt gcagtaagtg gaggcgcaag atttgctggt   2340
gtagccttaa agtttttaac aggacctata ggtgctacaa taactgctat tacaattgca   2400
tataaagttt ttaaaaccgc atatgatcgt gtggaatggt tcagaaacgg tattaacggt   2460
ttaggagaaa ctataaagtt ttttggtggc aaaattattg gcggtgctgt taggaagcta   2520
ggagagttta aaaattatct tggaagtata ggcaaaagct tcaaagaaaa gttttcaaag   2580
gatatgaaag atggttataa atctttgagt gacgatgacc ttctgaaagt aggagtcaac   2640
aagtttaaag gatttatgca aaccatgggc acagcttcta aaaaagcatc tgatactgta   2700
aaagtgttgg ggaaaggtgt ttcaaaagaa acagaaaaag ctttagaaaa atacgtacac   2760
tattctgaag agaacaacag aatcatggaa aaagtacgtt taaactcggg tcaaataaca   2820
gaagacaaag caaaaaaact tttgaaaatt gaagcggatt tatctaataa ccttatagct   2880
gaaatagaaa aaagaaataa aaaggaactc gaaaaaactc aagaacttat tgataagtat   2940
agtgcgttcg atgaacaaga aaagcaaaac attttaacta gaactaaaga aaaaaatgac   3000
ttgcgaatta aaaaagagca agaactcaat cagaaaatca aagaattgaa agaaaaagct   3060
ttaagtgatg gtcagatttc agaaaatgaa agaaaagaaa ttgaaaagct tgaaaatcaa   3120
agacgtgaca tcactgttaa agaattgagt aagactgaaa aagagcaaga gcgtatttta   3180
gtaagaatgc aaagaaacag aaattcttat tcaatagacg aagcgagcaa agcaattaaa   3240
gaagcagaaa aagcaagaaa agcaaaaaaa aaagaagtgg acaagcaata tgaagatgat   3300
gtcattgcta taaaaaataa cgtcaacctt tctaagtctg aaaaagataa attattagct   3360
attgctgatc aaagacataa ggatgaagta agaaaggcaa aatctaaaaa agatgctgta   3420
gtagacgttg ttaaaaagca aaataaagat attgataaag agatggattt atccagtggt   3480
cgtgtatata aaaatactga aaaatggtgg aatggcctta aagttggtgg gtctaacttc   3540
agagaagacc aaaagaagaa aagtgataag tacgctaaag aacaagaaga aacagctcgt   3600
agaaacagag aaaatataaa gaaatggttt ggaaatgctt gggacggcgt aaaaagtaaa   3660
actggcgaag cctttagtaa aatgggcaga aatgctaatc attttggcgg cgaaatgaaa   3720
aaaatgtgga gtggaatcaa aggaattcca agcaaattaa gttcaggttg gagctcagcc   3780
aaaagttctg taggatatca cactaaggct atagctaata gtactggtaa atggtttgga   3840
aaagcttggc aatctgttaa atcgactaca ggaagtattt acaatcaaac taagcaaaag   3900
tattcagatg cctcagataa agcttgggcg cattcaaaat ctatttggaa agggacatca   3960
aaatggttta gcaatgcata taaaagtgca aagggctggc taacggatat ggctaataaa   4020
tcgcgctcga aatgggataa tatttctagt acagcatggt cgaatgcaaa atccgtttgg   4080
aaaggaacat cgaaatggtt tagtaactca tacaaatctt taaaaggttg gactggagat   4140
atgtattcaa gagcccacga tcgttttgat gcaatttcaa gttcggcatg gtctaacgct   4200
aaatcagtat ttaatggttt tagaaaatgg ctatcaagaa catatgaatg gattagagat   4260
attggtaaag acatgggaag agctgcggct gatttaggta aaaatgttgc taataaagct   4320
attggcggtt tgaatagcat gattggcggt attaataaaa tatctaaagc cattactgat   4380
aaaaatctca tcaagccaat acctacattg tctactggta ctttagcagg aaagggtgta   4440
gctaccgata attcgggagc attaacgcaa ccgacatttg ctgtattaaa tgatagaggt   4500
```

```
tctggaaacg ccccaggcgg tggagttcaa gaagtaattc acagggctga cggaacattc   4560
catgcacccc aaggacgaga tgtggttgtt ccactaggag ttggagatag tgtaataaat   4620
gccaatgaca ctctgaagtt acagcggatg ggtgttttgc caaaattcca tggtggtacg   4680
aaaaagaaaa aatggatgga acaagttact gaaaatcttg gtaaaaaagc aggggacttc   4740
ggttctaaag ctaaaaacac agctcataat atcaaaaaag gtgcagaaga aatggttgaa   4800
gccgcaggcg ataaaatcaa agatggtgca tcttggttag gcgataaaat cggcgatgtg   4860
tgggattatg tacaacatcc agggaaacta gtaaataaag taatgtcagg tttaaatatt   4920
aattttggag gcggagctaa cgctacagta aaaattgcta aaggcgcgta ctcattgctc   4980
aaaaagaaat tagtagacaa agtaaaatcg tggtttgaag attttggtgg tggaggcgat   5040
ggaagctatc tatttgacca tccaatttgg caaaggtttg ggagctacac aggtggactt   5100
aactttaatg gcggtcgtca ctatggtatc gactttcaaa tgcctactgg aacgaacatt   5160
tatgctgtta aaggcggtat agctgataaa gtatggactg attacggtgg cggtaattct   5220
atacaaatta agaccggtgc taacgaatgg aactggtata tgcatttatc taagcaatta   5280
gcaagacaag gccaacgtat taaagctggt caactgatag ggaaatcagg tgctacaggt   5340
aatttcgtta gaggagcaca cttacatttc caattgatgc aagggtcgca tccagggaat   5400
gatacagcta aagatccaga aaaatggttg aagtcactta aaggtagtgg cgttcgaagt   5460
ggttcaggtg ttaataaggc tgcatctgct tgggcaggcg atatacgtcg tgcagcaaaa   5520
cgaatgggtg ttaatgttac ttcgggtgat gtaggaaata ttattagctt gattcaacac   5580
gaatcaggag gaaatgcagg tataactcaa tctagtgcgc ttagagacat caacgtttta   5640
cagggcaatc cagcaaaagg attgcttcaa tatatcccac aaacatttag acattatgct   5700
gttagaggtc acaacaatat atatagtggt tacgatcagt tattagcgtt ctttaacaac   5760
agctattggc gctcacagtt taacccaaga ggtggttggt ctccaagtgg tccaagaaga   5820
tatgcgaatg gtggtttgat tacaaagcat caacttgctg aagtgggtga aggagataaa   5880
caggagatgg ttatcccttt aactagacgt aaacgagcaa ttcaattaac tgaacaggtt   5940
atgcgcatca tcggtatgga tggcaagcca aataacatca ctgtaaataa tgatacttca   6000
acagttgaaa aattgttgaa acaaattgtt atgttaagtg ataaaggaaa taaattaaca   6060
gatgcattga ttcaaactgt ttcttctcag gataataact taggttctaa tgatgcaatt   6120
agaggtttag aaaaaatatt gtcaaaacaa agtgggcata gagcaaatgc aaataattat   6180
atgggaggtt tgactaatta a                                             6201
```

<210> SEQ ID NO 25
<211> LENGTH: 1830
<212> TYPE: DNA
<213> ORGANISM: Staphylococcus aureus

<400> SEQUENCE: 25

```
atgaaaaagc aaataatttc gctaggcgca ttagcagttg catctagctt atttacatgg     60
gataacaaag cagatgcgat agtaactaaa gattatagta aagaatcaag agtgaatgag    120
aacagtaaat acgatacacc aattccagat tggtatctag gtagtatttt aaacagatta    180
ggggatcaaa tatactacgc taaggaatta actaataaat acgaatatgg tgagaaagag    240
tataagcaag cgatagataa attgatgact agagttttgg gagaagatca ttatctatta    300
gaaaaaaaga aagcacaata tgaagcatac aaaaaatggt ttgaaaaaca taaaagtgaa    360
```

```
aatccacatt ctagtttaaa aaagattaaa tttgacgatt ttgatttata tagattaacg    420

aagaaagaat acaatgagtt acatcaatca ttaaaagaag ctgttgatga gtttaatagt    480

gaagtgaaaa atattcaatc taaacaaaag gatttattac cttatgatga agcaactgaa    540

aatcgagtaa caaatggaat atatgatttt gtttgcgaga ttgacacatt atacgcagca    600

tattttaatc atagccaata tggtcataat gctaaagaat taagagcaaa gctagatata    660

attcttggtg atgctaaaga tcctgttaga attacgaatg aaagaataag aaaagaaatg    720

atggatgatt taaattctat tattgatgat ttctttatgg atacaaacat gaatagacca    780

ttaaacataa ctaaatttaa tccgaatatt catgactata ctaataagcc tgaaaataga    840

gataacttcg ataaattagt caaagaaaca agagaagcaa tcgcaaacgc tgacgaatct    900

tggaaaacaa gaaccgtcaa aaattacggt gaatctgaaa caaaatctcc tgttgtaaaa    960

gaagagaaga aagttgaaga acctcaatta cctaaagttg gaaaccagca agaggataaa   1020

attacagttg gtacaactga agaagcacca ttaccaattg cgcaaccact agttaaaatt   1080

ccacagggca caattcaagg tgaaattgta aaaggtccgg aatatctaac gatggaaaat   1140

aaaacgttac aaggtgaaat cgttcaaggt ccagatttcc caacaatgga acaaaacaga   1200

ccatctttaa gcgataatta tactcaaccg acgacaccga accctatttt aaaaggtatt   1260

gaaggaaact caactaaact tgaaataaaa ccacaaggta ctgaatcaac gttaaaaggt   1320

actcaaggag aatcaagtga tattgaagtt aaacctcaag caactgaaac aacagaagca   1380

tcacattatc cagcgagacc tcaatttaac aaaacaccta agtatgtgaa atatagagat   1440

gctggtacag gtatccgtga atacaacgat ggaacatttg gatatgaagc gagaccaaga   1500

ttcaacaagc caagcgaaac aaatgcatac aacgtaacga caaatcaaga tggcacagta   1560

tcatatggcg ctcgcccgac acaaaacaag ccaagcgaaa caaacgcata taacgtaaca   1620

acacatgcaa acggccaagt atcatacgga gctcgtccga cacaaaacaa gccaagcgaa   1680

acgaacgcat ataacgtaac aacacatgca aacggtcaag tgtcatacgg agctcgccca   1740

acacaaaaca agccaagtaa aacaaatgca tacaatgtaa caacacatgc agatggtact   1800

gcgacatatg gtcctagagt aacaaaataa                                    1830
```

<210> SEQ ID NO 26
<211> LENGTH: 435
<212> TYPE: DNA
<213> ORGANISM: Staphylococcus aureus

<400> SEQUENCE: 26

```
atgaaaaaag taatcggact gctactagta agtacattag ctttaacagc ttgtggtgaa     60

aaagaaaaac caaaaaaaga agaaaataaa aagtcacaaa cacaaaaaca caaagatagc    120

aaaccaaaaa cgcaacaaga aaaaatgaaa aaagttgaag ataaaaatcc acctaataat    180

agcatacaaa ataattcaaa caatcaaaac caatcacaaa acaatcaact taataataat    240

tcagatccat ctaataatac tcctgcaaat ataaataaaa acgattcaca aaatactaat    300

ttaaatgatg agtatgtcgt ttcgcctggc tggactaaag atgaacaggc taaagctttt    360

gaagagtaca aaaaaggaaa agaagacgaa gcaagagctg gtgctagcgc agtaccagga    420

gccaatatta actaa                                                     435
```

<210> SEQ ID NO 27
<211> LENGTH: 3774
<212> TYPE: DNA
<213> ORGANISM: Staphylococcus aureus

<400> SEQUENCE: 27
atggcgaaaa aatttaatta caaactacca tcaatggttg cattaacgct tgtaggttca 60
gcagtcactg cacatcaagt tcaagcagct gagacgacac aagatcaaac tactaataaa 120
aatgttttag atagtaataa agttaaagca actactgaac aagcaaaagc tgaggtaaaa 180
aatccaacgc aaaacatttc tggcactcaa gtatatcaag accctgctat tgtccaacca 240
aaagcagcga ataaaacagg caatgctcaa gtaaatcaaa aggttgatac tacacaagta 300
aatggtgaca ctcgtgcgac tcaatcaact acatcaaata atgcgaaacc tgttacaaag 360
tcaacaaaca caacagcacc taaaacgaac aataatgtta caagtgctgg atatagttta 420
gttgatgatg aagatgataa ttcagaaaat caaattaatc cagaattaat taaatcagct 480
gctaaacctg ctgctcttga aacgcaatat aaagccgcag caccaaaagc aacacctgtt 540
gcacctaaag ctaaaactga agctacacca aaagtaacta cttttagtgc ttcagcacaa 600
ccaagatcag ccgctgcagc acctaaaacg agtttgccaa aatataaacc gcaagtaaac 660
tcatcaatta atgattacat tcgtaaaaat aatttaaaag cacctaagat agaggaagat 720
tatacatctt acttccctaa atacgcatac cgtaacggtg taggtcgtcc tgaaggtatc 780
gttgttcatg atacagctaa tgatcgttcg acgataaatg gcgaaattag ttatatgaaa 840
aacaactatc aaaacgcatt cgtacatgca tttgttgatg gggatcgtat aatcgaaaca 900
gcaccaacgg attacttatc ttggggtgtc ggtgcagtcg gtaaccctag attcatcaat 960
gttgaaatcg tgcacacaca cgattatgct tcatttgcac gttcaatgaa taactatgct 1020
gactatgcag ctacacaatt acaatattat ggtttaaaac ctgatagtgc tgaatatgat 1080
ggaaatggta cagtatggac tcactacgct gtaagtaaat atttaggtgg tacggaccat 1140
gccgatccac atggatattt aagaagtcat aattatagtt atgatcaact atatgactta 1200
attaatgaaa aatatttaat aaaaatgggt aaagtggcgc catggggtac gcaatctaca 1260
actaccccta ctacaccatc aaaaccatca acaccgtcga aaccatcaac accatcaact 1320
ggtaaattaa cagttgctgc taataatggt gtcgcacaaa tcaaacctac aaatagtggt 1380
ttatatacta ctgtttacga caaaactggt aaagcaacta atgaagttca aaaaacattt 1440
gctgtatcta aaacagctac attaggtaat caaaaattct atcttgttca agattacaat 1500
tctggtaata aatttggttg ggttaaagaa ggcgatgtgg tttacaacac agctaaatca 1560
cctgtaaatg taaatcaatc atattcaatc aaacctggta cgaaacttta tacagtacct 1620
tggggtacat ctaaacaagt tgctggtagc gtgtctggtt ctggaaacca aacatttaag 1680
gcttcaaagc aacaacaaat tgataaatca atttatttat atggctctgt gaatggtaaa 1740
tctggttggg taagtaaagc atatttagtt gatactgcta aacctacgcc tacaccaaca 1800
cctaagccat caacacctac aacaaataat aaattaacag tttcatcatt aaacggtgtt 1860
gctcaaatta atgctaaaaa caatggctta ttcactacag tttatgacaa aactggtaag 1920
ccaacgaaag aagttcaaaa aacatttgct gtaacaaaag aagcaagtct aggtggaaac 1980
aaattctact tagttaaaga ttacaatagt ccaactttaa ttggttgggt taaacaaggt 2040
gacgttattt ataacaatgc aaaatcacct gtaaatgtaa tgcaaactta tacagtaaaa 2100
ccaggcacta aattatattc agtaccttgg ggtacttata aacaagaagc tggtgcggta 2160
tctggtacag gtaaccaaac ttttaaagcg actaagcaac aacaaattga taaatctatc 2220
tatttatatg gaactgtaaa tggtaaatct ggttggataa gtaaagcata tttagctgta 2280

-continued

```
cctgctgcac ctaaaaaagc tgtagcacaa ccaaaaactg ctgtaaaagc ttatgctgtt   2340

actaaacctc aaacgactca aacagttagc aaaattgctc aagttaaacc aaacaacact   2400

ggtattcgtg cttctgttta tgaaaaaaca gcgaaaaacg gtgcaaaata tgcggatcgt   2460

acattctatg taacaaaaga acgtgcacat ggtaatgaaa catacgtatt attaaataat   2520

acaagtcata atattccatt aggttggttc aatgtaaaag acttaaatgt tcaaaactta   2580

ggcaaagaag ttaaaacgac tcaaaaatat actgttaaca gatcaaataa cggcttatca   2640

atggttcctt ggggtactaa aaaccaagtc attttaacag gcaataacat tgctcaaggt   2700

acatttaatg caacgaaaca agtatctgta ggcaaagatg tttatttata cggtactatt   2760

aataaccgca ctggttgggt aaattcaaaa gatttaactg caccaactgc tgttaaacca   2820

actacatcag ctgccaaaga ttataactac acttatgtaa ttaaaaatgg taatggttat   2880

tactatgtaa caccaaattc tgatacagct aaatactcat taaaagcatt taatgaacaa   2940

ccattcgcag ttgttaaaga acaagtcatt aatggacaaa cttggtacta tggtaaatta   3000

tctaacggta aattagcatg gattaaatca actgatttag ctaaagaatt aattaagtat   3060

aatcaaatag gtatgacatt aaaccaagtt gctcaaatac aagctggttt acaatataaa   3120

ccacaagtac aacgtgtacc aggtaagtgg acagatgcta actttaatga tgttaagcat   3180

gcaatggata cgaagcgttt agctcaagat ccagcattaa aatatcaatt cttacgctta   3240

gaccaaccac aaaatatttc tattgataaa attaatcaat tcttaaaagg taaaggtgta   3300

ttagaaaacc aaggtgctgc atttaacaaa gctgctcaaa tgtatggcat taatgaagtt   3360

tatcttatct cacatgccct attagaaaca ggtaacggta cttctcaatt agcaaaaggt   3420

gcagatgtag tgaacaacaa agttgtaact aactctaaca cgaaatacca taacgtattt   3480

ggtattgctg catatgataa cgatccttta cgtgaaggta ttaaatatgc taaacaagct   3540

ggttgggaca cagtatcaaa agcaatcgtt ggtggtgcta aattcatcgg caactcatat   3600

gttaaagctg gtcaaaatac gctttacaaa atgagatgga atcctgcaca tccaggaaca   3660

caccaatatg ctacagatgt agattgggct aacatcaatg ctaaaatcat caaaggctac   3720

tatgataaaa ttggcgaagt cggcaaatac ttcgacatcc cacaatataa ataa         3774
```

<210> SEQ ID NO 28
<211> LENGTH: 1461
<212> TYPE: DNA
<213> ORGANISM: Staphylococcus aureus

<400> SEQUENCE: 28

```
atgtctaata attttaaaga tgactttgaa aaaaatcgtc aatcgataga cacaaattca     60

catcaagacc atacggaaga tgttgaaaaa gaccaatcag aattagaaca tcaggataca    120

atagagaata cggagcaaca gtttccgcca agaaatgccc aaagaagaaa aagacgccgt    180

gatttagcaa cgaatcataa taaacaagtt cacaatgaat cacaaacatc tgaagacaat    240

gttcaaaatg aggctggcac aatagatgat cgtcaagtcg aatcatcaca cagtactgaa    300

agtcaagaac ctagccatca agacagtaca cctcaacatg aagagggata ttataataag    360

aatgcttttg caatggataa atcacatcca gaaccaatcg aagacaatga taaacacgag    420

actattaaag aagcagaaaa taacactgag cattcaacag tttctgataa gagtgaagct    480

gaacaatctc agcaacctaa accatatttt gcaacaggtg ctaaccaagc aaatacatca    540

aaagataaac atgatgatgt aactgttaag caagacaaag atgaatctaa agatcatcat    600

agtggtaaaa aaggcgcagc aattggtgct ggaacagcgg gtgttgcagg tgcagctggt    660
```

```
gcaatgggtg tttctaaagc taagaaacat tcaaatgacg ctcaaaacaa aagtaattct    720

ggcaaggtga ataactcgac tgaggataaa gcgtctgaag acaagtcaaa agaacatcat    780

aatggtaaaa aaggtgcagc aatcggtgct ggaacagcag gtttggctgg aggcgcagca    840

agtaatagtg cttctgccgc ttcaaaacca catgcctcta ataatgcaag tcaaaacaat    900

gatgaacatg accatcatga cagagataaa gaacgtaaaa aaggtggcat ggccaaagta    960

ttgttaccat taattgcagc tgtactaatt atcggtgcat tagcgatatt tggaggcatg   1020

gcattaaaca atcataataa tggtacaaaa gaaaataaaa tcgcgaatac aaataaaaat   1080

aatgctgatg aaagtaaaga taaagacaca tctaaagacg cttctaaaga taaatcaaaa   1140

tctacagaca gtgataaatc aaaagatgat caagacaaag cgactaaaga tgaatctgat   1200

aatgatcaaa acaacgctaa tcaagcgaac aatcaagcac aaaataatca aaatcaacaa   1260

caagctaatc aaaatcaaca acagcaacaa caacgtcaag gtggtggcca aagacataca   1320

gtgaatggtc aagaaaactt ataccgtatc gcaattcaat actacggttc aggttcaccg   1380

gaaaatgttg aaaaaattag acgtgccaat ggtttaagtg gtaacaatat tagaaacggt   1440

caacaaatcg ttattccata a                                             1461
```

```
<210> SEQ ID NO 29
<211> LENGTH: 3825
<212> TYPE: DNA
<213> ORGANISM: Staphylococcus aureus

<400> SEQUENCE: 29

atgagctggt ttgataaatt attcggcgaa gataatgatt caaatgatga cttgattcat     60

agaaagaaaa aaagacgtca agaatcacaa aatatagata acgatcatga ctcattactg    120

cctcaaaata atgatattta tagtcgtccg aggggaaaat tccgttttcc tatgagcgta    180

gcttatgaaa atgaaaatgt tgaacaatct gcagatacta tttcagatga aaaagaacaa    240

taccatcgag actatcgcaa acaaagccac gattctcgtt cacaaaaacg acatcgccgt    300

agaagaaatc aaacaactga agaacaaaat tatagtgaac aacgtgggaa ttctaaaata    360

tcacagcaaa gtataaaata taaagatcat tcacattacc atacgaataa gccaggtaca    420

tatgtttctg caattaatgg tattgagaag gaaacgcaca agtcaaaaac acacaatata    480

tattctaata atacaaatca tcgtgctaaa gattcaacta cagattatca caaagaaagt    540

ttcaagactt cagaggtacc gtcagctatt tttggcacaa tgaaacctaa aaagttagaa    600

aatggtcgta tccctgtaag taaatcttca gaaaaagttg agtcagataa acaaaaatat    660

gataaatatg tagctaagac gcaaacgtct caaaataaac atttagaaca agagaaacaa    720

aaagatagtg ttgtcaagca aggaactgca tctaaatcat ctgatgaaaa tgtatcatca    780

acaacaaaat caacacctaa ttattcaaaa gttgataata ctatcaaaat tgaaaacatt    840

tatgcttcac aaattgttga agaaattaga cgtgaacgag aacgtaaagt gcttcaaaag    900

cgtcgattta aaaaagcgtt gcaacaaaag cgtgaagaac ataaaaacga agagcaagat    960

gcaatacaac gtgcaattga tgaaatgtat gctaaacaag cggaacgcta tgttggtgat   1020

agttcattaa atgatgatag tgacttaaca gataatagta cagaggctag tcagcttcat   1080

acaaatgaaa tagaggatga agctgtatca aatgatgaaa ataaaaaagc gtcaatacaa   1140

aatgaagaca ctgatgacac tcatgtagat gaaagtccat acaattatga ggaagttagt   1200

ttgaatcaag tatcgacaac aaaacaattg tcagatgatg aagttacggt ttcggatgta   1260
```

```
acgtctcaac gtcaatcagc actgcaacat aacgttgaag taaataatca agatgaacta   1320
aaaaatcaat ccagattaat tgctgattca gaagaagatg gagcaacgaa tgaagaagaa   1380
tattcaggaa gtcaaatcga tgatgcagaa ttttatgaat taaatgatac agaagtagat   1440
gaggatacta cttcaaatag cgaagataat accaatagag acgcgtctga aatgcatgta   1500
gacgctccta aaacgcaaga gcacgcagta actgaatctc aagttaataa tatcgataaa   1560
acggttgata atgaaattga attagcgcca cgtcataaaa aagatgacca aacaaactta   1620
agtgtcaact cattgaaaac gaatgatgtg aatgatggtc atgttgtgga agattcaagc   1680
atgaatgaaa tagaaaagca aaacgcagaa attacagaaa atgtgcaaaa cgaagcagct   1740
gaaagtaaac aaaatgtcga agagaaaact attgaaaacg taaatccaaa gaaacagact   1800
gaaaaggttt caactttaag taaaagacca tttaatgttg tcatgacgcc atctgataaa   1860
aagcgtatga tggatcgtaa aaagcattca aaagtcaatg tgcctgaatt aaagcctgta   1920
caaagtaaac aagctgcgag tgaaagcaag actgcgactc aaaacacacc atcatcaagt   1980
actgattcac aagagtcaaa cacgaatgca tataaaacaa ataatatgac atcaaacaat   2040
gttgagaaca atcaacttat tggtcatgca gcaacagaaa atgattatca aaatgcacaa   2100
caatattcag agcagaaacc ttctgctgat tcaactcaaa cggaaatatt tgaagaaagc   2160
caagatgata atcaattgga aaatgagcaa gttgatcaat caacttcgtc ttcagtttca   2220
gaagtaagcg acataactga agaaagcgaa gaaacaacac atcaaaacaa tactagtgga   2280
caacaagata atgatgatca acaaaaagat ttacagcttt cattttcaaa tcaaaatgaa   2340
gatacagcta atgaaaatag acctcggacg aatcaaccag atgttgcaac aaatcaagct   2400
gtacaaactt ctaagccgat gattcgtaaa ggcccaaata ttaaattgcc aagtgtttca   2460
ttactagaag aaccacaagt tattgagccg gacgaggact ggattacaga taaaaagaaa   2520
gaacttaatg acgcattatt ttactttaat gtacctgcag aagtacaaga tgtaactgaa   2580
ggtccaagtg ttacaagatt tgaattatca gttgaaaaag gtgttaaagt ttcaagaatt   2640
acggcattac aagatgacat taaaatggca ttggcagcga aagatattcg tatagaagcg   2700
ccaattccag gaactagtcg tgttggtatt gaagttccga accaaaatcc aacgacggtc   2760
aacttacgtt ctattattga atctccaagt tttaaaaatg ctgaatctaa attaacagtt   2820
gcgatggggt atagaattaa taatgaacca ttacttatgg atattgctaa aacgccacac   2880
gcactaattg caggtgcaac tggatcaggg aaatcagttt gtatcaatag tattttgatg   2940
tctttactat ataaaaatca tcctgaggaa ttaagattat tacttattga tccaaaaatg   3000
gttgaattag ctccttataa tggtttgcca catttagttg caccggtaat tacagatgtc   3060
aaagcagcta cacagagttt aaaatgggcc gtagaagaaa tggaaagacg ttataagtta   3120
tttgcacatt accatgtacg taatataaca gcatttaaca aaaaagcacc atatgatgaa   3180
agaatgccaa aaattgtcat agtaattgat gagttggctg atttaatgat gatggctccg   3240
caagaagttg agcagtctat tgctagaatt gctcaaaaag cgagagcatg tggtattcat   3300
atgttggtag ctacgcaaag accatctgtc aatgtaatta caggtttaat taaagccaac   3360
ataccaacaa gaattgcatt tatggtatca tcaagtgtag attcaagaac gatattagac   3420
agtggtggag cagaacgctt gttaggatat ggcgatatgt tatatcttgg tagcggtatg   3480
aataaaccga ttagagttca aggtacattt gtttctgatg acgaaattga tgatgttgtt   3540
gattttatca aacaacaaag agaaccggac tacctatttg aagaaaaaga attgttgaaa   3600
aaaacacaaa cacaatcaca agatgaatta tttgatgatg tttgtgcatt tatggttaat   3660
```

gaaggacata tttcaacatc attaatccaa agacatttcc aaattggcta taatagagca 3720
gcaagaatta tcgatcaatt agagcaactc ggttatgttt cgagtgctaa tggttcaaaa 3780
ccaagggatg tttatgttac ggaagcagat ttaaataaag aataa 3825

<210> SEQ ID NO 30
<211> LENGTH: 630
<212> TYPE: DNA
<213> ORGANISM: Staphylococcus aureus

<400> SEQUENCE: 30
atgtcgaatc aaaattacga ctacaataaa aatgaagatg gaagtaagaa gaaaatgagt 60
acaacagcga aagtagttag cattgcgacg gtattgctat tactcggagg attagtattt 120
gcaatttttg catatgtaga tcattcgaat aaagctaaag aacgtatgtt gaacgaacaa 180
aagcaggaac aaaaagaaaa gcgtcaaaaa gaaaatgcag aaaaagagag aaagaaaaag 240
caacaagagg aaaaagagca gaatgagcta gattcacaag caaaccaata tcagcaattg 300
ccacagcaga atcaatatca atatgtgcca cctcagcaac aagcacctac aaagcaacgt 360
cctgctaaag aagagaatga tgataaagca tcaaaggatg agtcgaaaga taaggatgac 420
aaagcatctc aagataaatc agatgataat cagaagaaaa ctgatgataa taaacaacca 480
gctcagccta aaccacagcc gcaacaacca acaccaaagc caaataataa tcaacaaaac 540
aatcaatcaa atcaacaagc gaaaccacaa gcaccacaac aaaatagcca atcaacaaca 600
aataaacaaa ataatgctaa tgataagtag 630

<210> SEQ ID NO 31
<211> LENGTH: 573
<212> TYPE: DNA
<213> ORGANISM: Staphylococcus aureus

<400> SEQUENCE: 31
atgaaattaa aatcattagc agtgttatca atgtcagcgg tggtgcttac tgcatgtggc 60
aatgatactc caaaagatga aacaaaatca acagagtcaa atactaatca agacactaat 120
acaacaaaag atgttattgc attaaaagat gttaaaacaa gcccagaaga tgctgtgaaa 180
aaagctgaag aaacttacaa aggccaaaag ttgaaaggaa tttcatttga aaattctaat 240
ggtgaatggg cttataaagt gacacaacaa aaatctggtg aagagtcaga agtacttgtt 300
gatgataaaa ataaaaaagt gattaacaaa aagactgaaa aagaagatac agtgaatgaa 360
aatgataact ttaaatatag cgatgctata gattacaaaa aagccattaa agaaggacaa 420
aaggaatttg atggtgatat taaagaatgg tcacttgaaa aagatgatgg taaacttgtt 480
tacaatatcg atttgaaaaa aggtaataaa aaacaagaag ttactgttga tgctaagaac 540
ggtaaagtat taaagagtga gcaagatcaa taa 573

<210> SEQ ID NO 32
<211> LENGTH: 3030
<212> TYPE: DNA
<213> ORGANISM: Staphylococcus aureus

<400> SEQUENCE: 32
atgaaaaaga aaaattggat ttatgcatta attgtcactt taattattat aattgccata 60
gttagtatga tatttttgt tcaaacaaaa tatggagatc aatcagaaaa aggatcccaa 120
agtgtaagta ataaaaataa taaaatacat atcgcaattg ttaacgagga tcaaccaacg 180

-continued

```
acatataacg gtaaaaaggt tgagctgggt caagcattta ttaaaaggtt agcaaatgag    240
aaaaactata aatttgaaac agtaacaaga aacgttgctg agtctggttt gaaaaatggc    300
ggataccaag tcatgattgt tatcccagaa aacttttcaa aattggcaat gcaattagac    360
gctaaaacac catcgaaaat atcactacag tataaaacag ctgtaggaca aaaagaagaa    420
gtagctaaaa acacagaaaa agttgtaagt aatgtactta acgactttaa caaaaacttg    480
gtcgaaattt atttaacaag catcattgat aatttacata atgcacaaaa aaatgttggc    540
gctattatga cgcgtgaaca tggtgtgaat agtaaattct cgaattactt attaaatcca    600
attaacgact tcccggaatt atttacagat acgcttgtaa attcgatttc tgcaaacaaa    660
gatattacaa aatggttcca aacatacaat aaatcattac tgagtgcgaa ttcagataca    720
ttcagagtga acacagatta taatgtttcg actttaattg aaaaacaaaa ttcattattt    780
gacgaacaca atacagcgat ggataaaatg ttacaagatt ataaatcgca aaaagatagc    840
gtggaacttg ataactatat caatgcatta aaacagatgg acagccaaat tgatcaacaa    900
tcaagtatgc aagatacagg taaagaagaa tataaacaaa ctgttaaaga aaacttagat    960
aaattaagag aaatcattca atcacaagag tcaccatttt caaaaggtat gattgaagac   1020
tatcgtaagc aattaacaga atcactccaa gatgagcttg caaacaacaa agacttacaa   1080
gatgcgctaa atagcattaa aatgaacaat gctcaattcg ctgaaaactt agagaaacaa   1140
cttcatgatg atattgtcaa agaacctgat tcagatacaa catttatcta taacatgtct   1200
aaacaagact ttatagctgc aggtttaaat gaggatgaag ctaataaata cgaagcaatt   1260
gtcaaagaag caaaacgtta taaaaacgaa tataatttga aaaaaccgtt agcagaacac   1320
attaatttaa cagattacga taaccaagtt gcgcaagaca caagtagttt gattaatgat   1380
ggtgtgaaag tgcaacgtac tgaaacgatt aaaagtaatg atattaatca attaactgtt   1440
gcaacagatc ctcattttaa ttttgaaggc gacattaaaa ttaatggtaa aaaatatgac   1500
attaaggatc aaagtgttca actcgataca tctaacaagg aatataaagt tgaagtcaat   1560
ggcgttgcta aattgaaaaa ggatgctgag aaagatttct taaaagataa aacaatgcat   1620
ttacaattgt tatttggaca agcaaatcgt caagatgaac caaatgataa gaaagcaacg   1680
agtgttgtgg atgtaacatt gaatcataac cttgatggtc gcttatcgaa agatgcatta   1740
agccagcaat tgagtgcatt atctaggttt gatgcgcatt ataaaatgta cacagataca   1800
aaaggcagag aagataaacc attcgacaac aaacgtttaa ttgatatgat ggttgaccaa   1860
gttatcaatg acatggaaag tttcaaagac gataaagtag ctgtgttaca tcaaattgat   1920
tcaatggaag aaaactcaga caaactgatt gatgacattt taaataacaa aaagaataca   1980
acaaaaaata aagaagatat ttctaagctg attgatcagt tagaaaacgt taaaaagact   2040
tttgctgaag agccacaaga accaaaaatt gataaaggca aaaatgatga atttaatacg   2100
atgtcttcaa atttagataa agaaattagt agaatttctg agaaaagtac gcaattgcta   2160
tcagatacac aagaatcaaa aacaattgca gattcagtta gtggacaatt aaatcaatta   2220
gataataatg tgaataaact acatgcgaca ggtcgagcat taggcgtaag agcgaatgat   2280
ttgaaccgtc aaatggctaa aaacgataaa gataatgagt tattcgctaa agagtttaaa   2340
aaagtattac aaaattctaa agatggcgac agacaaaacc aagcattaaa agcatttatg   2400
agtaatccgg ttcaaaagaa aaacttagaa aatgttttag ctaataatgg taatacagac   2460
gtgatttcac cgacattgtt cgtattattg atgtatttac tatcaatgat tacagcatat   2520
attttctata gctatgaacg tgctaaagga caaatgaatt tcatcaaaga tgattatagt   2580
```

```
agtaaaaaca atctttggaa taatgcgatt acgtctggtg ttattggtgc aactggttta   2640

gtagaaggat taattgtcgg tttaattgca atgaataagt tccatgtatt agctggctat   2700

agagcgaaat tcatcttaat ggtgatttta actatgatgg tcttcgtact tattaatacg   2760

tatttactaa gacaggtaaa atctatcggt atgttcttaa tgattgctgc attgggtcta   2820

tactttgtag ctatgaataa tttgaaagcg gctggacaag gtgtgactaa taaaatttca   2880

ccattatctt atatcgataa catgttcttc aattatttaa atgcagagca tcctataggc   2940

ttggcgctag taatattaac agtacttgtg attattggct ttgtactgaa catgtttata   3000

aaacacttta agaaagagag attaatctaa                                    3030
```

<210> SEQ ID NO 33
<211> LENGTH: 1191
<212> TYPE: DNA
<213> ORGANISM: Staphylococcus aureus

<400> SEQUENCE: 33

```
atgacgcaac aacaaaataa taaaagaaca ttaaaaaata aacacactta tcaaaatgaa     60

ccattaccaa accgtaaaga ttttgttgtt agttttataa ctggcgcgct tgttggttca    120

gctttaggct tatattttaa aaataaagtt tatcaaaaag cagatgattt aaaagtcaaa    180

gaacaagaac tgtcgcaaaa gtttgaagaa agaaaaacgc aacttgaaga aacggttgcc    240

tttacaaaag aacgtgttga aggattttta aacaaatcta aaaatgaaca agcggcattg    300

aaggcacaac aagcagcaat aaaagaagaa gcaagtgcaa ataatttaag cgatacatca    360

caagaggcac aagagattca agaagctaaa agagaagcac aaacagaaac ggataaaagt    420

gcggctgtat caaatgaaga gtcaaaggca tcggcattga aggcacaaca agcagcgata    480

aaagaagaag caagtgcaaa taatttaagt gatacatcac aagaagcaca agcgattcaa    540

gaagtgaaga aagaagcgca agcagaaaca gataaaagtg cagatgtatc aaatgaagaa    600

tcaaaagcat cgacattaaa cgtatcgaaa gaagagtcac aagctgaaag attagcaaac    660

gctgcaaaac agaagcaagc taaattaaca ccaggctcaa aagagagtca attaactgaa    720

gcgttatttg cagaaaaacc agttgctaaa aatgacttga aagaaattcc tctattagtt    780

actaaaaaga atgatgtatc agaaacagtt aatacagata ataaagacac tgttaaacaa    840

aaagaagcta aatttgaaaa tggtgttatt acacgtaaag ctgatgaaaa aacacctaat    900

aatacagctg ttgacaagaa atcaggtaaa caatctaaaa aaacaacacc ttcaaataaa    960

cgaaatgcat caaaagcatc gacaaataaa acttcaggtc agaaaaagca acataataag   1020

aaagcatcac aaggtgcaaa gaaacaaagt agttcaagta actcaacgac aaagactaat   1080

caaaaaaatt caaaagcaac aaatgctaaa tcatccaatg catcaaaaaa atcaaatgct   1140

aaagttgaaa aagctaaaag taaaatagag aaacgtacat ttaatgacta a            1191
```

<210> SEQ ID NO 34
<211> LENGTH: 2310
<212> TYPE: DNA
<213> ORGANISM: Staphylococcus aureus

<400> SEQUENCE: 34

```
gtggatattg gtaaaaaaca tgtaattcct aaaagtcagt accgacgtaa gcgtcgtgaa     60

ttcttccaca acgaagacag agaagaaaat ttaaatcaac atcaagataa acaaaatata    120

gataatacaa catcaaaaaa agcagataag caaatacata aagattcaat tgataagcac    180
```

```
gaacgtttta aaaatagttt atcatcgcat ttagaacaga gaaaccgtga tgtgaatgag    240
aacaaagctg aagaaagtaa aagtaatcag ggtagtaagt cagcatataa caaagatcat    300
tatttaacag acgatgtatc taaaaaacaa aattcattag attcagtaga ccaagataca    360
gagaaatcaa aatattatga gcaaaatact gaagcgactt tatcaactaa ttcaaccgat    420
aaagtagaat caactgacat gagaaagcta agttcagata aaaacaaagt tggtcatgaa    480
gagcaacatg tactttctaa accttcagaa catgataaag agactagaat tgattttgag    540
tcttcaagaa ctgattcaga cagctcgatg cagacagaga aaataaaaaa agacagttca    600
gatggaaata aaagtagtaa tctgaaatct gaagtaatat cagacaaatc aaattcagta    660
ccaatattgt cggaatctga tgatgaagta aataatcaga agccattaac tttgccggaa    720
gaacagaaat tgaaaaggca gcaaagtcaa aatgagcaaa caaaaactta tacatatggt    780
gatagcgaac aaaatgacaa gtctaatcat gaaaatgatt taagtcatca tacaccatcg    840
ataagtgatg ataaagatta cgttatgaga gaagatcata ttgttgacga taatcctgat    900
aatgatatca atacaccatc attatcaaaa atagatgacg atcgaaaact tgatgaaaaa    960
attcatgtcg aagataaaca taaacaaaat gcagactcat ctgaaacggt gggatatcaa   1020
agtcagtcaa gtgcatctca tcgtagcact gaaaaaagaa atatggctat taatgaccat   1080
gataaattaa acggtcaaaa accaaataca aagacatcgg caaataataa tcaaaaaaag   1140
gctacatcaa aattgaacaa agggcgcgct acaaataata attatagcgc cattttgaaa   1200
aagttttgga tgatgtattg gcctaaatta gttattctaa tgggtattat tattctaatt   1260
gttattttga atgccatttt taataatgtg aacaaaaatg atcgcatgaa tgataataat   1320
gatgcagatg ctcaaaaata tacgacaacg atgaaaaatg ccaataacgc agttaaatcg   1380
gtcgttacag ttgaaaatga aacatcaaaa gattcatcat tacctaaaga taaagcatct   1440
caagacgaag taggatcagg tgttgtatat aaaaaatctg gagatacgtt atatattgtt   1500
acgaatgcac acgttgtcgg tgataaagaa aatcaaaaaa taactttctc gaataataaa   1560
agtgttgttg ggaaagtgct tggtaaagat aaatggtcag atttagctgt tgttaaagca   1620
acttcttcag acagttcagt gaaagagata gctattggag attcaaataa tttagtgtta   1680
ggagagccaa tattagtcgt aggtaatcca cttggtgtag actttaaagg cactgtgaca   1740
gaaggtatta tttcaggtct gaacagaaat gttccaattg atttcgataa agataataaa   1800
tatgatatgt tgatgaaagc tttccaaatt gatgcatcag taaatccagg taactcgggt   1860
ggtgctgtcg tcaatagaga aggaaaatta attggtgtag ttgcagctaa aattagtatg   1920
ccaaacgttg aaaatatgtc atttgcaata cctgttaatg aagtacaaaa gattgtaaaa   1980
gaattagaaa caaaaggtaa aattgactat cccgatgtag gtgttaaaat gaagaatatt   2040
gccagtctaa atagttttga aagacaagca gttaaattgc taggaaaagt taagaacggt   2100
gttgttgtag atcaagttga caacaatggt ttagcagatc aatctggtct gaaaaaaggt   2160
gatgtaatta ctgaattaga tggcaaactt ttagaagatg atttacgctt taggcagatt   2220
atatttagtc ataaagatga cttgaaatca attacagcga agatttatag agatggtaaa   2280
gaaaaagaaa ttaatattaa actaaaataa                                    2310
```

<210> SEQ ID NO 35
<211> LENGTH: 627
<212> TYPE: DNA
<213> ORGANISM: Staphylococcus aureus

<400> SEQUENCE: 35
atgaaattca aagctatcgt tgcaatcaca ttatcattgt cactattaac cgcctgtggt 60
gctaatcaac ataaagaaaa tagtagtaaa tcaaatgaca ctaataaaaa gacgcaacaa 120
actgataaca ctacacagtc aaatacagaa aagcaaatga ctccacaaga agccgaagat 180
atcgttcgaa acgattacaa agcaagaggt gctaacgaaa atcaaacatt aaattataaa 240
acaaatcttg aacgaagtaa tgaacatgaa tattatgttg aacatctagt ccgcgatgca 300
gttggcacac cattaaaacg ttgcgctatt gttaatcgac acaatggtac gattattaat 360
atttttgatg atatgtcaga aaaagataaa gaagaatttg aagcatttaa aaagagaagc 420
cctaaataca acccaggtat gaatgatcaa gctgaaatgg ataatgagtc ggaagacatt 480
caacatcatg atattgacaa taacaaagcc attcaaaatg acttaccaga tcaaaaagtc 540
gatgataaaa acgataaaaa tgctgttaat aaagaagaaa aacacgataa ccgtgaaaat 600
aattcagcag aaactaaagt taaataa 627

<210> SEQ ID NO 36
<211> LENGTH: 684
<212> TYPE: DNA
<213> ORGANISM: Staphylococcus aureus

<400> SEQUENCE: 36
atggataaga aaaaagtcat caaatttatg attaatgtat taccaattgt attggtaccg 60
ttaattgttg aacgtaaacg tatcaaacaa catccggacg tacaaaaagt tacagatgct 120
acaagtaaag ttgcttcaaa aacatctgca gcaatcagta acacagcgag tgatgttaaa 180
gaatatgtcg gcgataaaaa acaagatttt gaaaataagc gtgaacttaa aaagtttgct 240
agagaacatg atcctgccta tattgagaaa aaaggcgaaa aattagctaa acaaaatcgt 300
aaagacgctg ataaaatgaa taaaatactt caaaaaaata tcgaaaagcg tcataaagaa 360
gagcaaaaag cccgcgaaaa gaatgaaata caacgtatta aagatatgaa aaagtcacaa 420
aaatacgaag taaaagcagg cttaacacct aataaattag atgagaaaac tgagaaaaaa 480
ggcgataaac tagctgaaaa aaatcgcaaa gaaatcgcta aaatgaataa aaagttacaa 540
aaaaatattg aaaaacgaca caaagaagaa caaaaacgcc aacaagaagc tgataaagca 600
cgcatcaagt catttaaaaa atataaagat tatgttgcca aaagcgcctc tcaacaaaat 660
aaagaaaaca atacagaggc ataa 684

<210> SEQ ID NO 37
<211> LENGTH: 1215
<212> TYPE: DNA
<213> ORGANISM: Staphylococcus aureus

<400> SEQUENCE: 37
atgtcatatc attggtttaa gaaaatgtta ctttcaacaa gtatgttaat tttaagtagt 60
agtagtagtt tagggcttgc aacgcacaca gttgaagcaa aggataactt aaatggagaa 120
aagccaacga ctaatttgaa tcataatgta acttcaccat cagtaaatag tgaaatgaat 180
aataatgaga ctgggacacc tcacgaatca aatcaagctg gtaatgaagg aactggttcg 240
aatagtcgtg atgctaatcc tgattcgaat aatgtgaagc cagactcaaa caaccaaaac 300
ccaagtccag attcaaaacc tgacccaaat aacccaaacc caggtccgaa tccgaagcca 360
gacccagata agccgaaacc aaatccggaa ccaaagccag acccagataa gccgaaacca 420
aatccggatc caaaaccaga tccagacaaa ccgaagccaa atccggatcc aaaaccagat 480

```
ccaaatccga atccgaatcc aaaaccagac cctaataagc caaatccaaa tccgtctcca    540

aatcccaatc aacctgggga ttccaatcaa tctggtggct cgaaaaatgg ggggacatgg    600

aacccaaatg cttcagatgg atctaatcaa ggtcaatggc aaccaaatgg aaatcaagga    660

aactcacaaa atcctactgg taatgatttt gtatcccaac gatttttagc cttggcgaat    720

ggggcttaca agtataatcc gtatatttta aatcaaatta atcaattggg gaaagaatat    780

ggtgaggtaa ctgatgaaga tatctacaat atcatccgta aacaaaactt cagcggaaat    840

gcatatttaa atggattaca acagcaatcg aattacttta gattccaata tttcaatcca    900

ttgaaatcag aaaggtacta tcgtaattta gatgaacaag tactcgcatt aattactggc    960

gaaattggat caatgccaga tttgaaaaag cccgaagata agccggattc aaaacaacgt   1020

tcatttgagc ctcatgaaaa agatgatttt acagttgtaa aaaaacaaga agataataag   1080

aaaagtgcgt caactgcata tagtaaaagt tggctagcaa ttgtatgttc tatgatggtg   1140

gtattttcaa tcatgctatt cttatttgta aagcgaaata aaaagaaaaa taaaaacgaa   1200

tcacagcgac gataa                                                    1215
```

<210> SEQ ID NO 38
<211> LENGTH: 696
<212> TYPE: DNA
<213> ORGANISM: Staphylococcus aureus

<400> SEQUENCE: 38

```
atgaagaaaa cattactcgc atcatcatta gcagtaggtt taggaatcgt agcaggaaat     60

gcaggtcacg aagcccaagc aagtgaagcg gacttaaata aagcatcttt agcgcaaatg    120

gcgcaatcaa atgatcaaac attaaatcaa aaaccaattg aagctggcgc ttataattat    180

acatttgact atgaagggtt tacttatcac tttgaatcag atggtacaca ctttgcttgg    240

aattaccatg caacaggtgc taatggagca gacatgagtg cacaagcacc tgcaactaat    300

aatgttgcac catcagctga tcaatctaat caagtacaat cacaagaagt tgaagcacca    360

caaaatgctc aaactcaaca accacaagca tcaacatcaa acaattcaca agttactgca    420

acaccaactg aatcaaaagc atcagaaggt tcatcagtaa atgtgaatga tcatctaaaa    480

caaattgctc aacgtgaatc aggtggcaat attcatgctg taaatccaac atcaggtgca    540

gctggtaagt atcaattctt acaatcaact tgggattcag tagcacctgc taaatataaa    600

ggtgtatcac cagcaaatgc tcctgaaagt gttcaagatg ccgcagcagt aaaactatat    660

aacactggtg gcgctggaca ttgggttact gcataa                             696
```

<210> SEQ ID NO 39
<211> LENGTH: 465
<212> TYPE: RNA
<213> ORGANISM: Staphylococcus aureus

<400> SEQUENCE: 39

```
augaaaagau uguuagguuu auuauuagug agcacguuag uguuaagugc auguggaaau     60

gaugagaauc aggaagaauc uaaaaaagaa guuaaaucaa aagaaaagaa aauugagaag    120

gaaaaggaaa auaaaucgaa aaaagauaag gaaaaagaag uugcaacaca acaacaacca    180

gacaaucaaa ccguugaaca accccaauca caagagcaau cgguucaaca accgcaacaa    240

cagauaccac aaaauagugu uccucagcaa aauguccaag uucaacaaaa caaaaagcaa    300

aaaguugauu uaaauaauau gccucccacu gauuuuucua cagaggguau gucugagcag    360

gcucaaaaac aaauugaaga gcuuucaaug caaaaagacu aucauggucu gucacaaaga    420
```

gaauacaaug auagaguuuc ugaaauuaua aauaaugaua auuga 465

<210> SEQ ID NO 40
<211> LENGTH: 555
<212> TYPE: RNA
<213> ORGANISM: Staphylococcus aureus

<400> SEQUENCE: 40
auguuaaaag gaugcggcgg uugccuuauu ucuuuuauua uauuaauuau cuuauuauca 60
gccuguucaa ugauguuuag uaauaaugac aauuccacua guaaucaauc aucaaaaacg 120
caauuaacuc aaaaagacga agauaaaagu gaaaauaugc cugaagaaaa aucagaauca 180
gaaacagaua aggauuuaca aucaaccgaa gaaguacccg caaaugaaaa uacugaaaau 240
aaucaacaug aaauugauga aauaacaaca acagaucaau cagaugauga aauuaacaca 300
ccaaacguug cagaagaaga aucacaagau gacuugaaag augauuuaaa agaaaagcaa 360
caaccaagug accaucauca auccacgcaa ccuaagacuu caccaucaac ugaaacaaac 420
aagcaacaau cauuugcuaa uuguaagcaa cuuagacaag uauauccgaa uggugucacu 480
gccgaucauc cagcauaucg accacauuua gauagagaua aagauaaacg ugcaugugaa 540
ccugauaaau auuaa 555

<210> SEQ ID NO 41
<211> LENGTH: 390
<212> TYPE: RNA
<213> ORGANISM: Staphylococcus aureus

<400> SEQUENCE: 41
augaagaaau uaaucaucag cauuauggcg aucaugcuau uuuuaacagg uugugguaaa 60
agccaagaga aagccacucu ggaaaaggau aucgauaauu uacaaaaaga aaauaaagaa 120
uuaaaagaua aaaaagaaaa gcuucaacaa gaaaaagaaa aauuagcaga uaagcaaaaa 180
gaccuugaaa aagaagugaa agauuuaaaa ccuucaaaag aagauaacaa ggacgauaaa 240
aaagacgaag acaaaaauaa agacaaagau aaagaggcau cacaagauaa gcaaucaaaa 300
gaucaaacua agucaucgga uaaagauaau cacaaaaagc cuacaucaac agauaaagau 360
caaaaagcua augacaaaca ccaaucauaa 390

<210> SEQ ID NO 42
<211> LENGTH: 2982
<212> TYPE: RNA
<213> ORGANISM: Staphylococcus aureus

<400> SEQUENCE: 42
augaagaacg cauuuaaauu auuuaaaaug gaucugaaga aaguagcuaa gacgccagcu 60
guguggauua ucuuagcagg cuuagcuauu uugccaucgu ucuacgcuug guuuaacuua 120
ugggcaaugu gggauccaua uggcaacacg ggacacauca aggucgcagu cguuaaugaa 180
gauaaaggcg acacaaucag agggaaaaaa guuaaugucg guaauacgau gguuaacaca 240
cucaagaaaa auaaaaguuu ugauuggcag uuuguaagua gagagaaagc ugaucaugag 300
auaaaaaugg guaaauauuu ugcagguauu uacaucccau cuaaguuuac acaugaaauu 360
accgggacac uacguaagca gccucaaaaa gcagauguag aauuuaaggu gaaucagaag 420
auuaacgcug uugcgucuaa gcuaacagau acugguucgu caguugucgu ugaaaaagcg 480
aaugaacaau uuaauaaaac aguaacucga gcauuauuag aagaagcuaa caaagcaggu 540

-continued

```
uuaacuauug aagaaaaugu gccgacaauu aauaagauaa aaaaugcggu auauucggca    600
gauaaagcuu uaccuaagau uaaugacuuu gcgaauaaaa uuguauauuu gaauaaccac    660
caagcggauu uagauaaaua ugcgaaugau uuuagaaaac uaggaaauua uaaaggugau    720
auuuuagaug cucagaaaaa auuaaacgaa gucaauggug cuauuccgca acuuaaugaa    780
aaggcuaagu ugauauuagc uuuaaauaau uauaugccga aaauugaaaa agcguuaaau    840
uuugcagcug augacgugcc agcgcaguuc ccuaaaauua aucaaggacu uaacauugcg    900
agucaaggua uugaucaagc uaauggacag uuaaaugaug ccaaaggcuu cgucacacaa    960
guuagaagua gagucggga uuaucaagaa gcaauucgac gcgcgcaaga uuugaaucga   1020
agaaaccagc aacagauucc ucaaaauagc gcggcgaaca acgaaacauc aaauagugca   1080
ccugcagcug guaaugugu aacaucaacg ccaccaagug caccaaaugg caauacuaca   1140
ccaaauaaua auguuacgca aaauaccgca ccaaauagua auaaugcacc uguaucgacu   1200
acaccacaaa guacaagcgg gaaaaaagau ggucaaaguu uugcagauau aacaacaaca   1260
caagucagca cagcuaacga gaacacacaa aauauuacag auaaagaugu uaaaucaaug   1320
gaagcggcau uaacgggcuc uuuauuauca uuaucaaaua auuuagauac ccaagcgaaa   1380
gccgcacaaa aagauaguca ggcauuacgu aauauuucgu auggcauuuu agcaucggac   1440
aagccaucug auuuuagaga gucuuuagau aauguuaagu ccgguuuaga auacacaacu   1500
caauauaauc aacaauuuau cgauacauua aaagagauug agaagaauga aaauguugau   1560
uuaucaaaag aaauugauaa gguaaagaca gcuaauaauc gaauuaauga aucauuaagg   1620
uuaguuaauc aauuaaguaa ugcauuaaag aaugguaguu caggaacugc ugaagcuacu   1680
aaauuacuag aucaacuguc aaaacuagau ucaucauuau caucauuuag agauuauguu   1740
aaaaaagauc uuaacagcuc uuuaguauca auaucacaac guauuaugga ugaauugaac   1800
aaagggcaaa cggcauuguc uaauguucag ucuaagcuaa auacaauuga ucaagucauc   1860
aacaguggucc aaucuauuuu aaaaaauggu aaaacacgua ucgaucguuu acaaacagua   1920
uuaccaagua uugaacaaca auacauuagu gcuauuaaaa augcucaagc aaacuucccg   1980
aaagugaaaa gugauguagc gaaagcagcu aacuuuguac guaacgauuu accacaguug   2040
gagcaacguu uaaccaaugc gacugcaagu gugaauaaaa auuuaccaac guuauuaaau   2100
gguuaugauc aagcgguagg auuacuaaau aaaaaucagc cacaagcgaa aaaggcuuua   2160
ucagauuuag cugauuuugc acaaaauaaa uugccagaug uugaaaaaga ucugaaaaaa   2220
gcgaauaaga uuuucaagaa guuagacaaa gacgaugcag ucgauaaauu aaucgacaca   2280
cuuaagaaug auuugaaaaa gcaagcgggu auuauugcaa auccuauuaa uaagaagacu   2340
guugauguuu ucccaguuaa ggauuaugga ucagggauga caccauucua uacugcauua   2400
ucgguauggg uaggcgcacu cuuaauggua agccuauuaa cuguugauaa uaaacauaag   2460
agcuuagagc caguguuaac gacacgacaa guauucuuag guaaagcagg auucuuuaua   2520
augcuuggua uguugcaagc acucauugua ucgguuggag auuuguuaau ccuaaaagca   2580
ggaguugagu caccuguauu auucguacuu auaacgauuu ucuguucgau uauuuucaac   2640
ucaaucguau auacgugcgu aucauuacuu gguaacccag guaaagccau ugcaaucgua   2700
uugcuuguau uacaaauugc agguggugga gguacauucc caauucaaac gacaccacaa   2760
uuuuuccaaa acauuucgcc auacuuacca uuuacguaug caauugauuc auuacgugaa   2820
acaguaggcg guauuguucc ggaaaucuua auuacaaaau uaauuauauu aacguuauuu   2880
ggcauaggau ucuucguugu agguuuaauu uuaaaaccug uaacagaucc auugaugaag   2940
```

cgcguaucug aaaaaguuga ccaaaguaac guuacagaau aa 2982

<210> SEQ ID NO 43
<211> LENGTH: 6201
<212> TYPE: RNA
<213> ORGANISM: Staphylococcus aureus

<400> SEQUENCE: 43
augaaugaaa aaguagaagg caugaccuug gagcugaaau uagaccauuu aggugucaa 60 gaaggcauga aagguuuaaa gcgacaauua gguguuguua auagugaaau gaaagcuaau 120
cugucagcau uugauaaguc ugaaaaauca auggaaaaau aucaggcgag aauuaagggg 180
uuaaaugaua ggcuuaaagu ucaaaaaaag auguauucuc aaguagaaga ugagcuuaaa 240
caaguuaacg cuaauuacca aaaagcuaaa uccaguguaa aagauguuga gaaagcauau 300
uuaaaguuag uagaagccaa uaaaaaagaa aaauuagcuc uugauaaauc uaaagaagcc 360
uuaaaaucau cgaauacaga acuuaaaaaa gcugaaaauc aauauaaacg uacaaaucaa 420
cguaaacaag augcguauca aaaacuuaaa caguugagag augcagaaca aaagcuuaag 480
aauaguaacc aagcuacuac ugcacaacua aaaagagcaa gugacgcagu acagaagcag 540
uccgcuaagc auaaagcacu uguugaacaa uauaaacaag aaggcaauca aguucaaaaa 600
cuaaaagugc aaaaugacaa ucuuucaaaa ucaaaugaua aaauugaaag uucuuacgcu 660
aaaacuaaua cuaaauuaaa gcaaacagaa aaagaauuua augauuuaaa caauacuauu 720
aagaaucaua gcgcuaaugu cgcaaaagcu gaaacagcug uuaauaaaga aaaagcugcu 780
uuaaauaauu uggagcguuc aauagauaaa gcuucauccg aaaugaagac uuuuaacaaa 840
gaacaaauga uagcucaaag ucauuucggu aaacuugcaa gucaagcgga ugucauguca 900
aagaaauuua guucuauugg agacaaaaug acuucccugg gacguacaau gacgaugggc 960
guaucuacac caauuacuuu aggguuaggu gcagcauuaa aaacaagugc agacuuugaa 1020
ggccaaaugu cucgaguugg agcgauugcg caagcaagca guaaagacuu gaaaagcaug 1080
ucuaaucaag caguugacuu aggagcuaaa accaguaaaa gugcuaacga aguugcuaaa 1140
gguauggaag aauuggcagc uuuaggcuuu aaugccaaac aaacaaugga ggcuaugcca 1200
gguguuauca gugcagcaga agcaaguggu gcagaaaugg cuacaacugc aacuguaaug 1260
gcuucagcga uuaacucuuu cgguuuaaaa gcaucugaug caaaucaugu ugcugauuua 1320
cuugcgagau cagcaaauga uagugcugca gauauucagu acaugggaga ugcauugaag 1380
uaugcuggua cuccugcaaa agcauuagga guuucaauag aggacacuuc cgcagcaauu 1440
gaaguuuuau cuaacucagg uuuagagggu ucucaagcag guacugcccu aagagcuuca 1500
uuuaucaggc uagcuaaucc aaguaaaaau acagcuaagg aaaugaaaaa auuagguauu 1560
cauuugucug augcuaaagg ucaauuuguu ggcaugggug aauugauuag acaguuccaa 1620
gauaauauga aaggcaugac gagagaacaa aaacuagcua caguggcuac aauaguuggu 1680
acugaagcag caaguggauu uuuagccuug auugaagcgg gaccagauaa aauuaauagc 1740
uauaguaaau ccuuaaagaa uuccaauggc gaaaguaaaa aagcagcaga uuugaugaaa 1800
gauaaucuca aaggcgcucu ggaacaauua gguggcgcuu uugaaucauu agcaaucgaa 1860
gucgguaaag auuuaacgcc uaugauuaga gcaggagcgg aagguuuaac aaaauuaguu 1920
gauggauuua cacaucuccc ugguuggguu agaaaagcuu caguaggauu agcacuuuuu 1980
ggugcaucua uuggcccugc uguucuugcu gguggcuuau uaauacgugc aguuggaagu 2040

-continued

```
gcugcuaaag gcuaugcauc auuaaauaga cgcauugcug aaaauacaau acugucuaau   2100
accaauucaa aagcaaugaa aucuuuaggu cuucaaaccu uauuucuugg uucuacaaca   2160
ggaaaaacgu caaaaggcuu uaaaggauua gccggagcua uguuguuuaa uuuaaaaccu   2220
auaaauguuu ugaaaaauuc ugcaaagcua gcaauuuuac cguucaaacu uuugaaaaac   2280
gguuuaggau uagccgcaaa auccuuauuu gcaguaagug gaggcgcaag auuugcuggu   2340
guagccuuaa aguuuuuaac aggaccuaua ggugcuacaa uaacugcuau uacaauugca   2400
uauaaaguuu uuaaaaccgc auaugaucgu guggaauggu ucagaaacgg uauuaacggu   2460
uuaggagaaa cuauaaaguu uuuuggugge aaaauuauug gcggugcugu uaggaagcua   2520
ggagaguuua aaaauuaucu uggaaguaua ggcaaaagcu ucaaagaaaa guuuucaaag   2580
gauaugaaag augguuauaa aucuuugagu gacgaugacc uucugaaagu aggagucaac   2640
aaguuuaaag gauuuaugca aaccaugggc acagcuucua aaaaagcauc ugauacugua   2700
aaaguguugg ggaaaggugu uucaaaagaa acagaaaaag cuuuagaaaa auacguacac   2760
uauucugaag agaacaacag aaucauggaa aaaguacguu uaaacucggg ucaaauaaca   2820
gaagacaaag caaaaaaacu uuugaaaauu gaagcggauu uaucuaauaa ccuuauagcu   2880
gaaauagaaa aaagaaauaa aaaggaacuc gaaaaaacuc aagaacuuau ugauaaguau   2940
agugcguucg augaacaaga aaagcaaaac auuuuaacua gaacuaaaga aaaaaaugac   3000
uugcgaauua aaaaagagca agaacucaau cagaaaauca aagaauugaa agaaaaagcu   3060
uuaagugaug gucagauuuc agaaaaugaa agaaaagaaa uugaaaagcu ugaaaaucaa   3120
agacgugaca ucacuguuaa agaauugagu aagacugaaa aagagcaaga gcguauuuua   3180
guaagaaugc aaagaaacag aaauucuuau ucaauagacg aagcgagcaa agcaauuaaa   3240
gaagcagaaa aagcaagaaa agcaaaaaaa aaagaagugg acaagcaaua ugaagaugau   3300
gucauugcua uaaaaaauaa cgucaaccuu ucuaagucug aaaaagauaa auuauuagcu   3360
auugcugauc aaagacauaa ggaugaagua agaaaggcaa aaucuaaaaa agaugcugua   3420
guagacguug uuaaaaagca aaauaaagau auugauaaag agauggauuu auccaguggu   3480
cguguauaua aaaauacuga aaaauggugg aauggccuua aaaguuggug gucuaacuuc   3540
agagaagacc aaaagaagaa aagugauaag uacgcuaaag aacaagaaga aacagcucgu   3600
agaaacagag aaaauauaaa gaaaugguuu ggaaaugcuu gggacggcgu aaaaaguaaa   3660
acuggcgaag ccuuuaguaa aaugggcaga aaugcuaauc auuuuggcgg cgaaaugaaa   3720
aaaaugugga guggaaucaa aggaauucca agcaaauuaa guucagguug gagcucagcc   3780
aaaaguucug uaggauauca cacuaaggcu auagcuaaua guacugguaa augguuugga   3840
aaagcuuggc aaucuguuaa aucgacuaca ggaaguauuu acaaucaaac uaagcaaaag   3900
uauucagaug ccucagauaa agcuugggcg cauucaaaau cuauuuggaa agggacauca   3960
aaauguuua gcaaugcaua uaaaagugca aagggcuggc uaacggauau ggcuaauaaa   4020
ucgcgcucga aaugggauaa uauuucuagu acagcauggu cgaaugcaaa auccguuugg   4080
aaaggaacau cgaaaugguu uaguaacuca uacaaaucuu uaaaagguug gacuggagau   4140
auguauucaa gagcccacga ucguuuugau gcaauuucaa guucggcaug gucuaacgcu   4200
aaaucaguau uuaaugguuu uagaaaaugg cuaucaagaa cauaugaaug gauuagagau   4260
auugguaaag acaugggaag agcugcggcu gauuuaggua aaaauguugc uaauaaagcu   4320
auuggcgguu ugaauagcau gauuggcggu auuaauaaaa uaucuaaagc cauuacugau   4380
aaaaaucuca ucaagccaau accuacauug ucuacuggua cuuuagcagg aaagggugua   4440
```

gcuaccgaua auucgggagc auuaacgcaa ccgacauuug cuguauuaaa ugauagaggu 4500
ucuggaaacg ccccaggcgg uggaguucaa gaaguaauuc acagggcuga cggaacauuc 4560
caugcacccc aaggacgaga ugugguuguu ccacuaggag uuggagauag uguaauaaau 4620
gccaaugaca cucugaaguu acagcggaug gguguuuugc caaaauucca uggugguacg 4680
aaaaagaaaa aauggaugga acaaguuacu gaaaaucuug guaaaaaagc aggggacuuc 4740
gguucuaaag cuaaaaacac agcucauaau aucaaaaaag gugcagaaga aaugguugaa 4800
gccgcaggcg auaaaaucaa agauggugca ucuugguuag gcgauaaaau cggcgaugug 4860
ugggauuaug uacaacaucc agggaaacua guaaauaaag uaaugucagg uuuaaauauu 4920
aauuuuggag gcggagcuaa cgcuacagua aaaauugcua aaggcgcgua cucauugcuc 4980
aaaaagaaau uaguagacaa aguaaaaucg ugguuugaag auuuuggugg uggaggcgau 5040
ggaagcuauc uauuugacca uccaauuugg caaagguuug ggagcuacac agguggacuu 5100
aacuuuaaug gcggucguca cuaugguauc gacuuucaaa ugccuacugg aacgaacauu 5160
uaugcuguua aaggcgguau agcugauaaa guauggacug auuacggugg cgguaauucu 5220
auacaaauua agaccggugc uaacgaaugg aacugguaua ugcauuuauc uaagcaauua 5280
gcaagacaag gccaacguau uaaagcuggu caacugauag ggaaaucagg ugcuacaggu 5340
aauuucguua gaggagcaca cuuacauuuc caauugaugc aagggucgca uccagggaau 5400
gauacagcua aagauccaga aaaaugguug aagucacuua aagguagugg cguucgaagu 5460
gguucaggug uuaauaaggc ugcaucugcu ugggcaggcg auauacgucg ugcagcaaaa 5520
cgaaugggug uuaauguuac uucgggugau guaggaaaua uuauuagcuu gauucaacac 5580
gaaucaggag gaaaugcagg uauaacucaa ucuagugcgc uuagagacau caacguuuua 5640
cagggcaauc cagcaaaagg auugcuucaa uauaucccac aaacauuuag acauuaugcu 5700
guuagagguc acaacaauau auauagugguu uacgaucagu uauuagcguu cuuuaacaac 5760
agcuauuggc gcucacaguu uaacccaaga ggugguuggu cuccaagugg uccaagaaga 5820
uaugcgaaug gugguuugau uacaaagcau caacuugcug aagugggguga aggagauaaa 5880 caggagaugg uuaucccuuu aacuagacgu aaacgagcaa uucaauuaac ugaacagguu 5940
augcgcauca ucgguaugga uggcaagcca aauaacauca cuguaaauaa ugauacuuca 6000
acaguugaaa aauuguugaa acaaauuguu auguuaagug auaaaggaaa uaaauuaaca 6060
gaugcauuga uucaaacugu uucuucucag gauaauaacu uagguucuaa ugaugcaauu 6120
agagguuuag aaaaaauauu gucaaaacaa agugggcaua gagcaaaugc aaauaauuau 6180
augggagguu ugacuaauua a 6201

<210> SEQ ID NO 44
<211> LENGTH: 1830
<212> TYPE: RNA
<213> ORGANISM: Staphylococcus aureus

<400> SEQUENCE: 44
augaaaaagc aaauaauuuc gcuaggcgca uuagcaguug caucuagcuu auuuacaugg 60
gauaacaaag cagaugcgau aguaacuaaa gauuauagua aagaaucaag agugaaugag 120
aacaguaaau acgauacacc aauuccagau ugguaucuag guaguauuuu aaacagauua 180
ggggaucaaa uauacuacgc uaaggaauua acuaauaaau acgaauaugg ugagaaagag 240
uauaagcaag cgauagauaa auugaugacu agaguuuugg gagaagauca uuaucuauua 300

```
gaaaaaaaga aagcacaaua ugaagcauac aaaaaauggu uugaaaaaca uaaaagugaa    360

aauccacauu cuaguuuaaa aaagauuaaa uuugacgauu uugauuuaua uagauuaacg    420

aagaaagaau acaaugaguu acaucaauca uuaaaagaag cuguugauga guuuaauagu    480

gaagugaaaa auauucaauc uaaacaaaag gauuuauuac cuuaugauga agcaacugaa    540

aaucgaguaa caaauggaau auaugauuuu guuugcgaga uugacacauu auacgcagca    600

uauuuuaauc auagccaaua uggucauaau gcuaaagaau uaagagcaaa gcuagauaua    660

auucuuggug augcuaaaga uccuguuaga auuacgaaug aaagaauaag aaaagaaaug    720

auggaugauu uaaauucuau uauugaugau uucuuuaugg auacaaacau gaauagacca    780

uuaaacauaa cuaaauuuaa uccgaauauu caugacuaua cuaauaagcc ugaaaauaga    840

gauaacuucg auaaauuagu caaagaaaca agagaagcaa ucgcaaacgc ugacgaaucu    900

uggaaaacaa gaaccgucaa aaauuacggu gaaucugaaa caaaaucucc uguuguaaaa    960

gaagagaaga aaguugaaga accucaauua ccuaaaguug gaaaccagca agaggauaaa   1020

auuacaguug guacaacuga agaagcacca uuaccaauug cgcaaccacu aguuaaaauu   1080

ccacagggca caauucaagg ugaaauugua aaagguccgg aauaucuaac gauggaaaau   1140

aaaacguuac aaggugaaau cguucaaggu ccagauuucc caacaaugga acaaaacaga   1200

ccaucuuuaa gcgauaauua uacucaaccg acgacaccga acccuauuuu aaaagguauu   1260

gaaggaaacu caacuaaacu ugaaauaaaa ccacaaggua cugaaucaac guuaaaaggu   1320

acucaaggag aaucaaguga uauugaaguu aaaccucaag caacugaaac aacagaagca   1380

ucacauuauc cagcgagacc ucaauuuaac aaaacaccua aguaugugaa auauagagau   1440

gcugguacag guauccguga auacaacgau ggaacauuug gauaugaagc gagaccaaga   1500

uucaacaagc caagcgaaac aaaugcauac aacguaacga caaaucaaga uggcacagua   1560

ucauauggcg cucgcccgac acaaaacaag ccaagcgaaa caaacgcaua uaacguaaca   1620

acacaugcaa acggccaagu aucauacgga gcucguccga cacaaaacaa gccaagcgaa   1680

acgaacgcau auaacguaac aacacaugca aacggucaag ugucauacgg agcucgccca   1740

acacaaaaca agccaaguaa aacaaaugca uacaauguaa caacacaugc agaugguacu   1800

gcgacauaug guccuagagu aacaaaauaa                                    1830
```

<210> SEQ ID NO 45
<211> LENGTH: 435
<212> TYPE: RNA
<213> ORGANISM: Staphylococcus aureus

<400> SEQUENCE: 45

```
augaaaaaag uaaucggacu gcuacuagua aguacauuag cuuuaacagc uuguggugaa     60

aaagaaaaac caaaaaaaga agaaaauaaa aagucacaaa cacaaaaaca caaagauagc    120

aaaccaaaaa cgcaacaaga aaaaaugaaa aaaguugaag auaaaaaauc accuaauaau    180

agcauacaaa auaaauucaaa caaucaaaac caaucacaaa acaaucaacu uaauaauaau    240

ucagauccau cuaauaauac uccugcaaau auaaauaaaa acgauucaca aaauacuaau    300

uuaaaugaug aguaugucgu uucgccuggc uggacuaaag augaacaggc uaaagcuuuu    360

gaagaguaca aaaaaggaaa agaagacgaa gcaagagcug gugcuagcgc aguaccagga    420

gccaauauua acuaa                                                    435
```

<210> SEQ ID NO 46
<211> LENGTH: 3774

<212> TYPE: RNA
<213> ORGANISM: Staphylococcus aureus

<400> SEQUENCE: 46

```
auggcgaaaa aauuuaauua caaacuacca ucaaugguug cauuaacgcu uguagguuca      60
gcagucacug cacaucaagu ucaagcagcu gagacgacac aagaucaaac uacuaauaaa     120
aauguuuuag auaguaauaa aguuaaagca acuacugaac aagcaaaagc ugagguaaaa     180
aauccaacgc aaaacauuuc uggcacucaa guauaucaag acccugcuau uguccaacca     240
aaagcagcga auaaaacagg caaugcucaa guaaaucaaa agguugauac uacacaagua     300
aauggugaca cucgugcgac ucaaucaacu acaucaaaua augcgaaacc uguuacaaag     360
ucaacaaaca caacagcacc uaaaacgaac aauaauguua caagugcugg auauaguuua     420
guugaugaug aagaugauaa uucagaaaau caaauuaauc cagaauuaau uaaaucagcu     480
gcuaaaccug cugcucuuga aacgcaauau aaagccgcag caccaaaagc aacaccuguu     540
gcaccuaaag cuaaaacuga agcuacacca aaaguaacua cuuuuagugc uucagcacaa     600
ccaagaucag ccgcugcagc accuaaaacg aguuugccaa aauauaaacc gcaaguaaac     660
ucaucaauua augauuacau ucguaaaaau aauuuaaaag caccuaagau agaggaagau     720
uauacaucuu acuucccuaa auacgcauac cguaacggug uaggucgucc ugaagguauc     780
guuguucaug auacagcuaa ugaucguucg acgauaaaug gcgaaauuag uuauaugaaa     840
aacaacuauc aaaacgcauu cguacaugca uuuguugaug gggaucguau aaucgaaaca     900
gcaccaacgg auuacuuauc uuggggguguc ggugcagucg guaacccuag auucaucaau     960
guugaaaucg ugcacacaca cgauuaugcu ucauuugcac guucaaugaa uaacuaugcu    1020
gacuaugcag cuacacaauu acaauauuau gguuuaaaac cugauagugc ugaauaugau    1080
ggaaauggua caguauggac ucacuacgcu guaaguaaau auuuaggugg uacggaccau    1140
gccgauccac auggauauuu aagaagucau aauuauaguu augaucaacu auaugacuua    1200
auuaaugaaa aauauuuaau aaaaaugggu aaaguggcgc caugggguac gcaaucuaca    1260
acuaccccua cuacaccauc aaaaccauca acaccgucga aaccaucaac accaucaacu    1320
gguaaauuaa caguugcugc uaauaauggu gucgcacaaa ucaaaccuac aaauaguggu    1380
uuauauacua cuguuuacga caaaacuggu aaagcaacua augaaguuca aaaaacauuu    1440
gcuguaucua aaacagcuac auuagguaau caaaaauucu aucuuguuca agauuacaau    1500
ucugguaaua aauuugguug gguuaaagaa ggcgaugugg uuuacaacac agcuaaauca    1560
ccuguaaaug uaaaucaauc auauucaauc aaaccuggua cgaaacuuua uacaguaccu    1620
ugggguacau cuaaacaagu ugcugguagc gugucugguu cuggaaacca aacauuuaag    1680
gcuucaaagc aacaacaaau ugauaaauca auuuauuuau auggcucugu gaaugguaaa    1740
ucugguuggg uaaguaaagc auauuuaguu gauacugcua aaccuacgcc uacaccaaca    1800
ccuaagccau caacaccuac aacaaauaau aaauuaacag uuucaucauu aaacggugu u   1860
gcucaaauua augcuaaaaa caauggcuua uucacuacag uuuaugacaa aacugguaag    1920
ccaacgaaag aaguucaaaa aacauuugcu guaacaaaag aagcaagucu agguggaaac    1980
aaauucuacu uaguuaaaga uuacaauagu ccaacuuuaa uugguugggu uaaacaaggu    2040
gacguuauuu auaacaaugc aaaaucaccu guaaauguaa ugcaaacuua uacaguaaaa    2100
ccaggcacua aauuauauuc aguaccuugg gguacuuaua aacaagaagc uggugcggua    2160
ucugguacag guaaccaaac uuuuaaagcg acuaagcaac aacaaauuga uaaaucuauc    2220
```

-continued

```
uauuuauaug gaacuguaaa ugguaaaucu gguuggauaa guaaagcaua uuuagcugua   2280
ccugcugcac cuaaaaaagc uguagcacaa ccaaaaacug cuguaaaagc uuaugcuguu   2340
acuaaaccuc aaacgacuca aacaguuagc aaaauugcuc aaguuaaacc aaacaacacu   2400
gguauucgug cuucuguuua ugaaaaaaca gcgaaaaacg gugcaaaaua ugcggaucgu   2460
acauucuaug uaacaaaaga acgugcacau gguaaugaaa cauacguauu auuaaauaau   2520
acaagucaua auauuccauu agguugguuc aauguaaaag acuuaaaugu ucaaaacuua   2580
ggcaaagaag uuaaaacgac ucaaaaauau acuguuaaca gaucaaauaa cggcuuauca   2640
augguuccuu gggguacuaa aaaccaaguc auuuuaacag gcaauaacau ugcucaaggu   2700
acauuuaaug caacgaaaca aguaucugua ggcaaagaug uuuauuuaua cgguacuauu   2760
aauaaccgca cugguugggu aaauucaaaa gauuuaacug caccaacugc uguuaaacca   2820
acuacaucag cugccaaaga uuauaacuac acuuauguaa uuaaaaaugg uaaugguuau   2880
uacuauguaa caccaaauuc ugauacagcu aaauacucau uaaaagcauu uaaugaacaa   2940
ccauucgcag uuguuaaaga acaagucauu aauggacaaa cuugguacua ugguaaauua   3000
ucuaacggua aauuagcaug gauuaaauca acugauuuag cuaaagaauu aauuaaguau   3060
aaucaaauag guaugacauu aaaccaaguu gcucaaauac aagcugguuu acaauauaaa   3120
ccacaaguac aacguguacc agguaagugg acagaugcua acuuuaauga uguuaagcau   3180
gcaauggaua cgaagcguuu agcucaagau ccagcauuaa aauaucaauu cuuacgcuua   3240
gaccaaccac aaaauauuuc uauugauaaa auuaaucaau ucuuaaaagg uaaaggugua   3300
uuagaaaacc aaggugcugc auuuaacaaa gcugcucaaa uguauggcau uaaugaaguu   3360
uaucuuaucu cacaugcccu auuagaaaca gguaacggua cuucucaauu agcaaaaggu   3420
gcagauguag ugaacaacaa aguuguaacu aacucuaaca cgaaauacca uaacguauuu   3480
gguauugcug cauaugauaa cgauccuuua cgugaaggua uuaaauaugc uaaacaagcu   3540
gguugggaca caguaucaaa agcaaucguu gguggugcua aauucaucgg caacucauau   3600
guuaaagcug gucaaaauac gcuuuacaaa augagaugga auccugcaca uccaggaaca   3660
caccaauaug cuacagaugu agauugggcu aacaucaaug cuaaaaucau caaaggcuac   3720
uaugauaaaa uuggcgaagu cggcaaauac uucgacaucc cacaauauaa auaa         3774
```

<210> SEQ ID NO 47
<211> LENGTH: 1461
<212> TYPE: RNA
<213> ORGANISM: Staphylococcus aureus

<400> SEQUENCE: 47

```
augucuaaua auuuuaaaga ugacuuugaa aaaaaucguc aaucgauaga cacaaauuca     60
caucaagacc auacggaaga uguugaaaaa gaccaaucag aauuagaaca ucaggauaca    120
auagagaaua cggagcaaca guuuccgcca agaaaugccc aaagaagaaa aagacgccgu    180
gauuuagcaa cgaaucauaa uaaacaaguu cacaaugaau cacaaacauc ugaagacaau    240
guucaaaaug aggcuggcac aauagaugau cgucaagucg aaucaucaca caguacugaa    300
agucaagaac cuagccauca agacaguaca ccucaacaug aagagggaua uuauaauaag    360
aaugcuuuug caauggauaa aucacaucca gaaccaaucg aagacaauga uaaacacgag    420
acuauuaaag aagcagaaaa uaacacugag cauucaacag uuucugauaa gagugaagcu    480
gaacaaucuc agcaaccuaa accauauuuu gcaacaggug cuaaccaagc aaauacauca    540
aaagauaaac augaugaugu aacuguuaag caagacaaag augaaucuaa agaucaucau    600
```

-continued

```
aguggua aaa aaggcgcagc aauuggugcu ggaacagcgg guguugcagg ugcagcuggu    660
```

agugguaaaa aaggcgcagc aauuggugcu ggaacagcgg guguugcagg ugcagcuggu 660
gcaaugggug uuucuaaagc uaagaaacau ucaaaugacg cucaaaacaa aaguaauucu 720
ggcaagguga auaacucgac ugaggauaaa gcgucugaag acaagucaaa agaacaucau 780
aaugguaaaa aaggugcagc aaucggugcu ggaacagcag guuuggcugg aggcgcagca 840
aguaauagug cuucugccgc uucaaaacca caugccucua auaaugcaag ucaaaacaau 900
gaugaacaug accaucauga cagagauaaa gaacguaaaa aagguggcau ggccaaagua 960
uuguuaccau uaauugcagc uguacuaauu aucggugcau uagcgauauu uggaggcaug 1020
gcauuaaaca aucauaauaa ugguacaaaa gaaaauaaaa ucgcgaauac aaauaaaaau 1080
aaugcugaug aaaguaaaga uaaagacaca ucuaaagacg cuucuaaaga uaaaucaaaa 1140
ucuacagaca gugauaaauc aaaagaugau caagacaaag cgacuaaaga ugaaucugau 1200
aaugaucaaa acaacgcuaa ucaagcgaac aaucaagcac aaaauaauca aaaucaacaa 1260
caagcuaauc aaaaucaaca acagcaacaa caacgucaag gugguggcca aagacauaca 1320
gugaaugguc aagaaaacuu auaccguauc gcaauucaau acuacgguuc agguucaccg 1380
gaaaauguug aaaaaauuag acgugccaau gguuuaagug guaacaauau uagaaacggu 1440
caacaaaucg uuauuccaua a 1461

<210> SEQ ID NO 48
<211> LENGTH: 3825
<212> TYPE: RNA
<213> ORGANISM: Staphylococcus aureus

<400> SEQUENCE: 48
augagcuggu uugauaaauu auucggcgaa gauaaugauu caaaugauga cuugauucau 60
agaaagaaaa aaagacguca agaaucacaa aauauagaua acgaucauga cucauuacug 120
ccucaaaaua augauauuua uagucguccg aggggaaaau uccguuuucc uaugagcgua 180
gcuuaugaaa augaaaaugu ugaacaaucu gcagauacua uuucagauga aaaagaacaa 240
uaccaucgag acuaucgcaa acaaagccac gauucucguu cacaaaaacg acaucgccgu 300
agaagaaauc aaacaacuga agaacaaaau uauagugaac aacgugggaa uucuaaaaua 360
ucacagcaaa guauaaaaua uaaagaucau ucacauuacc auacgaauaa gccagguaca 420
uauguuucug caauuaaugg uauugagaag gaaacgcaca agucaaaaac acacaauaua 480
uauucuaaua auacaaauca ucgugcuaaa gauucaacua cagauuauca caaagaaagu 540
uucaagacuu cagagguacc gucagcuauu uuuggcacaa ugaaaccuaa aaaguuagaa 600
aauggucgua ucccuguaag uaaaucuuca gaaaaaguug agucagauaa acaaaaauau 660
gauaaauaug uagcuaagac gcaaacgucu caaaauaaac auuuagaaca agagaaacaa 720
aaagauagug uugucaagca aggaacugca ucuaaaucau cugaugaaaa uguaucauca 780
acaacaaaau caacaccuaa uuauucaaaa guugauaaua cuaucaaaau ugaaaacauu 840
uaugcuucac aaauuguuga agaaauuaga cgugaacgag aacguaaagu gcuucaaaag 900
cgucgauuua aaaaagcguu gcaacaaaag cgugaagaac auaaaaaacga agagcaagau 960 gcaauacaac gugcaauuga ugaaauguau gcuaaacaag cggaacgcua uguuggugau 1020
aguucauuaa augaugauag ugacuuaaca gauaauagua cagaggcuag ucagcuucau 1080
acaaaugaaa uagaggauga agcuguauca aaugaugaaa auaaaaaagc gucaauacaa 1140
aaugaagaca cugaugacac ucauguagau gaaaguccau acaauuauga ggaaguuagu 1200

-continued

```
uugaaucaag uaucgacaac aaaacaauug ucagaugaug aaguuacggu uucggaugua   1260
acgucucaac gucaaucagc acugcaacau aacguugaag uaaauaauca agaugaacua   1320
aaaaaucaau ccagauuaau ugcugauuca gaagaagaug gagcaacgaa ugaagaagaa   1380
uauucaggaa gucaaaucga ugaugcagaa uuuuaugaau uaaaugauac agaaguagau   1440
gaggauacua cuucaaauag cgaagauaau accaauagag acgcgucuga aaugcaugua   1500
gacgcuccua aaacgcaaga gcacgcagua acugaaucuc aaguuaauaa uaucgauaaa   1560
acgguugaua augaaauuga auuagcgcca cgucauaaaa aagaugacca aacaaacuua   1620
agugucaacu cauugaaaac gaaugaugug aaugaugguc auguugugga agauucaagc   1680
augaaugaaa uagaaaagca aaacgcagaa auuacagaaa augugcaaaa cgaagcagcu   1740
gaaaguaaac aaaaugucga agagaaaacu auugaaaacg uaaauccaaa gaaacagacu   1800
gaaaagguuu caacuuuaag uaaaagacca uuuaauguug ucaugacgcc aucugauaaa   1860
aagcguauga uggaucguaa aaagcauuca aaagucaaug ugccugaauu aaagccugua   1920
caaaguaaac aagcugcgag ugaaagcaag acugcgacuc aaaacacacc aucaucaagu   1980
acugauucac aagagucaaa cacgaaugca uauaaaacaa auaauaugac aucaaacaau   2040
guugagaaca aucaacuuau uggucaugca gcaacagaaa augauuauca aaaugcacaa   2100
caauauucag agcagaaacc uucugcugau ucaacucaaa cggaaauauu ugaagaaagc   2160
caagaugaua aucaauugga aaaugagcaa guugaucaau caacuucguc uucaguuuca   2220
gaaguaagcg acauaacuga agaaagcgaa gaaacaacac aucaaaacaa uacuagugga   2280
caacaagaua augaugauca acaaaaagau uuacagcuuu cauuuucaaa ucaaaaugaa   2340
gauacagcua augaaaauag accucggacg aaucaaccag auguugcaac aaaucaagcu   2400
guacaaacuu cuaagccgau gauucguaaa ggcccaaaua uuaaauugcc aaguguuuca   2460
uuacuagaag aaccacaagu uauugagccg gacgaggacu ggauuacaga uaaaaagaaa   2520
gaacuuaaug acgcauuauu uuacuuuaau guaccugcag aaguacaaga uguaacugaa   2580
gguccaagug uuacaagauu ugaauuauca guugaaaaag guguuaaagu uucaagaauu   2640
acggcauuac aagaugacau uaaaauggca uuggcagcga aagauauucg uauagaagcg   2700
ccaauuccag gaacuagucg uguugguauu gaaguuccga accaaaaucc aacgacgguc   2760
aacuuacguu cuauuauuga aucuccaagu uuuaaaaaug cugaaucuaa auuaacaguu   2820
gcgaugggu auagaauuaa uaaugaacca uuacuuaugg auauugcuaa aacgccacac   2880
gcacuaauug cagguguaac uggaucaggg aaaucaguuu guaucaauag uauuuugaug   2940
ucuuuacuau auaaaaauca uccugaggaa uuaagauuau uacuuauuga uccaaaaaug   3000
guugaauuag cuccuuauaa ugguuugcca cauuuaguug caccgguaau uacagauguc   3060
aaagcagcua cacagaguuu aaaaugggcc guagaagaaa uggaaagacg uuauaaguua   3120
uuugcacauu accauguacg uaauauaaca gcauuuaaca aaaaagcacc auaugaugaa   3180
agaaugccaa aaauugucau aguaauugau gaguuggcug auuuaaugau gauggcuccg   3240
caagaaguug agcagucuau ugcuagaauu gcucaaaaag cgagagcaug ugguauucau   3300
auguugguag cuacgcaaag accaucuguc aauguaauua cagguuuaau uaaagccaac   3360
auaccaacaa gaauugcauu uaugguauca ucaaguguag auucaagaac gauauuagac   3420
agugguggag cagaacgcuu guuaggauau ggcgauaugu uauaucuugg uagcgguaug   3480
aauaaaccga uuagaguuca agguacauuu guuucugaug acgaaauuga ugauguuguu   3540
gauuuuauca aacaacaaag agaaccggac uaccuauuug aagaaaaaga auuguugaaa   3600
```

aaaacacaaa cacaaucaca agaugaauua uuugaugaug uuugugcauu uaugguuaau 3660
gaaggacaua uuucaacauc auuaauccaa agacauuucc aaauuggcua uaauagagca 3720
gcaagaauua ucgaucaauu agagcaacuc gguuauguuu cgagugcuaa ugguucaaaa 3780
ccaagggaug uuuauguuac ggaagcagau uuaaauaaag aauaa 3825

<210> SEQ ID NO 49
<211> LENGTH: 630
<212> TYPE: RNA
<213> ORGANISM: Staphylococcus aureus

<400> SEQUENCE: 49
augucgaauc aaaauuacga cuacaauaaa aaugaagaug gaaguaagaa gaaaaugagu 60
acaacagcga aaguaguuag cauugcgacg guauugcuau uacucggagg auuaguauuu 120
gcaauuuuug cauauguaga ucauucgaau aaagcuaaag aacguauguu gaacgaacaa 180
aagcaggaac aaaaagaaaa gcgucaaaaa gaaaaugcag aaaaagagag aaagaaaaag 240
caacaagagg aaaaagagca gaaugagcua gauucacaag caaaccaaua ucagcaauug 300
ccacagcaga aucaauauca auaugugcca ccucagcaac aagcaccuac aaagcaacgu 360
ccugcuaaag aagagaauga ugauaaagca ucaaaggaug agucgaaaga uaaggaugac 420
aaagcaucuc aagauaaauc agaugauaau cagaagaaaa cugaugauaa uaaacaacca 480
gcucagccua aaccacagcc gcaacaacca acaccaaagc caaauaauaa ucaacaaaac 540
aaucaaucaa aucaacaagc gaaaccacaa gcaccacaac aaaauagcca aucaacaaca 600
aauaaacaaa auaaugcuaa ugauaaguag 630

<210> SEQ ID NO 50
<211> LENGTH: 573
<212> TYPE: RNA
<213> ORGANISM: Staphylococcus aureus

<400> SEQUENCE: 50
augaaauuaa aaucauuagc aguguuauca augucagcgg uggugcuuac ugcauguggc 60
aaugauacuc caaaagauga aacaaaauca acagagucaa auacuaauca agacacuaau 120
acaacaaaag auguuauugc auuaaaagau guuaaaacaa gcccagaaga ugcugugaaa 180
aaagcugaag aaacuuacaa aggccaaaag uugaaaggaa uuucauuuga aaauucuaau 240
ggugaauggg cuuauaaagu gacacaacaa aaaucuggug aagagucaga aguacuuguu 300
gaugauaaaa auaaaaaagu gauuaacaaa aagacugaaa aagaagauac agugaaugaa 360
aaugauaacu uuaaauauag cgaugcuaua gauuacaaaa aagccauuaa agaaggacaa 420
aaggaauuug auggugauau uaaagaaugg ucacuugaaa aagaugaugg uaaacuuguu 480
uacaauaucg auuugaaaaa agguaauaaa aaacaagaag uuacuguuga ugcuaagaac 540
gguaaaguau uaaagaguga gcaagaucaa uaa 573

<210> SEQ ID NO 51
<211> LENGTH: 3030
<212> TYPE: RNA
<213> ORGANISM: Staphylococcus aureus

<400> SEQUENCE: 51
augaaaaaga aaaauuggau uuaugcauua auugucacuu uaauuauuau aauugccaua 60
guuaguauga uauuuuuugu ucaaacaaaa uauggagauc aaucagaaaa aggaucccaa 120

```
aguguaagua auaaaaauaa uaaaauacau aucgcaauug uuaacgagga ucaaccaacg    180
acauauaacg guaaaaaggu ugagcugggu caagcauuua uuaaaagguu agcaaaugag    240
aaaaacuaua aauuugaaac aguaacaaga aacguugcug agucugguuu gaaaaauggc    300
ggauaccaag ucaugauugu uaucccagaa aacuuuucaa aauuggcaau gcaauuagac    360
gcuaaaacac caucgaaaau aucacuacag uauaaaacag cuguaggaca aaaagaagaa    420
guagcuaaaa acacagaaaa aguuguaagu aauguacuua acgacuuuaa caaaaacuug    480
gucgaaauuu auuuaacaag caucauugau aauuuacaua augcacaaaa aaauguuggc    540
gcuauuauga cgcgugaaca uggugugaau aguaaauucu cgaauuacuu auuaaaucca    600
auuaacgacu ucccggaauu auuuacagau acgcuuguaa auucgauuuc ugcaaacaaa    660
gauauuacaa aaugguucca aacauacaau aaaucauuac ugagugcgaa uucagauaca    720
uucagaguga acacagauua uaauguuucg acuuuaauug aaaaacaaaa uucauuauuu    780
gacgaacaca auacagcgau ggauaaaaug uuacaagauu auaaaucgca aaaagauagc    840
guggaacuug auaacuauau caaugcauua aaacagaugg acagccaaau ugaucaacaa    900
ucaaguaugc aagauacagg uaaagaagaa uauaaacaaa cuguuaaaga aaacuuagau    960
aaauuaagag aaaucauuca aucacaagag ucaccauuuu caaaagguau gauugaagac   1020
uaucguaagc aauuaacaga aucacuccaa gaugagcuug caaacaacaa agacuuacaa   1080
gaugcgcuaa auagcauuaa aaugaacaau gcucaauucg cugaaaacuu agagaaacaa   1140
cuucaugaug auauugucaa agaaccugau ucagauacaa cauuuaucua uaacaugucu   1200
aaacaagacu uuauagcugc agguuuaaau gaggaugaag cuaauaaaua cgaagcaauu   1260
gucaaagaag caaaacguua uaaaaacgaa uauaauuuga aaaaaccguu agcagaacac   1320
auuaauuuaa cagauuacga uaaccaaguu gcgcaagaca caaguaguuu gauuaaugau   1380
ggugugaaag ugcaacguac ugaaacgauu aaaaguaaug auauuaauca auuaacuguu   1440
gcaacagauc cucauuuuaa uuuugaaggc gacauuaaaa uuaaugguaa aaaauaugac   1500
auuaaggauc aaaguguuca acucgauaca ucuaacaagg aauauaaagu ugaagucaau   1560
ggcguugcua aauugaaaaa ggaugcugag aaagauuucu uaaaagauaa aacaaugcau   1620
uuacaauugu uauuuggaca agcaaaucgu caagaugaac caaaugauaa gaaagcaacg   1680
aguguugugg auguaacauu gaaucauaac cuugaugguc gcuuaucgaa agaugcauua   1740
agccagcaau ugagugcauu aucuagguuu gaugcgcauu auaaaaugua cacagauaca   1800
aaaggcagag aagauaaacc auucgacaac aaacguuuaa uugauaugau gguugaccaa   1860
guuaucaaug acauggaaag uuucaaagac gauaaaguag cuguguuaca ucaaauugau   1920
ucaauggaag aaaacucaga caaacugauu gaugacauuu uaaauaacaa aaagaauaca   1980
acaaaaaaua aagaagauau uucuaagcug auugaucagu uagaaaacgu uaaaaagacu   2040
uuugcugaag agccacaaga accaaaaauu gauaaaggca aaaaugauga auuuaauacg   2100
augucuucaa auuuagauaa agaaauuagu agaauuucug agaaaaguac gcaauugcua   2160
ucagauacac aagaaucaaa aacaauugca gauucaguua guggacaauu aaaucaauua   2220
gauaauaaug ugaauaaacu acaugcgaca ggucgagcau uaggcguaag agcgaaugau   2280
uugaaccguc aaauggcuaa aaacgauaaa gauaaugagu uauucgcuaa agaguuuaaa   2340
aaaguauuac aaaauucuaa agauggcgac agacaaaacc aagcauuaaa agcauuuaug   2400
aguaauccgg uucaaaagaa aaacuuagaa aauguuuuag cuaauaaugg uaauacagac   2460
gugauuucac cgacauuguu cguauuauug auguauuuac uaucaaugau uacagcauau   2520
```

-continued auuuucuaua gcuaugaacg ugcuaaagga caaaugaauu ucaucaaaga ugauuauagu 2580
aguaaaaaca aucuuuggaa uaaugcgauu acgucuggug uuauuggugc aacugguuua 2640
guagaaggau uaauugucgg uuuaauugca augaauaagu uccauguauu agcuggcuau 2700
agagcgaaau ucaucuuaau ggugauuuua acuaugaugg ucuucguacu uauuaauacg 2760
uauuuacuaa gacagguaaa aucuaucggu auguucuuaa ugauugcugc auugggucua 2820
uacuuuguag cuaugaauaa uuugaaagcg gcuggacaag gugugacuaa uaaaauuuca 2880
ccauuaucuu auaucgauaa cauguucuuc aauuauuuaa augcagagca ucccuauaggc 2940 uuggcgcuag uaauauuaac aguacuugug auuauuggcu uuguacugaa cauguuuaua 3000
aaacacuuua agaaagagag auuaaucuaa 3030

<210> SEQ ID NO 52
<211> LENGTH: 1191
<212> TYPE: RNA
<213> ORGANISM: Staphylococcus aureus

<400> SEQUENCE: 52
augacgcaac aacaaaauaa uaaaagaaca uuaaaaaaua aacacacuua ucaaaaugaa 60
ccauuaccaa accguaaaga uuuuguuguu aguuuuauaa cuggcgcgcu uguugguuca 120
gcuuuaggcu uauauuuuaa aaauaaaguu uaucaaaaag cagaugauuu aaaagucaaa 180
gaacaagaac ugucgcaaaa guuugaagaa agaaaaacgc aacuugaaga aacgguugcc 240
uuuacaaaag aacguguuga aggauuuuua aacaaaucua aaaaugaaca agcggcauug 300
aaggcacaac aagcagcaau aaaagaagaa gcaagugcaa auaauuuaag cgauacauca 360
caagaggcac aagagauuca agaagcuaaa agagaagcac aaacagaaac ggauaaaagu 420
gcggcuguau caaaugaaga gucaaaggca ucggcauuga aggcacaaca agcagcgaua 480
aaagaagaag caagugcaaa uaauuuaagu gauacaucac aagaagcaca agcgauucaa 540
gaagugaaga aagaagcgca agcagaaaca gauaaaagug cagauguauc aaaugaagaa 600
ucaaaagcau cgacauuaaa cguaucgaaa gaagagucac aagcugaaag auuagcaaac 660
gcugcaaaac agaagcaagc uaaauuaaca ccaggcucaa aagagaguca auuaacugaa 720
gcguuauuug cagaaaaacc aguugcuaaa aaugacuuga aagaaauucc ucuauuaguu 780
acuaaaaaga augauguauc agaaacaguu aauacagaua auaaagacac uguuaaacaa 840
aaagaagcua aauuugaaaa ugguguuauu acacguaaag cugaugaaaa aacaccuaau 900
aauacagcug uugacaagaa aucagguaaa caaucuaaaa aaacaacacc uucaaauaaa 960
cgaaaugcau caaaagcauc gacaaauaaa acuucagguc agaaaaagca acauaauaag 1020
aaagcaucac aaggugcaaa gaaacaaagu aguucaagua acucaacgac aaagacuaau 1080
caaaaaaauu caaaagcaac aaaugcuaaa ucauccaaug caucaaaaaa aucaaaugcu 1140
aaaguugaaa aagcuaaaag uaaaauagag aaacguacau uuaaugacua a 1191

<210> SEQ ID NO 53
<211> LENGTH: 2310
<212> TYPE: RNA
<213> ORGANISM: Staphylococcus aureus

<400> SEQUENCE: 53
guggauauug guaaaaaaca uguaauuccu aaaagucagu accgacguaa gcgucgugaa 60
uucuuccaca acgaagacag agaagaaaau uuaaaucaac aucaagauaa acaaaauaua 120

-continued

```
gauaauacaa caucaaaaaa agcagauaag caaauacaua aagauucaau ugauaagcac    180

gaacguuuua aaaauaguuu aucaucgcau uuagaacaga gaaaccguga ugugaaugag    240

aacaaagcug aagaaaguaa aaguaaucag gguaguaagu cagcauauaa caaagaucau    300

uauuuaacag acgauguauc uaaaaaacaa aauucauuag auucaguaga ccaagauaca    360

gagaaaucaa aauauuauga gcaaaauacu gaagcgacuu uaucaacuaa uucaaccgau    420

aaaguagaau caacugacau gagaaagcua aguucagaua aaaacaaagu uggucaugaa    480

gagcaacaug uacuuucuaa accuucagaa caugauaaag agacuagaau ugauuuugag    540

ucuucaagaa cugauucaga cagcucgaug cagacagaga aaauaaaaaa agacaguuca    600

gauggaaaua aaaguaguaa ucugaaaucu gaaguaauau cagacaaauc aaauucagua    660

ccaauauugu cggaaucuga ugaugaagua aauaaucaga agccauuaac uuugccggaa    720

gaacagaaau ugaaaaggca gcaaagucaa aaugagcaaa caaaaacuua uacauauggu    780

gauagcgaac aaaaugacaa gucuaaucau gaaaaugauu uaagucauca uacaccaucg    840

auaagugaug auaaagauua cguuaugaga gaagaucaua uuguugacga uaauccugau    900

aaugauauca auacaccauc auuaucaaaa auagaugacg aucgaaaacu ugaugaaaaa    960

auucaugucg aagauaaaca uaaacaaaau gcagacucau cugaaacggu gggauaucaa   1020

agucagucaa gugcaucuca ucguagcacu gaaaaaagaa auauggcuau uaaugaccau   1080

gauaaauuaa acggucaaaa accaaauaca aagacaucgg caaauaauaa ucaaaaaaag   1140

gcuacaucaa aauugaacaa agggcgcgcu acaaauaaua auuauagcgc cauuuugaaa   1200

aaguuuugga ugauguauug gccuaaauua guuauucuaa uggguauuau uauucuaauu   1260

guuauuuuga augccauuuu uaauaaugug aacaaaaaug aucgcaugaa ugauaauaau   1320

gaugcagaug cucaaaaaua uacgacaacg augaaaaaug ccaauaacgc aguuaaaucg   1380

gucguuacag uugaaaauga aacaucaaaa gauucaucau uaccuaaaga uaaagcaucu   1440

caagacgaag uaggaucagg uguuguauau aaaaaaucug gagauacguu auauauuguu   1500

acgaaugcac acguugucgg ugauaaagaa aaucaaaaaa uaacuuucuc gaauaauaaa   1560

aguguuguug ggaaagugcu ugguaaagau aaauggucag auuuagcugu uguuaaagca   1620

acuucuucag acaguucagu gaaagagaua gcuauuggag auucaaauaa uuuaguguua   1680

ggagagccaa uauuagucgu agguaaucca cuuggguuag acuuuaaagg cacugugaca   1740

gaagguauua uuucaggucu gaacagaaau guuccaauug auuucgauaa agauaauaaa   1800

uaugauaugu ugaugaaagc uuuccaaauu gaugcaucag uaaauccagg uaacucgggu   1860

ggugcugucg ucaauagaga aggaaaauua auugguguag uugcagcuaa aauuaguaug   1920

ccaaacguug aaaauauguc auuugcaaua ccuguuaaug aaguacaaaa gauuguaaaa   1980

gaauuagaaa caaaagguaa aauugacuau cccgauguag guguuaaaau gaagaauauu   2040

gccagucuaa auaguuuuga aagacaagca guuaaauugc uaggaaaagu uaagaacggu   2100

guuguuguag aucaaguuga caacaauggu uuagcagauc aaucuggucu gaaaaaaggu   2160

gauguaauua cugaauuaga uggcaaacuu uuagaagaug auuuacgcuu uaggcagauu   2220

auauuuaguc auaaagauga cuugaaauca auuacagcga agauuuauag agaugguaaa   2280

gaaaaagaaa uuaauauuaa acuaaaauaa                                    2310
```

<210> SEQ ID NO 54
<211> LENGTH: 627
<212> TYPE: RNA
<213> ORGANISM: Staphylococcus aureus

<400> SEQUENCE: 54
augaaauuca aagcuaucgu ugcaaucaca uuaucauugu cacuauuaac cgccuguggu 60
gcuaaucaac auaaagaaaa uaguaguaaa ucaaaugaca cuaauaaaaa gacgcaacaa 120
acugauaaca cuacacaguc aaauacagaa aagcaaauga cuccacaaga agccgaagau 180
aucguucgaa acgauuacaa agcaagaggu gcuaacgaaa aucaaacauu aaauuauaaa 240
acaaaucuug aacgaaguaa ugaacaugaa uauuauguug aacaucuagu ccgcgaugca 300
guuggcacac cauuaaaacg uugcgcuauu guuaaucgac acaaugguac gauuauuaau 360
auuuuugaug auaugucaga aaaagauaaa gaagaauuug aagcauuuaa aaagagaagc 420
ccuaaauaca acccagguau gaaugaucaa gcugaaaugg auaaugaguc ggaagacauu 480
caacaucaug auauugacaa uaacaaagcc auucaaaaug acuuaccaga ucaaaaaguc 540
gaugauaaaa acgauaaaaa ugcuguuaau aaagaagaaa aacacgauaa ccgugaaaau 600
aauucagcag aaacuaaagu uaaauaa 627

<210> SEQ ID NO 55
<211> LENGTH: 684
<212> TYPE: RNA
<213> ORGANISM: Staphylococcus aureus

<400> SEQUENCE: 55
auggauaaga aaaaagucau caaauuuaug auuaauguau uaccaauugu auugguaccg 60
uuaauuguug aacguaaacg uaucaaacaa cauccggacg uacaaaaagu uacagaugcu 120
acaaguaaag uugcuucaaa aacaucugca gcaaucagua acacagcgag ugauguuaaa 180
gaauaugucg gcgauaaaaa acaagauuuu gaaaauaagc gugaacuuaa aaaguuugcu 240
agagaacaug auccugccua uauugagaaa aaaggcgaaa aauuagcuaa acaaaaucgu 300
aaagacgcug auaaaaugaa uaaaaauacuu caaaaaaaua ucgaaaagcg ucauaaagaa 360
gagcaaaaag cccgcgaaaa gaaugaaaua caacguauua aagauaugaa aaagucacaa 420
aaauacgaag uaaaagcagg cuuaacaccu aauaaauuag augagaaaac ugagaaaaaa 480
ggcgauaaac uagcugaaaa aaaucgcaaa gaaaucgcua aaaugaauaa aaaguuacaa 540
aaaaauauug aaaaacgaca caaagaagaa caaaaacgcc aacaagaagc ugauaaagca 600
cgcaucaagu cauuuaaaaa auauaaagau uauguugcca aaagcgccuc ucaacaaaau 660
aaagaaaaca auacagaggc auaa 684

<210> SEQ ID NO 56
<211> LENGTH: 1215
<212> TYPE: RNA
<213> ORGANISM: Staphylococcus aureus

<400> SEQUENCE: 56
augucauauc auugguuuaa gaaaauguua cuuucaacaa guauguuaau uuuaaguagu 60
aguaguaguu uagggcuugc aacgcacaca guugaagcaa aggauaacuu aaauggagaa 120
aagccaacga cuaauuugaa ucauaaugua acuucaccau caguaaauag ugaaaugaau 180
aauaaugaga cugggacacc ucacgaauca aaucaagcug guaaugaagg aacugguucg 240
aauagucgug augcuaaucc ugauucgaau aaugugaagc cagacucaaa caaccaaaac 300
ccaaguccag auucaaaacc ugacccaaau aacccaaacc cagguccgaa uccgaagcca 360
gacccagaua agccgaaacc aaauccggaa ccaaagccag acccagauaa gccgaaacca 420

```
aauccggauc caaaaccaga uccagacaaa ccgaagccaa auccggaucc aaaaccagau    480

ccaaauccga auccgaaucc aaaaccagac ccuaauaagc caaauccaaa uccgucucca    540

aaucccaauc aaccugggga uuccaaucaa ucugguggcu cgaaaaaugg ggggacaugg    600

aacccaaaug cuucagaugg aucuaaucaa ggucaauggc aaccaaaugg aaaucaagga    660

aacucacaaa auccuacugg uaaugauuuu guaucccaac gauuuuuagc cuuggcgaau    720

ggggcuuaca aguauaaucc guauauuuua aaucaaauua aucaauuggg gaaagaauau    780

ggugagguaa cugaugaaga uaucuacaau aucauccgua aacaaaacuu cagcggaaau    840

gcauauuuaa auggauuaca acagcaaucg aauuacuuua gauuccaaua uuucaaucca    900

uugaaaucag aaagguacua ucguaauuua gaugaacaag uacucgcauu aauuacuggc    960

gaaauuggau caaugccaga uuugaaaaag cccgaagaua agccggauuc aaaacaacgu   1020

ucauuugagc cucaugaaaa agaugauuuu acaguuguaa aaaaacaaga agauaauaag   1080

aaaagugcgu caacugcaua uaguaaaagu uggcuagcaa uuguauguuc uaugauggug   1140

guauuuucaa ucaugcuauu cuuauuugua aagcgaaaua aaaagaaaaa uaaaaacgaa   1200

ucacagcgac gauaa                                                    1215
```

```
<210> SEQ ID NO 57
<211> LENGTH: 696
<212> TYPE: RNA
<213> ORGANISM: Staphylococcus aureus

<400> SEQUENCE: 57

augaagaaaa cauuacucgc aucaucauua gcaguagguu uaggaaucgu agcaggaaau     60

gcaggucacg aagcccaagc aagugaagcg gacuuaaaua aagcaucuuu agcgcaaaug    120

gcgcaaucaa augaucaaac auuaaaucaa aaaccaauug aagcuggcgc uuauaauuau    180

acauuugacu augaagggu uacuuaucac uuugaaucag augguacaca cuuugcuugg    240

aauuaccaug caacaggugc uaauggagca gacaugagug cacaagcacc ugcaacuaau    300

aauguugcac caucagcuga ucaaucuaau caaguacaau cacaagaagu ugaagcacca    360

caaaaugcuc aaacucaaca accacaagca ucaacaucaa acaauucaca aguuacugca    420

acaccaacug aaucaaaagc aucagaaggu ucaucaguaa augugaauga ucaucuaaaa    480

caaauugcuc aacgugaauc agguggcaau auucaugcug uaaauccaac aucaggugca    540

gcugguaagu aucaauucuu acaaucaacu ugggauucag uagcaccugc uaaauauaaa    600

gguguaucac cagcaaaugc uccugaaagu guucaagaug ccgcagcagu aaaacuauau    660

aacacuggug gcgcuggaca uuggguuacu gcauaa                              696
```

```
<210> SEQ ID NO 58
<211> LENGTH: 10
<212> TYPE: DNA
<213> ORGANISM: Artificial sequence
<220> FEATURE:
<223> OTHER INFORMATION: Model sequence

<400> SEQUENCE: 58

atacggaacc                                                            10
```

```
<210> SEQ ID NO 59
<211> LENGTH: 10
<212> TYPE: DNA
<213> ORGANISM: Artificial sequence
<220> FEATURE:
<223> OTHER INFORMATION: Model sequence
```

```
<400> SEQUENCE: 59

atacgggacc                                                          10
```

PROTEINS AND NUCLEIC ACIDS USEFUL IN VACCINES TARGETING *STAPHYLOCOCCUS AUREUS*

CROSS-REFERENCE TO RELATED APPLICATIONS

In accordance with 37 C.F.R. 1.76, a claim of priority is included in an Application Data Sheet filed concurrently herewith. Accordingly, the present invention claims priority as a continuation of U.S. patent application Ser. No. 16/023,741, entitled "PROTEINS AND NUCLEIC ACIDS USEFUL IN VACCINES TARGETING *STAPHYLOCOCCUS AUREUS*", filed Jun. 29, 2018, which claims priority as a divisional of U.S. patent application Ser. No. 15/387,814, entitled "PROTEINS AND NUCLEIC ACIDS USEFUL IN VACCINES TARGETING *STAPHYLOCOCCUS AUREUS*", filed Dec. 22, 2016, now U.S. Pat. No. 10,034,928, issued Jul. 31, 2018, which claims priority as a continuation of U.S. patent application Ser. No. 14/802,602, entitled "PROTEINS AND NUCLEIC ACIDS USEFUL IN VACCINES TARGETING *STAPHYLOCOCCUS AUREUS*", filed Jul. 17, 2015, now U.S. Pat. No. 9,534,022, issued Jan. 3, 2017, which claims priority as a divisional of U.S. patent application Ser. No. 14/110,475, entitled "PROTEINS AND NUCLEIC ACIDS USEFUL IN VACCINES TARGETING *STAPHYLOCOCCUS AUREUS*", filed Nov. 25, 2013, now U.S. Pat. No. 9,085,631, issued Jul. 21, 2015, which is a § 371 national stage entry of International Application No. PCT/EP2012/056069, entitled "PROTEINS AND NUCLEIC ACIDS USEFUL IN VACCINES TARGETING *STAPHYLOCOCCUS AUREUS*", filed Apr. 3, 2012, which claims priority to Danish Patent Application No. PA 2011 70167, entitled "PROTEINS AND NUCLEIC ACIDS USEFUL IN VACCINES TARGETING *STAPHYLOCOCCUS AUREUS*", filed Apr. 8, 2011 and U.S. Provisional Application No. 61/473,376, entitled "PROTEINS AND NUCLEIC ACIDS USEFUL IN VACCINES TARGETING *STAPHYLOCOCCUS AUREUS*", filed Apr. 8, 2011, the entire contents of which are incorporated herein by reference.

FIELD OF THE INVENTION

The present invention relates to the field of antimicrobial prophylaxis and therapy. In particular the present invention relates to novel proteins and polynucleotides derived from *Staphylococcus aureus*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

Bacterial infections are in most instances successfully treated by administration of antibiotics to patients in need thereof. However, due to careless or thoughtless use of powerful antibiotics, many pathological germs become resistant against antibiotics over time. One threatening example is *Staphyloccocus aureus*. In particular in hospitals this bacterium is of relevance. So-called Methicillin Resistant *S. Aureus* (MRSA) strains jeopardize patient's survival in hospitals, in particular after surgery.

Vaccination is considered to be a very effective method of preventing infectious diseases in human and veterinary health care. Vaccination is the administration of immunogenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immuno-protective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

OBJECT OF THE INVENTION

It is an object of embodiments of the invention to provide *S. aureus* derived antigenic polypeptides that may serve as constituents in vaccines against *S. aureus* infections and in diagnosis of *S. aureus* infections. It is also an object to provide nucleic acids, vectors, transformed cells, vaccine compositions, and other useful means for molecular cloning as well as for therapy and diagnosis with relevance for *S. aureus*.

SUMMARY OF THE INVENTION

It has been found by the present inventor(s) that *S. aureus*, in particular drug resistant *S. aureus*, expresses a number of hitherto unknown surface exposed proteins which are candidates as vaccine targets as well as candidates as immunizing agents for preparation of antibodies that target *S. aureus*.

So, in a first aspect the present invention relates to a polypeptide comprising a) an amino acid sequence selected from the group consisting of any one of SEQ ID NOs: 1-19, or b) an amino acid sequence consisting of at least 5 contiguous amino acid residues from any one of SEQ ID NOs: 1-19, or c) an amino acid sequence having a sequence identity of at least 50% with the amino acid sequence of a), d) an amino acid sequence having a sequence identity of at least 60% with the amino acid sequence of b), or e) an assembly of amino acids derived from any one of SEQ ID NOs: 1-19 which has essentially the same 3D conformation as in the protein from which said assembly is derived so as to constitute a B-cell epitope, said polypeptide being antigenic in a mammal.

In another aspect, the invention relates to an isolated nucleic acid fragment, which comprises i) a nucleotide sequence encoding a polypeptide of the invention, or ii) a nucleotide sequence consisting of any one of SEQ ID NOs: 20-57.

iii) a nucleotide sequence consisting of at least 10 consecutive nucleotides in any one of SEQ ID NOs: 20-57, iv) a nucleotide sequence having a sequence identity of at least 60% with the nucleotide sequence in i) or ii), v) a nucleotide sequence having a sequence identity of at least 60% with the nucleotide sequence in iii), vi) a nucleotide sequence complementary to the nucleotide sequence in i)-v), or vii) a nucleotide sequence which hybridizes under stringent conditions with the nucleotide sequence in i)-vi).

In a third aspect, the invention relates to a vector comprising the nucleic acid of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immunogenically effective amount of a polypeptide of the invention, a nucleic acid fragment of the invention, a vector of the invention, a transformed cell of the invention, or a pharmaceutical composition of the fifth aspect of the invention so as to induce adaptive immunity against *S. aureus* in the animal.

In a seventh and eighth aspect, the invention relates to 1) a polyclonal antibody in which the antibodies specifically bind to at least one polypeptide of the invention, and which is essentially free from antibodies binding specifically to other *S. aureus* polypeptides, and to 2) an isolated monoclonal antibody or antibody analogue which binds specifically to a polypeptide of the invention. In a related ninth aspect, the invention relates to a pharmaceutical composition comprising such a polyclonal or monoclonal antibody and a pharmaceutically acceptable carrier, vehicle or diluent.

In a $10^{th}$ aspect, the invention relates to a method for prophylaxis, treatment or amelioration of infection with *S. aureus*, in particular infection with multi-resistant *S. aureus*, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of *S. aureus*, in particular the presence of multi-resistant *S. aureus*, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for *S. aureus*, in particular the presence of antibodies specific for multi-resistant *S. aureus*, in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of *S. aureus*, in particular the presence of a nucleic acid characteristic of multi-resistant *S. aureus*, in a sample, the method comprising contacting the sample with a nucleic acid fragment of the invention and detecting the presence of nucleic acid in the sample that hybridizes to said nucleic acid fragment.

In a $14^{th}$ aspect, the invention relates to a method for the preparation of the polypeptide of the invention, comprising culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or preparing said polypeptide by means of solid or liquid phase peptide synthesis.

In a $15^{th}$ aspect, the invention relates to a method for determining whether a substance, such as an antibody, is potentially useful for treating infection with *S. aureus*, the method comprising contacting the polypeptide of the invention with the substance and subsequently establishing whether the substance has at least one of the following characteristics:

1) the ability to bind specifically to said polypeptide, 2) the ability to compete with said polypeptide for specific binding to a ligand/receptor, and 3) the ability to specifically inactivate said polypeptide.

Finally, in a $16^{th}$ aspect, the invention relates to a method for determining whether a substance, such as a nucleic acid, is potentially useful for treating infection with *S. aureus*, the method comprising contacting the substance with the nucleic acid fragment of claim of the invention and subsequently establishing whether the substance has either the ability to 1) bind specifically to the nucleic acid fragment, or 2) bind specifically to a nucleic acid that hybridizes specifically with the nucleic acid fragment.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Further-more, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively The term “amino acid sequence” is the order in which amino acid residues, connected by peptide bonds, lie in the chain in peptides and proteins.

The term “adjuvant” has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

“Sequence identity” is in the context of the present invention determined by comparing 2 optimally aligned sequences of equal length (e.g. DNA, RNA or amino acid) according to the following formula: $(N_{ref}-N_{df})\cdot 100/N_{ref}$, wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAACC-3' (SEQ ID NO: 58) and 5'-ATACGGGACC-3' (SEQ ID NO: 58) will provide the sequence identity 80% ($N_{ref}$=10 and $N_{dif}$=2).

An “assembly of amino acids” means two or more amino acids bound together by physical or chemical means.

The “3D conformation” is the 3 dimensional structure of a biomolecule such as a protein. In monomeric polypeptides/proteins, the 3D conformation is also termed “the tertiary structure” and denotes the relative locations in 3 dimensional space of the amino acid residues forming the polypeptide.

“An immunogenic carrier” is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immunogen by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A “T-helper lymphocyte response” is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule present.

An “immunogen” is a substance of matter which is capable of inducing an adaptive immune response in a host, whose immune system is confronted with the immunogen. As such, immunogens are a subset of the larger genus “antigens”, which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A “hapten” is a small molecule, which can neither induce nor elicit an immune response, but if conjugated to an immunogenic carrier, antibodies or TCRs that recognize the hapten can be induced upon confrontation of the immune system with the hapten carrier conjugate.

An “adaptive immune response” is an immune response in response to confrontation with an antigen or immunogen, where the immune response is specific for antigenic determinants of the antigen/immunogen—examples of adaptive immune responses are induction of antigen specific antibody production or antigen specific induction/activation of T helper lymphocytes or cytotoxic lymphocytes.

A “protective, adaptive immune response” is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

“Stimulation of the immune system” means that a substance or composition of matter exhibits a general, non-specific immunostimulatory effect. A number of adjuvants and putative adjuvants (such as certain cytokines) share the ability to stimulate the immune system. The result of using an immunostimulating agent is an increased “alertness” of the immune system meaning that simultaneous or subsequent immunization with an immunogen induces a significantly more effective immune response compared to isolated use of the immunogen.

Hybridization under “stringent conditions” is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term “animal” is in the present context in general intended to denote an animal species (preferably mammalian), such as *Homo sapiens*, *Canis domesticus*, etc. and not just one single animal. However, the term also denotes a population of such an animal species, since it is important that the individuals immunized according to the method of the invention substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterologous nucleic acid sequence The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

SPECIFIC EMBODIMENTS OF THE INVENTION

The Polypeptides of the Invention

In some embodiments the at least 5 contiguous amino acids referred to in option b) in the definition of the first aspect of the invention constitute at least 6, such as at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27 at least 28, at least 29, at least 30, at least 31, at least 32, at least 33, at least 34, and at least 35 contiguous amino acid residues. The number can be higher, for all of SEQ ID NOs, 1-19 at least 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 65, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, and at least 124 contiguous amino acid residues. Another way to phrase this is that for each of SEQ ID NOs: 1-19, the number of the contiguous amino acid residues is at least N-n, where N is the length of the sequence ID in question and n is any integer between 6 and N-1; that is, the at least 5 contiguous amino acids can be at least any number between 5 and the length of the reference sequence minus one, in increments of one.

In some embodiments, the polypeptide of the invention also has a sequence identity with the amino acid sequence of a) defined above of at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98%, and at least 99%.

In the embodiments defined by option b) above, the polypeptide of the invention is also one that has at least 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 125, 127, and 128 in any one of SEQ ID NOs: 1-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 126, 127, 128, 129, 130, 131, 132, 133, 134, 135, 136, 137, 138, 139, and 140 in any one of SEQ ID NOs: 1, 2, and 4-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 141, 142, 143, 144, 145, 146, 147, 148, 149, and 150 in any one of SEQ ID NOs: 1, 2, and 4-6, and 8-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 151, 152, 153, 154, 155, 156, 157, 158, 159, 160, 161, 162, 163, 164, 165, 166, 167, 168, 169, 170, 171, 172, 173, 174, 175, 176, 177, 178, 179, and 180 in any one of SEQ ID NOs: 2, 4-6, and 8-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 181, 182, 183, 184, 185, and 186 in any one of SEQ ID NOs: 4-6, and 8-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 187, 188, 189, 190, 191, 192, 193, 194, 195, 196, 197, 198, 199, 200, 201, 202, 203, and 204 in any one of SEQ ID NOs: 4-6, 8-11, 13-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to amino acid residue 205 in any one of SEQ ID NOs: 4-6, 8-11, 13-15, and 17-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 206, 207, 208, 209, 210, 211, 212, 213, 214, 215, 216, 217, 218, 219, 220, 221, 222, and 223 in any one of SEQ ID NOs: 4-6, 8-10, 13-15, and 17-19, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 224, 225, 226, and 227 in any one of SEQ ID NOs: 4-6, 8-10, 13-15, 18, and 19, if the length of the at least 5 amino acid residues so permit if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 252, 263, 264, 265, 266, 267, 258, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 350, 361, 362, 363, 364, 355, 366, 367, 368, 369, 370, 371, 372, 373, 374, 375, 376, 377, 378, 379, 380, 381, 382, 383, 384, 385, 386, 387, 388, 389, 390, 391, and 392 in any one of SEQ ID NOs: 4-6, 8-10, 13-15, and 18, if the length of the at least 5 amino acid residues so permit if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 393, 394, 395, 396, 397, 398, 399, and 400 in any one of SEQ ID NOs: 4-6, 8-10, 13, 15, and 18, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 445, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, and 482 in any one of SEQ ID NOs: SEQ ID NOs: 4-6, 8-10, 13, and 15, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 554, 565, 566, 567, 568, 559, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, and 605 in any one of SEQ ID NOs: 4-6, 8, 10, 13, and 15, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 553, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 735, 737, 738, 739, 740, 741, 742, 743, 744, 745, 745, 747, 748, 749, 750, 751, 752, 753, 754, 755, 756, 757, 758, 759, 760, 751, 752, 763, 764, and 755 in any one of SEQ ID NOs: 4, 5, 8, 10, 13, and 15, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 850, 861, 862, 863, 864, 855, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, and 989 in any one of SEQ ID NOs: 4, 5, 8, 10, and 13, if the length of the at least 5 amino acid residues so permit if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 990, 991, 992, 993, 994, 995, 996, 997, 998, 999, 1000, 1001, 1002, 1003, 1004, and 1005, in any one of SEQ ID NOs: 5, 8, 10, and 13, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, 1106, 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1205, 1207, 1208, 1209, 1210, 1211, 1212, 1213, 1214, 1215, 1216, 1217, 1218, 1219, 1220, 1221, 1222, 1223, 1224, 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, and 1253 in any one of SEQ ID NOs: 5, 8, and 10, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1254, 1255, 1256, 1257, 1258, 1259, 1260, 1261, 1262, 1263, 1264, 1265, 1266, 1267, 1268, 1269, and 1270 in SEQ ID NO: 5 or 10, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1271, 1272, 1273, 1274, 1275, 1276, 1277, 1278, 1279, 1280, 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1525, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1550, 1551, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1505, 1605, 1607, 1608, 1609, 1510, 1611, 1612, 1613, 1614, 1615, 1515, 1617, 1618, 1619, 1620, 1621, 1622, 1623, 1624, 1625, 1626, 1527, 1628, 1629, 1630, 1631, 1632, 1533, 1634, 1635, 1636, 1637, 1638, 1639, 1640, 1641, 1642, 1643, 1644, 1645, 1646, 1647, 1648, 1649, 1650, 1651, 1652, 1653, 1654, 1555, 1655, 1657, 1658, 1659, 1660, 1551, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1795, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1885, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1935, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, and 2062 in SEQ ID NO: 5, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NOs. 1-19. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, diphtheria toxoid or a fragment thereof. Other suitable carrier molecules are discussed infra.

In preferred embodiments, the polypeptide of the invention detailed above is capable of inducing an adaptive immune response against the polypeptide in a mammal, in particular in a human being. Preferably, the adaptive immune response is a protective adaptive immune response against infection with *S. aureus*, in particular multi-resistant *S. aureus*. The polypeptide may in these cases induce a humeral and/or a cellular immune response.

Epitopes

SEQ ID NOs: 1-19 include antigenic determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised against *S. aureus* or *S. aureus* derived proteins disclosed herein are tested for binding to overlapping oligomeric peptides derived from any one of SEQ ID NO: 1-19. Thereby, the regions of the *S. aureus* polypeptide which are responsible for or contribute to binding to the antibodies can be identified.

Alternatively, or additionally, one can produce mutated versions of the polypeptides of the invention, e.g. version where each single non-alanine residue in SEQ ID NOs.: 1-19 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), Plos One 5(11): e15079; prediction of linear B-cell epitopes, cf: Larsen J E P et al. (April 2006), Immunome Research, 2:2; prediction of solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (such as SEQ ID NOs: 20-38) or an RNA fragment (such as SEQ ID NOs 29-58).

The nucleic acid fragment of the invention typically consists of at least 11, such as at least 12, at least 13, at least 14, at least 15, at least 16, at least 17 at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 58, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100, at least 101, at least 102, at least 103, at least 104, at least 105, at least 106, at least 107, at least 108, at least 109, at least 110, at least 111, at least 112, at least 113, at least 114, at least 115, at least 116, at least 117, at least 118, at least 119, at least 120, at least 121, at least 122, at least 123, at least 124, at least 125, at least 126, at least 127, at least 128, at least 129, at least 130, at least 131, at least 132, at least 133, at least 134, at least 135, at least 136, at least 137, at least 138, at least 139, at least 140, at least 141, at least 142, at least 143, at least 144, at least 145, at least 146, at least 147, at least 148, at least 149, at least 150, at least 151, at least 152, at least 153, at least 154, at least 155, at least 155, at least 157, at least 158, at least 159, at least 160, at least 161, at least 162, at least 163, at least 164, at least 165, at least 166, at least 167, at least 168, at least 169, at least 170, at least 171, at least 172, at least 173, at least 174, at least 175, at least 176, at least 177, at least 178, at least 179, at least 180, at least 181, at least 182, at least 183, at least 184, at least 185, at least 186, at least 187, at least 188, at least 189, at least 190, at least 191, at least 192, at least 193, at least 194, at least 195, at least 196, at least 197, at least 198, at least 199, at least 200, at least 201, at least 202, at least 203, at least 204, at least 205, at least 206, at least 207, at least 208, at least 209, at least 210, at least 211, at least 212, at least 213, at least 214, at least 215, at least 216, at least 217, at least 218, at least 219, at least 220, at least 221, at least 222, at least 223, at least 224, at least 225, at least 226, at least 227, at least 228, at least 229, at least 230, at least 231, at least 232, at least 233, at least 234, at least 235, at least 236, at least 237, at least 238, at least 239, at least 240, at least 241, at least 242, at least 243, at least 244, at least 245, at least 246, at least 247, at least 248, at least 249, at least 250, at least 251, at least 252, at least 253, at least 254, at least 255, at least 256, at least 257, at least 258, at least 259, at least 260, at least 261, at least 262, at least 263, at least 264, at least 265, at least 266, at least 267, at least 268, at least 269, at least 270, at least 271, at least 272, at least 273, at least 274, at least 275, at least 276, at least 277, at least 278, at least 279, at least 280, at least 281, at least 282, at least 283, at least 284, at least 285, at least 286, at least 287, at least 288, at least 289, at least 290, at least 291, at least 292, at least 293, at least 294, at least 295, at least 296, at least 297, at least 298, at least 299, at least 300, at least 301, at least 302, at least 303, at least 304, at least 305, at least 306, at least 307, at least 308, at least 309, at least 310, at least 311, at least 312, at least 313, at least 314, at least 315, at least 316, at least 317, at least 318, at least 319, at least 320, at least 321, at least 322, at least 323, at least 324, at least 325, at least 326, at least 327, at least 328, at least 329, at least 330, at least 331, at least 332, at least 333, at least 334, at least 335, at least 336, at least 337, at least 338, at least 339, at least 340, at least 341, at least 342, at least 343, at least 344, at least 345, at least 346, at least 347, at least 348, at least 349, at least 350, at least 351, at least 352, at least 353, at least 354, at least 355, at least 356, at least 357, at least 358, at least 359, at least 360, at least 361, at least 362, at least 363, at least 354, at least 365, at least 366, at least 367, at least 368, at least 369, at least 370, at least 371, at least 372, at least 373, at least 374, at least 375, at least 376, at least 377, at least 378, at least 379, at least 380, at least 381, at least 382, at least 383, at least 384, at least 385, at least 386, at least 387 consecutive nucleotides in any one of SEQ ID NOs: 20-57. Longer fragments are contemplated, i.e. fragments having at least 400, at least 500, at least 600, at least 700, at least 800, at least 900, at least 1000, at least 1500, at least 2000, and at least 2500 nucleotides from those of SEQ ID NOs: 20-57 that encompass fragments of such lengths.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98% and at least 99%.

The Vectors of the Invention

Vectors of the invention fall into several categories discussed infra. One preferred vector of the invention comprises in operable linkage and in the 5'-3' direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention, Since the polypeptides of the invention are bacterial of origin, recombinant production is conveniently effected in bacterial host cells, so here it is preferred that the expression control region drives expression in prokaryotic cell such as a bacterium, e.g. in *E coli*.

However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination.

Typically, the vector of the invention is selected from the group consisting of a virus, such as an attenuated virus (which may in itself be useful as a vaccine agent), a bacteriophage, a plasmid, a minichromosome, and a cosmid.

A more detailed discussion of vectors of the invention is provided in the following:

Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR (™), in connection with the compositions disclosed herein (see U.S. Pat. Nos. 4,683,202, 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference), The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain (Banerji et al, 1983; Gilles et al, 1983; Grosschedl et al, 1985; Atchinson et al, 1986, 1987; toiler et al, 1987; Weinberger et al, 1984; Kiledjian et al, 1988; Porton et al; 1990), Immunoglobulin Light Chain (Queen et al, 1983; Picard et al, 1984), T Cell Receptor (Luria et al, 1987; Winoto et al, 1989; Redondo et al; 1990), HLA DQα and/or DQβ (Sullivan et al, 1987), β-Interferon (Goodbourn et al, 1986; Fujita et al, 1987; Goodbourn et al, 1988), Interleukin-2 (Greene et al, 1989), Interleukin-2 Receptor (Greene et al, 1989; Lin et al, 1990), MHC Class II 5 (Koch et al, 1989), MHC Class II HLA-DRo (Sherman et al, 1989), β-Actin (Kawamoto et al, 1988; Ng et al; 1989), Muscle Creatine Kinase (MCK) (Jaynes et al, 1988; Horlick et al, 1989; Johnson et al, 1989), Prealbumin (Transthyretin) (Costa et al, 1988), Elastase I (Omitz et al, 1987), Metallothionein (MTII) (Karin et al, 1987; Culotta et al, 1989), Collagenase (Pinkert et al, 1987; Angel et al, 1987), Albumin (Pinkert et al, 1987; Tranche et al, 1989, 1990),α-Fetoprotein (Godbout et al, 1988; Campere et al, 1989), γ-Globin (Bodine et al, 1987; Perez-Stable et al, 1990), β-Globin (Trudel et al, 1987), c-fos (Cohen et al, 1987), c-HA-ras (Triesman, 1986; Deschamps et al, 1985), Insulin (Edlund et al, 1985), Neural Cell Adhesion Molecule (NCAM) (Hirsh et al, 1990), αl-Antitrypain (Larimer et al, 1990), H2B (TH2B) Histone (Hwang et al, 1990), Mouse and/or Type I Collagen (Ripe et al, 1989), Glucose-Regulated Proteins (GRP94 and GRP78) (Chang et al, 1989), Rat Growth Hormone (Larsen et al, 1986), Human Serum Amyloid A (SAA) (Edbrooke et al, 1989), Troponin I (TN I) (Yutzey et al, 1989), Platelet-Derived Growth Factor (PDGF) (Poch et al, 1989), Duchenne Muscular Dystrophy (Klamut et al, 1990), SV40 (Banerji et al, 1981; Moreau et al, 1981; Sleigh et al, 1985; Firak et al, 1986; Herr et al, 1986; Imbra et al, 1986; Kadesch et al, 1986; Wang et al, 1986; Ondek et al, 1987; Kuhl et al, 1987; Schaffner et al, 1988), Polyoma (Swartzendruber et al, 1975; Vasseur et al, 1980; Katinka et al, 1980, 1981; Tyndell et al, 1981; Dandolo et al, 1983; de Villiers et al, 1984; Hen et al, 1986; Satake et al, 1988; Campbell et al, 1988), Retroviruses (Kriegler et al, 1982, 1983; Levinson et al, 1982; Kriegler et al, 1983, 1984a, b, 1988; Bosze et al, 1986; Miksicek et al, 1986; Celander et al, 1987; Thiesen et al, 1988; Celander et al, 1988; Choi et al, 1988; Reisman et al, 1989), Papilloma Virus (Campo et al, 1983; Lusky et al, 1983; Spandidos and Wilkie, 1983; Spalholz et al, 1985; Lusky et al, 1986; Cripe et al, 1987; Gloss et al, 1987; Hirochika et al, 1987; Stephens et al, 1987), Hepatitis B Virus (Bulla et al, 1986; Jameel et al, 1986; Shaul et al, 1987; Spandau et al, 1988; Vannice et al, 1988), Human Immunodeficiency Virus (Muesing et al, 1987; Hauber et al, 1988; Jakobovits et al, 1988; Feng et al, 1988; Takebe et al, 1988; Rosen et al, 1988; Berkhout et al, 1989; Laspia et al, 1989; Sharp et al, 1989; Braddock et al, 1989), Cytomegalovirus (CMV) IE (Weber et al, 1984; Boshart et al, 1985; Foecking et al, 1986), Gibbon Ape Leukemia Virus (Holbrook et al, 1987; Quinn et al, 1989).

Inducible Elements include, but are not limited to MT II—Phorbol Ester (TFA)/Heavy metals (Palmiter et al, 1982; Haslinger et al, 1985; Searle et al, 1985; Stuart et al, 1985; Imagawa et al, 1987, Karin et al, 1987; Angel et al, 1987b; McNeall et al, 1989); MMTV (mouse mammary tumor virus)—Glucocorticoids (Huang et al, 1981; Lee et al, 1981; Majors et al, 198:3; Chandler et al, 1983; Lee et al, 1984; Ponta et al, 1985; Sakai et al, 1988); β-Interferon—poly(rl) x/poly(rc) (Tavernier et al, 1983); Adenovirus 5 E2—EIA (Imperiale et al, 1984); Collagenase—Phorbol Ester (TPA) (Angel et al, 1987a); Stromelysin—Phorbol Ester (TPA) (Angel et al, 1987b); SV40 Phorbol Ester (TPA) (Angel et al, 1987b); Murine MX Gene—Interferon, Newcastle Disease Virus (Hug et al, 1988); GRP78 Gene—A23187 (Resendez et al, 1988); α-2-Macroglobulin—IL-6 (Kunz et al, 1989); Vimentin—Serum (Rittling et al, 1989); MHC Class I Gene H-2κb—Interferon (Blanar et al, 1989); HSP70 E1A/SV40 Large T Antigen (Taylor et al, 1989, 1990a, 1990b); Proliferin—Phorbol Ester/TPA (Mordacq et al, 1989); Tumor Necrosis Factor—PMA (Hensel et al, 1989); and Thyroid Stimulating Hormonea Gene—Thyroid Hormone (Chatterjee et al, 1989).

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down-regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well as an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,555 and 5,935,819, herein incorporated by reference)

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression. (See Chandler et al, 1997, incorporated herein by reference.)

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells. Polyadenylation may increase the stability of the transcript or may facilitate cytoplasmic transport.

6. Origins of Replication

In order to propagate a vector in a host cell, it may contain one or more origins of replication sites (often termed "on"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection, A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the second aspect of the invention, Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of Escherichia (such as *E. coli.*), *Bacillus* [e.g. *Bacillus subtilis*], *Salmonella*, and *Mycobacterium* [preferably non-pathogenic, e.g. *M. bovis* BCG].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

As noted above, stably transformed cells are preferred—these inter alia (i.a.) allows that cell lines comprised of transformed cells as defined herein may be established—such cell lines are particularly preferred aspects of the invention.

Further details on cells and cell lines are presented in the following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudornonas* genus such as *Ps. fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactic* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms “cell,” “cell line,” and “cell culture” may be used interchangeably. All of these terms also include their progeny, which is any and all subsequent generations. It is understood that all progeny may not be identical due to deliberate or inadvertent mutations. In the context of expressing a heterologous nucleic acid sequence, “host cell” refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be “transfected” or “transformed,” which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5α, JMI 09, and KC8, as well as a number of commercially available bacterial hosts such as SURE(R) Competent Cells and SOLOP ACK(™) Gold Cells (STRATAGENE(®), La Jolla, Calif.). Alternatively, bacterial cells such as *E. coli* LE392 could be used as host cells for phage viruses. Appropriate yeast cells include *Saccharomyces cerevisiae, Saccharomyces pompe*, and *Pichia pastoris.*

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®.

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR(™)) which is described in detail in U.S. Pat. Nos. 4,683,495, 4,683,202 and 4,800,159; and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al, 1987); by liposome mediated transfection (Nicolau and Sene, 1982; Fraley et al, 1979; Nicolau et al, 1987; Wong et al, 1980; Kaneda et al, 1989; Kato et al, 1991); by rnicroprojectile bombardment (PCT Application Nos. WO 94/09699 and 95/06128; U.S. Pat. Nos. 5,610,042; 5,322,783 5,553,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al, 1993; U.S. Pat. Nos. 4,684,611 and 4,952,500, each incorporated herein by reference); by desiccation/inhibition mediated DNA uptake (Potrykus et al, 1985). Through the application of techniques such as these, organelle(s), cell(s), tissue(s) or organism(s) may be stably or transiently transformed.

The Antibodies of the Invention—and Their Production/Isolation

Antibodies directed against the proteins of the invention are useful for affinity chromatography, immunoassays, and for distinguishing/identifying *staphylococcus* proteins as well as for passive immunisation and therapy.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-5 weeks later with one or more injections of the protein in saline, preferably using Freund's incomplete adjuvant. One may alternatively generate antibodies by in vitro immunization using methods known in the art, which for the purposes of this invention is considered equivalent to in viva immunization. Polyclonal antiserum is obtained by bleeding the immunized animal into a glass or plastic container, incubating the blood at 25 C for one hour, followed by incubating at 4 C for 2-18 hours. The serum is recovered by centrifugation (e.g. 1,000 g for 10 minutes), About 20-50 ml per bleed may be obtained from rabbits.

Monoclonal antibodies are prepared using the standard method of Kohler & Milstein [Nature (1975) 256: 495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen, B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective medium (e.g. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (e.g. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly 32p and 125I), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor, Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, 1151 may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with, 125I, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an $F(ab')_2$, an scFV; cf. also the definition of the term "antibody" presented above.

Compositions of the Invention; Vaccines

Pharmaceutical compositions, in particular vaccines, according to the invention may either be prophylactic (i.e. to prevent infection) or therapeutic (i.e. to treat disease after infection).

Such vaccines comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, *H. pylori*, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tvveen 80, and 0.5% Span 85 (optionally containing various amounts of MTP-PE (see below), although not required) formulated into submicron particles using a microfluidizer such as Model 110Y microfluidizer (Microfluidics, Newton, Mass.), (b) SAF, containing 10% Squalane, 0.4% Tween 80, 5% pluronic-blocked polymer L121, and thr-MDP (see below) either microfluidized into a submicron emulsion or vertexed to generate a larger particle size emulsion, and (c) Ribi adjuvant system (RAS), (Ribi Immunochem, Hamilton, Mont.) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™) ; (3) saponin adjuvants such as Stimulon™ (Cambridge Bioscience, Worcester, Mass.) may be used or particles generated therefrom such as ISCOMs (immunostimulating complexes); (4) Complete Freund's Adjuvant (CFA) and Incomplete Freund's Adjuvant (IFA); (5) cytokines, such as interleukins (e.g. IL-1, IL-2, IL-4, IL-5, IL-5, IL-7, IL-12, etc.), interferons (e.g. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred.

As mentioned above, muramyl peptides include, but are not limited to, N-acetyl-muramyl-L-threonyl-D-isoglutarnine (thr-MDP), N-acetyl-normuramyl-L-alanyl-D-isoglutamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (e.g. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunollogically effective amount", it is meant that the administration of that amount to an individual, either in a single dose or as part of a series, is effective for treatment or prevention. This amount varies depending upon the health and physical condition of the individual to be treated, the taxonomic group of individual to be treated (e.g. nonhuman primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 μg and 500 mg (however, often not higher than 5,000 μg), and very often in the range between 10 and 200 μg.

The immunogenic compositions are conventionally administered parenterally, e.g. by injection, either subcutaneously, intramuscularly, or transdermally/transcutaneously (e.g. W098/20734). Additional formulations suitable for other modes of administration include oral and pulmonary formulations, suppositories, and transdermal applications. In the case of nucleic acid vaccination, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [e.g. Robinson & Torres (1997) Seminars in Immunol 9: 271-283; Donnelly et al. (1997) Avnu Rev Immunol 15: 617-648; later herein].

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 μg of the polypeptide of the invention per administration.

In preferred embodiments of the sixth aspect, the immunization scheme includes that the animal (e.g. the human) receives a priming administration and one or more booster administrations.

Preferred embodiments of the $6^{th}$ aspect of the invention comprise that the administration is for the purpose of inducing protective immunity against *S. aureus*. In this embodiment it is particularly preferred that the protective immunity is effective in reducing the risk of attracting infection with *S. aureus* or is effective in treating or ameliorating infection with *S. aureus*.

As mention herein, the preferred vaccines of the invention induce humoral immunity, so it is preferred that the administration is for the purpose of inducing antibodies specific for *S. aureus* and wherein said antibodies or B-lymphocytes producing said antibodies are subsequently recovered from the animal.

But, as also mentioned the method of the $6^{th}$ aspect may also be useful in antibody production, so in other embodiments the administration is for the purpose of inducing antibodies specific for *S. aureus* and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N.J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claim, the invention also relates to related embodiments to the treatment and prophylaxis disclosed herein: the invention also includes embodiments where the polypeptide of the invention is for use as a pharmaceutical, in particular for use as a pharmaceutical in the treatment, prophylaxis or amelioration of infection with *S. aureus;* the nucleic acid fragment of the invention or the vector of the invention is for use as a pharmaceutical, in particular for use as a pharmaceutical in the treatment, prophylaxis or amelioration of infection with *S. aureus;* the transformed cell of the invention is for use as a pharmaceutical, in particular for use as a pharmaceutical in the treatment, prophylaxis or amelioration of infection with *S. aureus.* the antibody, antibody fragment or antibody analogue of the invention is for use as a pharmaceutical, in particular for use as a pharmaceutical in the treatment, prophylaxis or amelioration of infection with *S. aureus.*

EXAMPLE

Protocol for Testing *S. Aureus* Derived Vaccines in Mice

Expression and Purification of *S. Aureus* Genes

1. Gene fragments that encode the selected *S. aureus* polypeptides of the invention are prepared synthetically and are introduced into the pQE-1 vector (Qiagen) from Genscript. The fragments are inserted by blunt ended ligation into the PVU II site in the 5'-end, immediately following the vector's coding region for the 6 histidinyl residues. In the 3'-end, all inserted gene fragments include a stop codon.

2. The vectors from 1 are transfected into the *E. Coli* M15[pREP4] strain, which contains an expression as well as a repressor plasmid facilitating proper expression.

3. The vectors from 1 are further inserted into the *E. coli* XL1 Blue for long-time storage.

4. The transfected and selected clones are tested for expression in small scale whereby optimum conditions for expression in terms of the amount of IPTG, the density of cells and the time of expression induction are determined.

5. From the information obtained in 4, large scale cultures are established; subsequently the expression products are harvested and purified on a Ni-NTA column.

6. Purity and yield of the large-scale expression is investigated by means of SDS-PAGE and spectrophotometry, whereafter the proteins are aliquoted for use in immunization experiments and other experiments.

Immunization and *S. Aureus* Challenge Infection in Mice (Zhou et al. 2006 Vaccine 24. 4830-4837)

1. 2. months old NMKI mice were used.

2. Groups of 8 mice (unless other numbers are indicated) were used for immunization. The mice were immunized 3 times (at day 0, 14, and 28) prior to challenge infection. A control group of 8 mice was treated according to an identical protocol with the exception that an irrelevant protein antigen was used for immunization.

1st Immunization:

50 μg protein (per mice) was mixed with 100 μl aluminum hydroxide (Alhydrogel 2.0%, Brenntag) per 125 μg protein and incubated with end-over-end rotation for 15 min. Freund's incomplete adjuvant (sigma) was added in the volume 1:1 and the mixture was vortexed thoroughly for 1 hour. This mixture was injected subcutaneously 2nd and 3rd Immunization The mice were booster injected intraperitoneally with 2 weeks interval, using the same amount of protein mixed with aluminum hydroxide and physiological saline solution.

3. One week after the last immunization 250 μl blood is drawn from the mice in order to determine the antibody titer.

4. 14 days after the last immunization, a number of bacteria ($2\times10^9$ cells) corresponding to a predetermined $LD_{90}$ in the control group of mice was administered intraperitoneally to all mice.

The cells were handled cold and kept on ice until use. The stock solution of MRSA cells were thawed on ice and then the appropriate amount of cells in sterile physiological saline (total volume per mouse 500 μl).

The survival was surveilled twice daily in the first 48 hours after challenge and once daily in the subsequent 7 days. The mice were sacrificed if they showed signs of suffering. The mice were monitored with respect to loss of weight and body temperature using an implanted chip. The organs of the mice were used for determination of CFU counts.

Test of Antibody Titer

Maxisorp microtiter plates (Nunc, Roskilde, Denmark) were coated overnight with 1 μg/ml recombinant peptide (His-tagged SAR-protein), 100 μl/well.

The next day the plates were emptied and washed 3 times in PBS-Tw. After the last wash the plates were allowed to stand in PBS-Tw for a minimum of 15 minutes (blocking step).

EDTA plasma was diluted 1:100 in PBS-Tw and 200 μl was added to the first well. 100 μl of washing buffer was added to all of the other wells.

A 2-fold dilution was made by transferring 100 ml from the first well to the next, and so on. The plates were incubated at room temperature for 2 hours with shaking.

The plates were washed and 100 μl of secondary antibody was added per well (e.g. HRP conjugated polyclonal rabbit anti-mouse immunoglobulin) and then incubated for 1 hour at room temperature with shaking.

The plates were washed and the ELISA developed. The optical density value was used to calculate the antibody titer: [1/Dilution at ½ max absorbance].

Buffers used were:

Coating buffer: 15 mM $Na_2CO_3$, 35 mM $NaHCO_3$

PBS-Tw: PBS, 0.05% Tween-20 pH 7.4

Coloring buffer for developing the ELISA: 7.3 g citric acid, 11.86 g $NaHPO_4$ pH 5.0 at 1 L. OPD tablets (KemEn-Tec, Diagnostic; were added, 2 mg per 5 ml coloring buffer, Immediately before use, 2 ml of 35% $H_2O_2$ was added per tablet. 100 ml of the mixed coloring substrate was added to each well. The reaction was stopped with 100 ml 1M $H_2SO_4$.

Result of Challenge Studies

The polypeptides used in the challenge studies described are in the following section setting forth the results provided with identification numbers in the format "SARXXXX". For easy reference, these polypeptides relate to the SEQ ID NOs used herein according to the following table:

| | | | |
|---|---|---|---|
| SEQ ID 1: | SAR2104 | SEQ ID 2: | SAR1879 |
| SEQ ID 3: | SAR0730 | SEQ ID 4: | SAR2722 |
| SEQ ID 5: | SAR1507 | SEQ ID 6: | SAR0222 |
| SEQ ID 7: | SAR1558 | SEQ ID 8: | SAR1026 |
| SEQ ID 9: | SAR1489 | SEQ ID 10: | SAR1819 |
| SEQ ID 11: | SAR0826 | SEQ ID 12: | SAR0390 |
| SEQ ID 13: | SAR0280 | SEQ ID 14: | SAR1816 |
| SEQ ID 15: | SAR0992 | SEQ ID 16: | SAR1881 |
| SEQ ID 17: | SAR0735 | SEQ ID 18: | SAR2119 |
| SEQ ID 19: | SAR2184 | | |

The challenge study gave the following results in term of overall survival in the vaccinated groups vs. the control groups:

| | Percentage of mice surviving at end of experiment | |
|---|---|---|
| Vaccine protein | Vaccinated mice | Control control group |
| SAR2104-20-154 | 50% | 0% |
| SAR0280-28-820 | 75% | 0% |
| SAR0390-21-190 | 0% | 0% |
| SAR2104-20-154 | 25% | 0%* |
| SAR1879-24-184 | 14%* | 0%* |
| SAR0222-27-609 | 13% | 0%* |
| SAR1881-25-208 | 13% | 0%* |
| SAR2119-34-370 | 25% | 0%* |
| SAR0872-27-273 | 29%* | 0%* |
| SAR2718-24-157 | 17%** | 0%* |
| SAR1816-1-27 | 67%** | 0% (50%) |
| SAR0735-26-227 | 88% | 0% (50%) |
| SAR0992-428-769 | 29%* | 0% (50%) |
| SAR1816-46-396 | 63% | 0% (50%) |
| 1:1:1 Mixture of SAR2104-20-154 SAR0280-28-820 SAR0872-27-273 | 88%# | 0%# |
| SAR0826-42-209 | 0% | (13%) |

-continued

| | Percentage of mice surviving at end of experiment | |
|---|---|---|
| Vaccine protein | Vaccinated mice | Control control group |
| SAR0992-1-409 | 100% | (13%) |
| SAR1489-343-486 | 75% | (13%) |
| SAR1507-1-652 | 88% | (13%) |
| SAR1558-21-144 | 38% | (10%) |
| SAR0730-22-129 | 100%* | (13%) |
| SAR1819-1-1274 | 88% | (13%) |
| SAR2722-920-948 | 63% | (13%) |
| SAR1972-23-91 | 50% | (13%) |
| SAR2104-20-154_nativ | 63% | (13%) |
| SAR0280-28-820_nativ | 63% | (13%) |

*7 mice in group

**6 mice in group

#16 mice in group

Percentages in parentheses in control group column indicate survival rate in control group, where mice received injection with adjuvant mixture. Percentages without parentheses in control group column indicate survival rate in control group, where mice received saline only.

Results of ELISA Tests

The tables set forth on the following pages show the OD measurements and, where applicable, in vaccinated mice from the different treatment groups:

| | Test protein: SAR 2104-20-154 ELISA | | | | | | | | | | | | | |
|---|---|---|---|---|---|---|---|---|---|---|---|---|---|---|
| | Mouse | Bleed | Sera dilution (OD490 nm) | | | | | | | | | | | |
| Plate ID | No | Bleed # | 100 | 200 | 400 | 800 | 1600 | 3200 | 6400 | 12800 | 25600 | 51200 | 102400 | 204800 |
| Juni 2104 | 18 | 3 | 4 | 4 | 4 | 3.777 | 3.441 | 2.735 | 1.958 | 1.293 | 0.733 | 0.428 | 0.246 | 0.1.2 |
| Juni 2104 | 20 | 3 | 4 | 4 | 4 | 4 | 3.789 | 3.282 | 2.436 | 1.6 | 0.979 | 0.547 | 0.262 | 0.121 |
| Juni 2104 | 22 | 3 | 3.894 | 3.892 | 3.897 | 3.871 | 3.544 | 3.122 | 2.573 | 2.006 | 1.383 | 0.841 | 0.481 | 0.252 |
| Juni 2104 | 24 | 3 | 4 | 4 | 4 | 4 | 3.719 | 3.025 | 2.07 | 1.357 | 0.825 | 0.487 | 0.265 | 0.138 |
| Juni 2104 | 25 | 3 | 4 | 4 | 4 | 3.86 | 3.453 | 2.824 | 2.089 | 1.497 | 0.896 | 0.516 | 0.29 | 0.156 |
| Juni 2104 | 27 | 3 | 4 | 4 | 3.875 | 3.667 | 3.181 | 2.445 | 1.644 | 1.037 | 0.598 | 0.332 | 0.175 | 0.095 |
| Juni 2104 | 29 | 3 | 4 | 4 | 4 | 4 | 3.588 | 2.656 | 1.765 | 1.049 | 0.588 | 0.319 | 0.176 | 0.089 |
| Juni 2104 | 31 | 3 | 4 | 4 | 3.894 | 3.689 | 3.043 | 2.225 | 1.52 | 1.034 | 0.6.14 | 0.347 | 0.193 | 0.101 |

| | Test protein: SAR 0280-28-828 ELISA | | | | | | | | | | | | | |
|---|---|---|---|---|---|---|---|---|---|---|---|---|---|---|
| | Mouse | Bleed | Sera dilution (OD490 nm) | | | | | | | | | | | |
| Plate ID | No | Bleed # | 100 | 200 | 400 | 800 | 1600 | 3200 | 6400 | 12800 | 25600 | 51200 | 102400 | 204800 |
| juni 280 | 60 | 3 | 4 | 4 | 4 | 3.777 | 3.441 | 2.735 | 1.958 | 1.293 | 0.733 | 0.428 | 0.246 | 0.12 |
| juni 280 | 61 | 3 | 4 | 4 | 4 | 4 | 3.789 | 3.282 | 2.436 | 1.6 | 0.979 | 0.547 | 0.262 | 0.121 |
| juni 280 | 62 | 3 | 3.894 | 3.892 | 3.897 | 3.871 | 3.544 | 3.122 | 2.573 | 2.006 | 1.383 | 0.841 | 0.481 | 0.252 |
| juni 280 | 63 | 3 | 4 | 4 | 4 | 4 | 3.719 | 3.025 | 2.07 | 1.357 | 0.825 | 0.487 | 0.265 | 0.138 |
| juni 280 | 64 | 3 | 4 | 4 | 4 | 3.86 | 3.453 | 2.824 | 2.089 | 1.497 | 0.896 | 0.516 | 0.29 | 0.156 |
| juni 280 | 65 | 3 | 4 | 4 | 3.875 | 3.667 | 3.181 | 2.445 | 1.644 | 1.037 | 0.598 | 0.332 | 0.175 | 0.095 |
| juni 280 | 66 | 3 | 4 | 4 | 4 | 4 | 3.588 | 2.656 | 1.765 | 1.049 | 0.588 | 0.319 | 0.176 | 0.089 |
| juni 280 | 67 | 3 | 4 | 4 | 3.894 | 3.689 | 3.043 | 2.225 | 1.52 | 1.034 | 0.614 | 0.347 | 0.193 | 0.101 |

| | | | Test protein: SAR 0390-21-190 ELISA | | | | | | | | | | | |
|---|---|---|---|---|---|---|---|---|---|---|---|---|---|---|
| | Mouse | Bleed | Sera dilution (OD490 nm) | | | | | | | | | | | |
| Plate ID | No | Bleed # | 100 | 200 | 400 | 800 | 1600 | 3200 | 6400 | 12800 | 25600 | 51200 | 102400 | 204800 |
| juni 0390* | 50 | 3 | 4 | 4 | 4 | 4 | 3.593 | 2.83 | 1.979 | 1.253 | 0.714 | 0.389 | 0.208 | 0.121 |
| juni 0390** | 51 | 3 | 4 | 4 | 4 | 3.925 | 3.627 | 2.731 | 1.785 | 1.053 | 0.574 | 0.296 | 0.155 | 0.081 |
| juni 0390 | 52 | 3 | 4 | 4 | 4 | 4 | 3.516 | 2.709 | 1.86 | 1.11 | 0.627 | 0.333 | 0.182 | 0.095 |
| juni 0390 | 53 | 3 | 4 | 4 | 4 | 4 | 3.753 | 3.297 | 2.379 | 1.538 | 0.917 | 0.502 | 0.278 | 0.15 |
| juni 0390 | 54 | 3 | 4 | 4 | 4 | 4 | 3.865 | 3.446 | 2.648 | 1.799 | 1.077 | 0.6 | 0.337 | 0.163 |
| juni 0390 | 55 | 3 | 4 | 4 | 4 | 4 | 3.931 | 3.907 | 3.544 | 2.769 | 1.844 | 1.107 | 0.612 | 0.316 |
| juni 0390 | 56 | 3 | 4 | 4 | 4 | 3.864 | 3.396 | 2.59 | 1.715 | 1.043 | 0.584 | 0.317 | 0.173 | 0.093 |
| juni 0390 | 57 | 3 | 4 | 3.931 | 4 | 3.841 | 3.233 | 2.309 | 1.443 | 0.83 | 0.45 | 0.234 | 0.123 | 0.067 |

| | | | Test protein: SARO 222-27-609 ELISA | | | | | | | | | | | |
|---|---|---|---|---|---|---|---|---|---|---|---|---|---|---|
| | Mouse | Bleed | Sera dilution (OD490 nm) | | | | | | | | | | | |
| Plate ID | No | Bleed # | 100 | 200 | 400 | 800 | 1600 | 3200 | 6400 | 12800 | 25600 | 51200 | 102400 | 204800 |
| 222 | 0Ø | 3 | 3.899 | 3.646 | 3.306 | 2.755 | 2.035 | 1.351 | 0.806 | 0.485 | 0.289 | 0.177 | 0.098 | 0.06 |
| 222 | BØ | 3 | 3.011 | 2.854 | 2.518 | 1.964 | 1.485 | 0.969 | 0.607 | 0.375 | 0.243 | 0.128 | 0.077 | 0.04 |
| 222 | VØ | 3 | 3.669 | 3.294 | 2.737 | 1.98 | 1.314 | 0.784 | 0.451 | 0.268 | 0.175 | 0.098 | 0.063 | 0.034 |
| 222 | HØ | 3 | 3.535 | 3.375 | 3.24 | 2.814 | 2.317 | 1.824 | 1.466 | 1.166 | 0.889 | 0.576 | 0.344 | 0.185 |
| 222 | 20Ø | 3 | 3.055 | 2.927 | 2.803 | 2.498 | 1.949 | 1.513 | 1.087 | 0.756 | 0.481 | 0.283 | 0.157 | 0.086 |
| 222 | 2BØ | 3 | 2.568 | 2.281 | 1.871 | 1.331 | 0.84 | 0.471 | 0.267 | 0.145 | 0.084 | 0.049 | 0.029 | 0.017 |
| 222 | 2HØ | 3 | 4 | 3.816 | 3.646 | 3.093 | 2.389 | 1.66 | 1.033 | 0.628 | 0.415 | 0.25 | 0.143 | 0.077 |
| 222 | 2VØ | 3 | 4 | 3.827 | 3.552 | 3.05 | 2.385 | 1.665 | 1.065 | 0.642 | 0.365 | 0.203 | 0.127 | 0.062 |

| | | | Test protein: SAR0872-27-273 ELISA | | | | | | | | | | | |
|---|---|---|---|---|---|---|---|---|---|---|---|---|---|---|
| | Mouse | Bleed | Sera dilution (OD490 nm) | | | | | | | | | | | |
| Plate ID | No | Bleed # | 100 | 200 | 400 | 800 | 1600 | 3200 | 6400 | 12800 | 25600 | 51200 | 102400 | 204800 |
| 0872 | 2 | 3 | 4 | 4 | 4 | 4 | 4 | 4 | 4 | 4 | 4 | 3.564 | 2.528 | 1.57 |
| 0872 | 4 | 3 | 4 | 4 | 4 | 4 | 4 | 4 | 4 | 3.944 | 3.476 | 2.441 | 1.561 | 0.917 |
| 0872 | 6 | 3 | 4 | 4 | 4 | 4 | 4 | 4 | 4 | 4 | 3.931 | 3.367 | 2.446 | 1.57 |
| 0872 | 8 | 3 | 4 | 4 | 4 | 4 | 4 | 4 | 4 | 4 | 4 | 3.777 | 2.732 | 1.739 |
| 0872 | 1.7 | 3 | 4 | 4 | 4 | 4 | 4 | 4 | 4 | 4 | 3.72.4 | 2.838 | 1.913 | 1.158 |
| 0872 | 19 | 3 | 4 | 4 | 4 | 4 | 4 | 4 | 4 | 3.786 | 3.121 | 2.237 | 1.409 | 0.811 |
| 0872 | 21 | 3 | 4 | 4 | 4 | 4 | 4 | 4 | 4 | 4 | 3.566 | 2.552 | 1.615 | 0.901 |
| 0872 | 23 | 3 | 4 | 4 | 4 | 4 | 4 | 4 | 4 | 4 | 3.887 | 3.269 | 2.251 | 1.404 |

| | | | Test protein: SAR1879-24-184 ELISA | | | | | | | | | | | |
|---|---|---|---|---|---|---|---|---|---|---|---|---|---|---|
| | Mouse | Bleed | Sera dilution (OD490 nm) | | | | | | | | | | | |
| Plate ID | No | Bleed # | 1.00 | 200 | 400 | 800 | 1600 | 3200 | 6400 | 12800 | 25600 | 51200 | 102400 | 204800 |
| 1879 | 0Ø | 3 | 4 | 4 | 4 | 4 | 4 | 4 | 4 | 3.871 | 3.028 | 2.038 | 1.228 | 0.662 |
| 1879 | VØ | 3 | 4 | 4 | 4 | 4 | 4 | 4 | 3.508 | 2.428 | 1.548 | 0.881 | 0.478 | 0.242 |
| 1879 | HØ | 3 | 4 | 4 | 4 | 4 | 4 | 4 | 3.665 | 2.686 | 1.778 | 1.041 | 0.577 | 0.301 |
| 1879 | 20Ø | 3 | 4 | 4 | 4 | 4 | 4 | 4 | 3.501 | 2.468 | 1.548 | 0.856 | 0.474 | 0.244 |

-continued

| Plate ID | Mouse No | Bleed # | 1.00 | 200 | 400 | 800 | 1600 | 3200 | 6400 | 12800 | 25600 | 51200 | 102400 | 204800 |
|---|---|---|---|---|---|---|---|---|---|---|---|---|---|---|
| Test protein: SAR1879-24-184 ELISA | | | Sera dilution (OD490 nm) | | | | | | | | | | | |
| 1879 | 2BØ | 3 | 4 | 4 | 4 | 4 | 4 | 3.872 | 3.175 | 2.12 | 1.333 | 0.747 | 0.406 | 0.213 |
| 1879 | 2VØ | 3 | 4 | 4 | 4 | 4 | 4 | 4 | 4 | 3.52 | 2.453 | 1.483 | 0.821 | 0.428 |
| 1879 | 2HØ | 3 | 4 | 4 | 4 | 4 | 4 | 3.885 | 3.363 | 2.325 | 1.452 | 0.826 | 0.448 | 0.224 |

| Plate ID | Mouse No | Bleed # | 100 | 200 | 400 | 800 | 1600 | 3200 | 6400 | 12800 | 25600 | 51200 | 102400 | 204800 |
|---|---|---|---|---|---|---|---|---|---|---|---|---|---|---|
| Test protein: SAR1881-25-208 ELISA | | | Sera dilution (OD490 nm) | | | | | | | | | | | |
| 1881 | 0Ø | 3 | 4 | 4 | 3.66 | 3.06 | 2.238 | 1.454 | 0.848 | 0.47 | 0.251 | 0.135 | 0.078 | 0.047 |
| 1881 | BØ | 3 | 4 | 4 | 3.558 | 2.546 | 1.551 | 0.884 | 0.481 | 0.26 | 0.137 | 0.075 | 0.048 | 0.032 |
| 1881 | VØ | 3 | 4 | 4 | 3.78 | 2.952 | 1.888 | 1.105 | 0.617 | 0.335 | 0.181 | 0.102 | 0.058 | 0.039 |
| 1881 | HØ | 3 | 4 | 3.595 | 2.644 | 1.678 | 0.983 | 0.546 | 0.3 | 0.162 | 0.091 | 0.053 | 0.035 | 0.026 |
| 1881 | 20Ø | 3 | 4 | 4 | 4 | 4 | 3.583 | 3.018 | 2.231 | 1.454 | 0.866 | 0.478 | 0.258 | 0.141 |
| 1881 | 2BØ | 3 | 1.195 | 0.577 | 0.316 | 0.171 | 0.101 | 0.064 | 0.044 | 0.032 | 0.027 | 0.022 | 0.022 | 0.019 |
| 1881 | 2VØ | 3 | 4 | 3.792 | 3.313 | 2.508 | 1.716 | 1.024 | 0.598 | 0.333 | 0.181 | 0.1 | 0.06 | 0.039 |
| 1881 | 2HØ | 3 | 0.995 | 0.559 | 0.3 | 0.165 | 0.097 | 0.061 | 0.043 | 0.033 | 0.026 | 0.02 | 0.019 | 0.02 |

| Plate ID | Mouse No | Bleed # | 100 | 200 | 400 | 800 | 1600 | 3200 | 6400 | 1.2800 | 25600 | 51200 | 102400 | 204800 |
|---|---|---|---|---|---|---|---|---|---|---|---|---|---|---|
| Test protein: SAR2104-20-154 ELISA | | | Sera dilution (OD490 nm) | | | | | | | | | | | |
| 2104 | 0Ø | 3 | 4 | 4 | 4 | 4 | 4 | 4 | 3.841 | 3.033 | 2.031 | 1.197 | 0.674 | 0.371 |
| 2104 | BØ | 3 | 0.67 | 0.377 | 0.22 | 0.138 | 0.089 | 0.067 | 0.052 | 0.048 | 0.044 | 0.042 | 0.041 | 0.04 |
| 2104 | VØ | 3 | 0.276 | 0.165 | 0.099 | 0.073 | 0.057 | 0.053 | 0.047 | 0.045 | 0.043 | 0.042 | 0.041 | 0.039 |
| 2104 | 20Ø | 3 | 0.153 | 0.099 | 0.071 | 0.057 | 0.048 | 0.047 | 0.043 | 0.043 | 0.044 | 0.042 | 0.041 | 0.039 |
| 2104 | 2BØ | 3 | 0.458 | 0.378 | 0.285 | 0.244 | 0.2 | 0.169 | 0.135 | 0.099 | 0.07 | 0.052 | 0.047 | 0.043 |
| 2104 | 2VØ | 3 | 0.349 | 0.25 | 0.178 | 0.133 | 0.098 | 0.09 | 0.067 | 0.041 | 0.046 | 0.043 | 0.042 | 0.039 |
| 2104 | 2HØ | 3 | 0.345 | 0.221 | 0.142 | 0.103 | 0.074 | 0.06 | 0.051 | 0.047 | 0.044 | 0.041 | 0.042 | 0.037 |

| Plate ID | Mouse No | Bleed # | 100 | 200 | 400 | 800 | 1600 | 3200 | 6400 | 12800 | 25600 | 51200 | 102400 | 204800 |
|---|---|---|---|---|---|---|---|---|---|---|---|---|---|---|
| Test protein: SAR2119-34-370 ELISA | | | Sera dilution (OD490 nm) | | | | | | | | | | | |
| 2119 | 0Ø | 3 | 4 | 4 | 4 | 3.857 | 4 | 4 | 3.689 | 3.27 | 1.839 | 1.121 | 0.597 | 0.311 |
| 2119 | BØ | 3 | 4 | 4 | 4 | 4 | 4 | 4 | 3.872 | 3.379 | 2.373 | 1.49 | 0.827 | 0.434 |
| 2119 | VØ | 3 | 4 | 4 | 3.949 | 4 | 4 | 4 | 3.892 | 3.218 | 2.22 | 1.339 | 0.751 | 0.381 |
| 2119 | HØ | 3 | 0.187 | 0.101 | 0.168 | 0.102 | 0.062 | 0.041 | 0.03 | 0.022 | 0.017 | 0.017 | 0.015 | 0.011 |
| 2119 | 20Ø | 3 | 4 | 4 | 4 | 4 | 3.421 | 2.446 | 1.457 | 0.819 | 0.439 | 0.228 | 0.122 | 0.063 |
| 2119 | 2BØ | 3 | 4 | 4 | 4 | 4 | 4 | 4 | 4 | 3.594 | 2.695 | 1.747 | 1.026 | 0.547 |
| 2119 | 2VØ | 3 | 4 | 4 | 4 | 4 | 3.577 | 2.731 | 1.734 | 1.012 | 0.552 | 0.285 | 0.146 | 0.076 |
| 2119 | 2HØ | 3 | 4 | 4 | 4 | 4 | 3.498 | 2.52 | 1.521 | 0.874 | 0.466 | 0.244 | 0.128 | 0.066 |

| | Test protein: SAR2718-24-157 ELISA | | | | | | | | | | | | | |
|---|---|---|---|---|---|---|---|---|---|---|---|---|---|---|
| | Mouse | Bleed | Sera dilution (OD490 nm) | | | | | | | | | | | |
| Plate ID | No | Bleed # | 1.00 | 200 | 400 | 800 | 1600 | 3200 | 6400 | 12800 | 25600 | 51.200 | 102400 | 204800 |
| 2718 | 0Ø | 3 | 4 | 4 | 4 | 4 | 4 | 3.906 | 3.27 | 2.491 | 1.673 | 1.062 | 0.616 | 0.323 |
| 2718 | VØ | 3 | 3.923 | 4 | 4 | 3.786 | 3.09 | 2.101 | 1.238 | 0.682 | 0.366 | 0.19 | 0.105 | 0.057 |
| 2718 | HØ | 3 | 4 | 4 | 4 | 4 | 4 | 3.944 | 3.498 | 2.547 | 1.622 | 0.963 | 0.514 | 0.27 |
| 2718 | 20Ø | 3 | 4 | 4 | 4 | 4 | 3.944 | 2.971 | 1.885 | 0.966 | 0.449 | 0.187 | 0.086 | 0.047 |
| 2718 | 2BØ | 3 | 4 | 4 | 3.885 | 3.344 | 3.204 | 1.371 | 0.773 | 0.402 | 0.216 | 0.115 | 0.06 | 0.037 |
| 2718 | 2VØ | 3 | 4 | 4 | 4 | 4 | 3.801 | 2.893 | 1.911 | 1.17 | 0.632 | 0.349 | 0.174 | 0.091 |
| 2718 | 2HØ | 3 | 4 | 4 | 4 | 3.726 | 3.229 | 1.844 | 1.104 | 0.595 | 0.324 | 0.174 | 0.093 | 0.051 |

| | Test protein: SAR0826-42-209 ELISA | | | | | | | | | | | | | |
|---|---|---|---|---|---|---|---|---|---|---|---|---|---|---|
| | Mouse | Bleed | Sera dilution (OD490 nm) | | | | | | | | | | | |
| Plate ID | No | Bleed # | 100 | 200 | 400 | 800 | 1600 | 3200 | 6400 | 12800 | 25600 | 51200 | 102400 | 204800 |
| 0826 | 1 | 3 | −0.0058 | −0.0288 | −0.0138 | −0.0258 | −0.0128 | −0.0288 | 0.0132 | 0.0062 | −0.0688 | −0.0098 | −0.0398 | −0.0178 |
| 0826 | 2 | 3 | 0.2672 | −0.0188 | −0.0668 | −0.0888 | −0.1188 | −0.1038 | −0.1288 | −0.1168 | −0.1188 | −0.1068 | −0.0698 | 0.3492 |
| 0826 | 3 | 3 | −0.0828 | −0.1518 | −0.1278 | −0.1308 | −0.1268 | −0.1168 | −0.1288 | −0.1338 | −0.0558 | −0.1118 | −0.0968 | −0.0378 |
| 0826 | 4 | 3 | −0.0918 | −0.1458 | −0.1308 | −0.1448 | −0.1408 | −0.1318 | −0.1518 | −0.1398 | −0.1328 | −0.1168 | −0.1068 | −0.0588 |
| 0826 | 5 | 3 | 0.0922 | −0.1228 | −0.1448 | −0.1438 | −0.1168 | −0.1198 | −0.0918 | −0.1388 | −0.1288 | −0.1138 | −0.1228 | −0.0908 |
| 0826 | 6 | 3 | 1.1902 | 0.4132 | 0.0792 | −0.0518 | −0.1048 | −0.1448 | −0.1378 | −0.1568 | −0.1378 | −0.1168 | −0.1168 | −0.0678 |
| 0826 | 7 | 3 | 3.1572 | 2.6172 | 1.6322 | 0.8702 | 0.3652 | 0.1352 | −0.0218 | −0.0928 | −0.0928 | −0.0988 | −0.0948 | −0.0718 |
| 0826 | 8 | 3 | −0.1568 | −0.1638 | −0.1168 | −0.1198 | −0.0238 | 0.0102 | −0.0388 | −0.0828 | −0.0818 | −0.0618 | −0.0368 | −0.0038 |

Immune Fluorescence/FACS Analyses of Plasma Samples from Immunized Mice

1. Groups of mice will be immunized three times with intervals of 14 days with antigen coupled onto carrier-proteins, diphtheria-toxoid and/or secreted mycobacterial proteins (PPD). All immunizations are carried out subcutaneously with the antigen adsorbed onto $Al(OH)_3$ and with Freunds incomplete adjuvant, cf. above.
2. A control group of mice are immunized with diphtheria-toxoid without antigen.
3. Mice are bled after the second and the third immunization.
4. The serum bleeds are tested for their reactivity against the immunizing antigen.
5. The following methods will be used:

Direct measurement of antibodies to the immunizing antigen

Analysis for agglutinating power when antibodies are incubated with the bacteria Analysis for killing effect on bacteria after incubation of bacteria with antiserum+fresh serum (complement)

Proteins of the Invention

The *S. aureus* proteins of the present invention are set forth in the sequence listing together with their related nucleic acid sequences. For easy reference, the one letter amino acid sequences of the *S. aureus* proteins are provided in the following:

```
SEQ ID NO: 1:
MKRLLGLLLVSTLVLSACGNDENQEESKKEVKSKEKKIEKEKENKSKKDKEKEVATQQQPDNQTVEQPQ

SQEQSVQQPQQQIPQNSVPQQNVQVQQNKKQKVDLNNMPPTDFSTEGMSEQAQKQIEELSMQKDYHG

LSQREYNDRVSEIINNDN

SEQ ID NO: 2:
MLKGCGGCLISFIILIILLSACSMMFSNNDNSTSNQSSKTQLTQKDEDKSENMPEEKSESETDKDLQSTE

EVPANENTENNQHEIDEITTIDQSDDEINTPNVAEEESQDDLKDDLKEKQQPSDHHQSTQPKTSPSTETN

KQQSFANCKQLRQVYPNGVTADHPAYRPHLDRDKDKRACEPDKY

SEQ ID NO: 3:
MKKLIISIMAINLFLTGCGKSQEKATLEKDIDNLQKENKELKDKKEKLQQEKEKLADKQKDLEKEVKDLKP

SKEDNKDDKKDEDKNKDKDKEASQDKQSKDQTKSSDKDNHKKPTSTDKDQKANDKHQS
```

-continued

SEQ ID NO: 4:
MKNAFKLFKMDLKKVAKTPAVWIILAGLAILPSFYAWFNLWAMWDPYGNTGHIKVAVVNEDKGDTIRGK

KVNVGNTMVNTLKKNKSFDWQFVSREKADHEIKMGKYFAGIYIPSKFTHEITGTLRKQPQKADVEFKVNQ

KINAVASKLTDTGSSVVVEKANEQFNKTVTRALLEEANKAGLTIEENVPTINKIKNAVYSADKALPKINDFA

NKIVYLNNHQADLDKYANDFRKLGNYKGDILDAQKKLNEVNGAIPQLNEKAKLILALNNYMPKIEKALNFA

ADDVPAQFPKINQGLNIASQGIDQANGQLNDAKGFVTQVRSRVGDYQEAIRRAQDLNRRNQQQIPQNS

AANNETSNSAPAAGNGVTSTPPSAPNGNTTPNNNVTQNTAPNSNNAPVSTTPQSTSGKKDGQSFADITT

TQVSTANENTQNITDKDVKSMEAALTGSLLSLSNNLDTQAKAAQKDSQALRNISYGILASDKPSDFRESL

DNVKSGLEYTTQYNQQFIDTLKEIEKNENVDLSKEIDKVKTANNRINESLRLVNQLSNALKNGSSGTAEAT

KLLDQLSKLDSSLSSFRDYVKKDLNSSLVSISQRIMDELNKGQTALSNVQSKLNTIDQVINSGQSILKNG

KTRIDRLQTVLPSIEQQYISAIKNAQANFPKVKSDVAKAANFVRNDLPQLEQRLTNATASVNKNLPTLLNG

YDQAVGLLNKNQPQAKKALSDLADFAQNKLPDVEKDLKKANKIFKKLDKDDAVDKLIDTLKNDLKKQAGI

IANPINKKTVDVFPVKDYGSGMTPFYTALSVWVGALLMVSLLTVDNKHKSLEPVLTTRQVFLGKAGFFIML

GMLQALIVSVGDLLILKAGVESPVLFVLITIFCSIIFNSIVYTCVSLLGNPGKAIAIVLLVLQIAGGGGTFPIQT

TPQFFQNISPYLPFTYAIDSLRETVGGIVPEILITKLIILTLFGIGFFVVGLILKPVTDPLMKRVSEKVDQSNVT

E

SEQ ID NO: 5:
MNEKVEGMTLELKLDHLGVQEGMKGLKRQLGVVNSEMKANLSAFDKSEKSMEKYQARIKGLNDRLKVQ

KKMYSQVEDELKQVNANYQKAKSSVKDVEKAYLKLVEANKKEKLALDKSKEALKSSNTELKKAENQYKR

TNQPRKQDAYQKLKQLRDAEQKLKNSNQATTAQLKRASDAVQKQSAKHKALVEQYKQEGNQVQKLKVQ

NDNLSKSNDKIESSYAKTNTKLKQTEKEFNDLNNTIKNHSANVAKAETAVNKEKAALNNLERSIDKASSE

MKTFNKEQMIAQSHFGKLASQADVMSKKFSSIGDKMTSLGRTMTMGVSTPITLGLGAALKTSADFEGQM

SRVGAIAQASSKDLKSMSNQAVDLGAKTSKSANEVAKGMEELAALGFNAKQTMEAMPGVISAAEASGAE

MATTATVMASAINSFGLKASDANHVADLLARSANDSAADIQYMGDALKYAGTPAKALGVSIEDTSAAIEV

LSNSGLEGSQAGTALRASFIRLANPSKNTAKEMKKLGIHLSDAKGQFVGMGELIRQFQDNMKGMTREQK

LATVATIVGTEAASGFLALIEAGPDKINSYSKSLKNSNGESKKAADLMKDNLKGALEQLGGAFESLAIEVG

KDLTPMIRAGAEGLTKLVDGFTHLPGWVRKASVGLALFGASIGPAVLAGGLLIRAVGSAAKGYASLNRRIA

ENTILSNTNSKAMKSLGLQTLFLGSTTGKTSKGFKGLAGAMLFNLKPINVLKNSAKLAILPFKLLKNGLGLA

AKSLFAVSGGARFAGVALKFLTGPIGATITAITIAYKVFKTAYDRVEWFRNGINGLGETIKFFGGKIIGGAV

RKLGEFKNYLGSIGKSFKEKFSKDMKDGYKSLSDDDLLKVGVNKFKGFMQTMGTASKKASDTVKVLGKG

VSKETEKALEKYVHYSEENNRIMEKVRLNSGQITEDKAKKLLKIEADLSNNLIAEIEKRNKKELEKTQELID

KYSAFDEQEKQNILTRTKEKNDLRIKKEQELNQKIKELKEKALSDGQISENERKEIEKLENQRRDITVKELS

KTEKEQERILVRMQRNRNSYSIDEASKAIKEAEKARKAKKKEVDKQYEDDVIAIKNNVNLSKSEKDKLLAI

ADQRHKDEVRKAKSKKDAVVDVVKKQNKDIDKEMDLSSGRVYKNTEKWWNGLKSWWSNFREDQKKK

SDKYAKEQEETARRNRENIKKWFGNAWDGVKSKTGEAFSKMGRNANHFGGEMKKMWSGIKGIPSKLS

SGWSSAKSSVGYHTKAIANSTGKWFGKAWQSVKSTTGSIYNQTKQKYSDASDKAWAHSKSIWKGTSK

WFSNAYKSAKGWLTDMANKSRSKWDNISSTAWSNAKSVWKGTSKWFSNSYKSLKGWTGDMYSRAH

DRFDAISSSAWSNAKSVFNGFRKWLSRTYEWIRDIGKDMGRAAADLGKNVANKAIGGLNSMIGGINKIS

KAITDKNLIKPIPTLSTGTLAGKGVATDNSGALTQPTFAVLNDRGSGNAPGGGVQEVIHRADGTFHAPQG

RDVVVPLGVGDSVINANDTLKLQRMGVLPKFHGGTKKKKWMEQVTENLGKKAGDFGSKAKNTAHNIKK

GAEEMVEAAGDKIKDGASWLGDKIGDVWDYVQHPGKLVNKVMSGLNINFGGGANATVKIAKGAYSLLK

-continued

KKLVDKVKSWFEDFGGGGDGSYLFDHPIWQRFGSYTGGLNFNGGRHYGIDFQMPTGTNIYAVKGGIAD

KVWTDYGGGNSIQIKTGANEWNWYMHLSKQLARQGQRIKAGQLIGKSGATGNFVRGAHLHFQLMQGS

HPGNDTAKDPEKWLKSLKGSGVRSGSGVNKAASAWAGDIRRAAKRMGVNVTSGDVGNIISLIQHESGG

NAGITQSSALRDINVLQGNPAKGLLQYIPQTFRHYAVRGHNNIYSGYDQLLAFFNNSYWRSQFNPRGGW

SPSGPRRYANGGLITKHQLAEVGEGDKQEMVIPLTRRKRAIQLTEQVMRIIGMDGKPNNITVNNDTSTVE

KLLKQIVMLSDKGNKLTDALIQTVSSQDNNLGSNDAIRGLEKILSKQSGHRANANNYMGGLTN

SEQ ID NO: 6:
MKKQIISLGALAVASSLFTWDNKADAIVTKDYSKESRVNENSKYDTPIPDWYLGSILNRLGDQIYYAKELT

NKYEYGEKEYKQAIDKLMTRVLGEDHYLLEKKKAQYEAYKKWFEKHKSENPHSSLKKIKFDDFDLYRLTK

KEYNELHQSLKEAVDEENSEVKNIQSKQKDLLPYDEATENRVTNGIYDFVCEIDTLYAAYFNHSQYGHNA

KELRAKLDIILGDAKDPVRITNERIRKEMMDDLNSIIDDFFMDTNMNRPLNITKFNPNIHDYTNKPENRDN

FDKLVKETREAIANADESWKTRTVKNYGESETKSPVVKEEKKVEEPQLPKVGNQQEDKITVGTTEEAPLPI

AQPLVKIPQGTIQGEIVKGPEYLTMENKTLQGEIVQGPDFPTMEQNRPSLSDNYTQPTTPNPILKGIEGNST

KLEIKPQGTESTLKGTQGESSDIEVKPQATETTEASHYPARPQFNKTPKYVKYRDAGTGIREYNDGTFGYE

ARPRFNKPSETNAYNVTTNQDGTVSYGARPTQNKPSETNAYNVTTHANGQVSYGARPTQNKPSETNAYN

VTTHANGQVSYGARPTQNKPSKTNAYNVTTHADGTATYGPRVTK

SEQ ID NO: 7:
MKKVIGLLLVSTLALTACGEKEKPKKEENKKSQTQKHKDSKPKTQQEKMKKVEDKNPPNNSIQNNSNNQ

NQSQNNQLNNNSDPSNNTPANINKNDSQNTNLNDEYVVSPGWTKDEQAKAFEEYKKGKEDEARAGAS

AVPGANIN

SEQ ID NO: 8:
MAKKFNYKLPSMVALTLVGSAVTAHQVQAAETTQDQTTNKNVLDSNKVKATTEQAKAEVKNPTQNISGT

QVYQDPAIVQPKAANKTGNAQVNQKVDTTQVNGDTRATQSTTSNNAKPVTKSTNTTAPKTNNNVTSAG

YSLVDDEDDNSENQINPELIKSAAKPAALETQYKAAAPKATPVAPKAKTEATPKVTTFSASAQPRSAAAAP

KTSLPKYKPQVNSSINDYIRKNNLKAPKIEEDYTSYFPKYAYRNGVGRPEGIVVHDTANDRSTINGEISYM

KNNYQNAFVHAFVDGDRIIETAPTDYLSWGVGAVGNPRFINVEIVHTHDYASFARSMNNYADYAATQLQ

YYGLKPDSAEYDGNGTVWTHYAVSKYLGGTDHADPHGYLRSHNYSYDQLYDLINEKYLIKIMGKVAPWGT

QSTTTPTTPSKPSTPSKPSTPSTGKLTVAANNGVAQIKPTNSGLYTTVYDKTGKATNEVQKTFAVSKTATL

GNQKFYLVQDYNSGNKFGWVKEGDVVYNTAKSPVNVNQSYSIKPGTKLYTVPWGTSKQVAGSVSGSGN

QTFKASKQQQIDKSIYLYGSVNGKSGWVSKAYLVDTAKPTPTPTPKPSTPTTNNKLTVSSLNGVAQINAK

NNGLFTTVYDKTGKPTKEVQKTFAVTKEASLGGNKFYLVKDYNSPTLIGWVKQGDVIYNNAKSPVNVMQ

TYTVKPGTKLYSVPWGTYKQEAGAVSGTGNQTFKATKQQQIDKSIYLYGTVNGKSGWISKAYLAVPAAPK

KAVAQPKTAVKAYAVTKPQTTQTVSKIAQVKPNNTGIRASVYEKTAKNGAKYADRTFYVTKERAHGNETY

VLLNNTSHNIPLGWFNVKDLNVQNLGKEVKTTQKYTVNRSNNGLSMVPWGTKNQVILTGNNIAQGTFNA

TKQVSVGKDVYLYGTINNRTGWVNSKDLTAPTAVKPTTSAAKDYNYTYVIKNGNGYYYVTPNSDTAKYSL

KAFNEQPFAVVKEQVINGQTWYYGKLSNGKLAWIKSTDLAKELIKYNQIGMTLNQVAQIQAGLQYKPQV

QRVPGKWTDANFNDVKHAMDTKRLAQDPALKYQFLRLDQPQNISIDKINQFLKGKGVLENQGAAFNKAA

QMYGINEVYLISHALLETGNGTSQLAKGADVVNNKVVTNSNTKYHNVFGIAAYDNDPLREGIKYAKQAG

WDTVSKAIVGGAKFIGNSYVKAGQNTLYKMRWNPAHPGTHQYATDVDWANINAKIIKGYYDKIGEVGKY

FDIPQYK

SEQ ID NO: 9:
MSNNFKDDFEKNRQSIDTNSHQDHTEDVEKDQSELEHQDTIENTEQQFPPRNAQRRKRRRDLATNHNK

QVHNESQTSEDNVQNEAGTIDDRQVESSHSTESQEPSHQDSTPQHEEGYYNKNAFAMDKSHPEPIEDN

-continued

DKHETIKEAENNTEHSTVSDKSEAEQSQQPKPYFATGANQANTSKDKHDDVTVKQDKDESKDHHSGKK

GAAIGAGTAGVAGAAGAMGVSKAKKHSNDAQNKSNSGKVNNSTEDKASEDKSKEHHNGKKGAAIGAG

TAGLAGGAASNSASAASKPHASNNASQNNDEHDHHDRDKERKKGGMAKVLLPLIAAVLIIGALAIFGGM

ALNNHNNGTKENKIANTNKNNADESKDKDTSKDASKDKSKSTDSDKSKDDQDKATKDESDNDQNNAN

QANNQAQNNQNQQQANQNQQQQQQRQGGGQRHTVNGQENLYRIAIQYYGSGSPENVEKIRRANGLS

GNNIRNGQQIVIP

SEQ ID NO: 10:
MSWFDKLFGEDNDSNDDLIHRKKKRRQESQNIDNDHDSLLPQNNDIYSRPRGKFRFPMSVAYENENVE

QSADTISDEKEQYHRDYRKQSHDSRSQKRHRRRRNQTTEEQNYSEQRGNSKISQQSIKYKDHSHYHTN

KPGTYVSAINGIEKETHKSKTHNIYSNNTNHRAKDSTTDYHKESFKTSEVPSAIFGTMKPKKLENGRIPVS

KSSEKVESDKQKYDKYVAKTQTSQNKHLEQEKQKDSVVKQGTASKSSDENVSSTTKSTPNYSKVDNTIK

IENIYASQIVEEIRRERERKVLQKRRFKKALQQKREEHKNEEQDAIQRAIDEMYAKQAERYVGDSSLNDD

SDLTDNSTEASQLHTNEIEDEAVSNDENKKASIQNEDTDDTHVDESPYNYEEVSLNQVSTTKQLSDDEV

TVSDVTSQRQSALQHNVEVNNQDELKNQSRLIADSEEDGATNEEEYSGSQIDDAEFYELNDTEVDEDTT

SNSEDNTNRDASEMHVDAPKTQEHAVTESQVNNIDKTVDNEIELAPRHKKDDQTNLSVNSLKTNDVND

GHVVEDSSMNEIEKQNAEITENVQNEAAESKQNVEEKTIENVNPKKQTEKVSTLSKRPFNVVMTPSDKKR

MMDRKKHSKVNVPELKPVQSKQAASESKTATQNTPSSSTDSQESNTNAYKTNNMTSNNVENNQLIGHA

ATENDYQNAQQYSEQKPSADSTQTEIFEESQDDNQLENEQVDQSTSSSVSEVSDITEESEETTHQNNTS

GQQDNDDQQKDLQLSFSNQNEDTANENRPRTNQPDVATNQAVQTSKPMIRKGPNIKLPSVSLLEEPQVI

EPDEDWITDKKKELNDALFYFNVPAEVQDVTEGPSVTRFELSVEKGVKVSRITALQDDIKMALAAKDIRIE

APIPGTSRVGIEVPNQNPTTVNLRSIIESPSFKNAESKLTVAMGYRINNEPLLMDIAKTPHALIAGATGSGK

SVCINSILMSLLYKNHPEELRLLLIDPKMVELAPYNGLPHLVAPVITDVKAATQSLKWAVEEMERRYKLFAH

YHVRNITAFNKKAPYDERMPKIVIVIDELADLMMMAPQEVEQSIARIAQKARACGIHMLVATQRPSVNVIT

GLIKANIPTRIAFMVSSSVDSRTILDSGGAERLLGYGDMLYLGSGMNKPIRVQGTFVSDDEIDDVVDFIKQ

QREPDYLFEEKELLKKTQTQSQDELFDDVCAFMVNEGHISTSLIQRHFQIGYNRAARIIDQLEQLGYVSSA

NGSKPRDVYVTEADLNKE

SEQ ID NO: 11:
MSNQNYDYNKNEDGSKKKMSTTAKVVSIATVLLLLGGLVFAIFAYVDHSNKAKERMLNEQKQEQKEKRQ

KENAEKERKKKQQEEKEQNELDSQANQYQQLPQQNQYQYVPPQQQAPTKQRPAKEENDDKASKDESK

DKDDKASQDKSDDNQKKTDDNKQPAQPKPQPQQPTPKPNNNQQNNQSNQQAKPQAPQQNSQSTTNK

QNNANDK

SEQ ID NO: 12:
MKLKSLAVLSMSAVVLTACGNDTPKDETKSTESNTNQDTNTTKDVIALKDVKTSPEDAVKKAEETYKGQK

LKGISFENSNGEWAYKVTQQKSGEESEVLVDDKNKKVINKKTEKEDTVNENDNFKYSDAIDYKKAIKEG

QKEFDGDIKEWSLEKDDGKLVYNIDLKKGNKKQEVTVDAKNGKVLKSEQDQ

SEQ ID NO: 13:
MKKKNWIYALIVTLIIIIAIVSMIFFVQTKYGDQSEKGSQSVSNKNNKIHIAIVNEDQPTTYNGKKVELGQA

FIKRLANEKNYKFETVTRNVAESGLKNGGYQVMIVIPENFSKLAMQLDAKTPSKISLQYKTAVGQKEEVAK

NTEKVVSNVLNDFNKNLVEIYLTSIIDNLHNAQKNVGAIMTREHGVNSKFSNYLLNPINDFPELFTDTLVNS

ISANKDITKWFQTYNKSLLSANSDTFRVNTDYNVSTLIEKQNSLFDEHNTAMDKMLQDYKSQKDSVELD

NYINALKQMDSQIDQQSSMQDTGKEEYKQTVKENLDKLREIIQSQESPFSKGMIEDYRKQLTESLQDELA

NNKDLQDALNSIKMNNAQFAENLEKQLHDDIVKEPDSDTTFIYNMSKQDFIAAGLNEDEANKYEAIVKEA

-continued

KRYKNEYNLKKPLAEHINLTDYDNQVAQDTSSLINDGVKVQRTETIKSNDINQLTVATDPHFNFEGDIKIN

GKKYDIKDQSVQLDTSNKEYKVEVNGVAKLKKDAEKDFLKDKTMHLQLLFGQANRQDEPNDKKATSVV

DVTLNHNLDGRLSKDALSQQLSALSRFDAHYKMYTDTKGREDKPFDNKRLIDMMVDQVINDMESFKDD

KVAVLHQIDSMEENSDKLIDDILNNKKNTTKNKEDISKLIDQLENVKKTFAEEPQEPKIDKGKNDEFNTMS

SNLDKEISRISEKSTQLLSDTQESKTIADSVSGQLNQLDNNVNKLHATGRALGVRANDLNRQMAKNDKD

NELFAKEFKKVLQNSKDGDRQNQALKAFMSNPVQKKNLENVLANNGNTDVISPTLFVLLMYLLSMITAYIF

YSYERAKGQMNFIKDDYSSKNNLWNNAITSGVIGATGLVEGLIVGLIAMNKFHVLAGYRAKFILMVILTM

MVFVLINTYLLRQVKSIGMFLMIAALGLYFVAMNNLKAAGQGVTNKISPLSYIDNMFFNYLNAEHPIGLALV

ILTVLVIIGFVLNMFIKHFKKERLI

SEQ ID NO: 14:
MTQQQNNKRTLKNKHTYQNEPLPNRKDFVVSFITGALVGSALGLYFKNKVYQKADDLKVKEQELSQKFEE

RKTQLEETVAFTKERVEGFLNKSKNEQAALKAQQAAIKEEASANNLSDTSQEAQEIQEAKREAQTETDKS

AAVSNEESKASALKAQQAAIKEEASANNLSDTSQEAQAIQEVKKEAQAETDKSADVSNEESKASTLNVS

KEESQAERLANAAKQKQAKLTPGSKESQLTEALFAEKPVAKNDLKEIPLLVTKKNDVSETVNTDNKDTVK

QKEAKFENGVITRKADEKTPNNTAVDKKSGKQSKKTTPSNKRNASKASTNKTSGQKKQHNKKASQGAK

KQSSSSNSTTKTNQKNSKATNAKSSNASKKSNAKVEKAKSKIEKRTFND

SEQ ID NO: 15:
MDIGKKHVIPKSQYRRKRREFFHNEDREENLNQHQDKQNIDNTTSKKADKQIHKDSIDKHERFKNSLSS

HLEQRNRDVNENKAEESKSNQGSKSAYNKDHYLTDDVSKKQNSLDSVDQDTEKSKYYEQNTEATLSTN

STDKVESTDMRKLSSDKNKVGHEEQHVLSKPSEHDKETRIDFESSRTDSDSSMQTEKIKKDSSDGNKS

SNLKSEVISDKSNSVPILSESDDEVNNQKPLTLPEEQKLKRQQSQNEQTKTYTYGDSEQNDKSNHENDL

SHHTPSISDDKDYVMREDHIVDDNPDNDINTPSLSKIDDDRKLDEKIHVEDKHKQNADSSETVGYQSQS

SASHRSTEKRNMAINDHDKLNGQKPNTKTSANNNQKKATSKLNKGRATNNNYSAILKKFWMMYWPKLV

ILMGIIILIVILNAIFNNVNKNDRMNDNNDADAQKYTTTMKNANNAVKSVVTVENETSKDSSLPKDKASQ

DEVGSGVVYKKSGDTLYIVTNAHVVGDKENQKITFSNNKSVVGKVLGKDKWSDLAVVKATSSDSSVKEI

AIGDSNNLVLGEPILVVGNPLGVDFKGTVTEGIISGLNRNVPIDFDKDNKYDMLMKAFQIDASVNPGNSG

GAVVNREGKLIGVVAAKISMPNVENMSFAIPVNEVQKIVKELETKGKIDYPDVGVKMKNIASLNSFERQA

VKLLGKVKNGVVVDQVDNNGLADQSGLKKGDVITELDGKLLEDDLRFRQIIFSHKDDLKSITAKIYRDGK

EKEINIKLK

SEQ ID NO: 16:
MKFKAIVAITLSLSLLTACGANQHKENSSKSNDTNKKTQQTDNTTQSNTEKQMTPQEAEDIVRNDYKAR

GANENQTLNYKTNLERSNEHEYYVEHLVRDAVGTPLKRCAIVNRHNGTIINIFDDMSEKDKEEFEAFKKRS

PKYNPGMNDQAEMDNESEDIQHHDIDNNKAIQNDLPDQKVDDKNDKNAVNKEEKHDNRENNSAETKV

K

SEQ ID NO: 17:
MDKKKVIKFMINVLPIVLVPLIVERKRIKQHPDVQKVTDATSKVASKTSAAISNTASDVKEYVGDKKQDFE

NKRELKKFAREHDPAYIEKKGEKLAKQNRKDADKMNKILQKNIEKRHKEEQKAREKNEIQRIKDMKKSQK

YEVKAGLTPNKLDEKTEKKGDKLAEKNRKEIAKMNKKLQKNIEKRHKEEQKRQQEADKARIKSFKKYKDY

VAKSASQQNKENNTEA

SEQ ID NO: 18:
MSYHWFKKMLLSTSMLILSSSSSLGLATHTVEAKDNLNGEKPTTNLNHNVTSPSVNSEMNNNETGTPHE

SNQAGNEGTGSNSRDANPDSNNVKPDSNNQNPSPDSKPDPNNPNPGPNPKPDPDKPKPNPEPKPDPDK

PKPNPDPKPDPDKPKPNPDPKPDPNPNPNPKPDPNKPNPNPSPNPNQPGDSNQSGGSKNGGTWNPNAS

-continued

DGSNQGQWQPNGNQGNSQNPTGNDFVSQRFLALANGAYKYNPYILNQINQLGKEYGEVTDEDIYNIIRK

QNFSGNAYLNGLQQQSNYFRFQYFNPLKSERYYRNLDEQVLALITGEIGSMPDLKKPEDKPDSKQRSFEP

HEKDDFTVVKKQEDNKKSASTAYSKSWLAIVCSMMVVFSIMLFLFVKRNKKKNKNESQRR

SEQ ID NO: 19:
MKKTLLASSLAVGLGIVAGNAGHEAQASEADLNKASLAQMAQSNDQTLNQKPIEAGAYNYTFDYEGFTY

HFESDGTHFAWNYHATGANGADMSAQAPATNNVAPSADQSNQVQSQEVEAPQNAQTQQPQASTSNN

SQVTATPTESKASEGSSVNVNDHLKQIAQRESGGNIHAVNPTSGAAGKYQFLQSTWDSVAPAKYKGVSP

ANAPESVQDAAAVKLYNTGGAGHWVTA

---

The invention claimed is:

1. A pharmaceutical composition comprising, a polypeptide comprising: a) an amino acid sequence consisting of SEQ ID NO: 18, or b) an amino acid sequence consisting of at least 35 contiguous amino acid residues from SEQ ID NO: 18, or c) an amino acid sequence having a sequence identity of at least 95% with the amino acid sequence of a), or d) an amino acid sequence having a sequence identity of at least 95% with the amino acid sequence of b), or said polypeptide being antigenic in a mammal, and an immunological adjuvant and a pharmaceutically acceptable carrier, vehicle or diluent.

2. The pharmaceutical composition according to claim 1, wherein the adjuvant is an aluminium based adjuvant.

3. The pharmaceutical composition according to claim 1, wherein the sequence identity defined in c) or d) is at least 95%, at least 96%, at least 97%, at least 98%, and at least 99%.

4. The pharmaceutical composition according to claim 1, wherein the at least 35 contiguous amino acid residues of option b) has an N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, and 370 in SEQ ID NO: 18, wherein the N-terminal first residue will not be higher numbered than 405-L, where L is the number of amino acids defined for option b.

5. The pharmaceutical composition according to claim 1, wherein the polypeptide is fused or conjugated to an immunogenic carrier molecule.

6. The pharmaceutical composition according to claim 1, wherein the immunogenic carrier molecule is a polypeptide that induces T-helper lymphocyte responses in a majority of humans, such as an immunogenic carrier protein selected from the group consisting of keyhole limpet hemocyanin or a fragment thereof, tetanus toxoid or a fragment thereof, diphtheria toxoid or a fragment thereof.

7. The pharmaceutical composition according to claim 1, wherein the polypeptide is capable of inducing an adaptive protective immune response against infection with multi-resistant *S. aureus* in a mammal, in particular in a human being.

8. The pharmaceutical composition according to claim 7, which induces a humoral and/or a cellular immune response.

9. A method for inducing immunity in an animal by administering at least once an immunogenically effective amount of a pharmaceutical composition according to claim 1 so as to induce adaptive immunity against *S. aureus* in the animal.

10. The method according to claim 9, wherein, when the pharmaceutical composition comprising said polypeptide is administered, the animal receives between 0.5 and 5,000 μg of the polypeptide per administration.

11. The method according to claim 9, wherein the animal receives a priming administration and one or more booster administrations.

12. The method according to claim 9, wherein the animal is a human being.

13. The method according to claim 9, wherein the administration is for the purpose of inducing protective immunity against *S. aureus*.

14. The method according to claim 13, wherein the protective immunity is effective in reducing the risk of attracting infection with *S. aureus* or is effective in treating or ameliorating infection with *S. aureus*.

* * * * *